US007501243B2

(12) United States Patent
Reinhard et al.

(10) Patent No.: US 7,501,243 B2
(45) Date of Patent: Mar. 10, 2009

(54) DETECTION OF COLON OR BREAST CANCER BY MEASURING TTK POLYPEPTIDE EXPRESSION

(75) Inventors: Christoph Reinhard, Alameda, CA (US); Anne B. Jefferson, Oakland, CA (US); Vivien W. Chan, San Francisco, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 238 days.

(21) Appl. No.: 10/951,406

(22) Filed: Sep. 27, 2004

(65) Prior Publication Data

US 2005/0059630 A1  Mar. 17, 2005

Related U.S. Application Data

(62) Division of application No. 10/081,119, filed on Feb. 21, 2002, now abandoned.

(60) Provisional application No. 60/271,254, filed on Feb. 21, 2001.

(51) Int. Cl.
*C12Q 1/68* (2006.01)
*C12P 19/34* (2006.01)
*C07H 21/04* (2006.01)
(52) U.S. Cl. .................. 435/6; 435/91.1; 435/91.2; 536/23.1
(58) Field of Classification Search .................. None
See application file for complete search history.

(56) References Cited

U.S. PATENT DOCUMENTS

2001/0051344 A1* 12/2001 Shalon et al. .................. 435/6

FOREIGN PATENT DOCUMENTS

WO   WO 00/56756   9/2000
WO   WO 01/30964   5/2001

OTHER PUBLICATIONS

Dermer et al. Biotechnology 1994, vol. 12, p. 320.*
Chabert et al. Int. J. Cancer 1993, vol. 53, pp. 837-842.*
Cheung et al. Nature Genetics 2003, vol. 33, pp. 422-425.*
Hundt et al., Cancer Epidemiology, Biomarkers and Prevention 2007, vol. 16, pp. 1935-1953.*
Cahill et al., "Characterization of *MAD2B* and other mitotic spindle checkpoint genes", *Genomics*,(1999) vol. 58(2): 181-187.
Genbank Accession No. M86699, 1995.
Hanahan, et al. "The hallmarks of cancer", *Cell*, (2000) vol. 100: 57-70.
Haruki, et al. "Molecular analysis of the mitotic checkpoint genes *BUB1*, *BUBR1*, and *BUB3* in human lung cancers", *Cancer Letters*, (2001) vol. 162: 201-205.
Hogg, et al. "Cell cycle dependent regulation of the protein kinase TTK", *Oncogene*, (1994) vol. 9: 89-96.

Mills, et al. "Expression of TTK , a novel human protein kinase, is associated with cell proliferation", *J. Biol. Chem.*, (1992) vol. 267: 16000-16006.
Mimori, et al. *Oncol. Rep.*, (2001) vol. 8: 39-42.
Olesen, et al. "Mitotic checkpoint genes *hBUB1,hBUB1B, hBUB3*, and *TTK* in human bladder cancer, screening for mutations and loss of heterozygotsity", *Carcinogenesis*, (2001) vol. 22(5): 813-815.
Saffery, et al. "Components of the human spindle checkpoint control mechanism localize specifically to the active centromere on dicentric chromosomes", *Hum. Genet.*, (2000) vol. 107: 376-384.
Schmandt, et al. "IL-2-induced expression of TTk, a serine, threonine, tyrosine kinase, correlates with cell cycle progression", *J. Immunol.*, (1994) vol. 152: 96-105.
Tomizawa, et al. "Tau-tubulin kinase phosphorylates tau at Ser-208 and Ser-210, sites found in paired helical filament-tau", *FEBS*, (2001) vol. 492: 221-227.
Huang et al. Oncogene 1998, vol. 16, pp. 2469-2477.
Agrawal, S. et al. (Feb. 2000). "Antisense Therapeutics: Is It as Simple as Complementary Base Recognition?," *Molecular Medicine Today* 6:72-81.
Branch, A. D. (Feb. 1998). "A Good Antisense is Hard to Find," *Trends in Biochemical Science* 23:45-50.
International Search Report mailed Jun. 25, 2002, for PCT Application No. PCT/US2002/05278 filed Feb. 21, 2002. 2 pages.
Jen, K.-Y. et al. (2000). "Suppression of Gene Expression by Targeted Disruption of Messenger RNA: Available Options and Currents Strategies," *Stem Cells* 18:307-319.
Opalinska, J. B,. et al., (Jul. 2002). "Nucleic-Acid Therapeutics: Basic Principles and Recent Applications," *Nature Reviews: Drug Discovery* 1:503-514.
Supplementary Partial European Search Report mailed May 27, 2005, for European Application No. 02709637.9 filed on Feb. 21, 2002, 4 pages.
U.S. Office Action mailed Feb. 6, 2008, for U.S. Appl. No. 10/951,389, filed Sep. 27, 2004, 10 pages.
U.S. Office Action mailed Feb. 6, 2008, for U.S. Appl. No. 10/951,477, filed Sep. 27, 2004, 11 pages.
U.S. Office Action mailed Jan. 10, 2008, for U.S. Appl. No. 10/951,389, filed Sep. 27, 2004, 9 pages.
U.S. Office Action mailed Jan. 18, 2007, for U.S. Appl. No. 10/951,477, filed Sep. 27, 2004, 9 pages.
U.S. Office Action mailed Oct. 1, 2007, for U.S. Appl. No. 10/951,389, filed Sep. 27, 2004, 10 pages.
U.S. Office Action mailed Sep. 14, 2007, for U.S. Appl. No. 10/951,477, filed Sep. 27, 2004, 12 pages.

(Continued)

*Primary Examiner*—Tracy Vivlemore
(74) *Attorney, Agent, or Firm*—Lisa Alexander; Patricia Tsao

(57) ABSTRACT

The present invention provides methods for identification of cancerous cells by detection of expression levels of TTK, as well as diagnostic, prognostic and therapeutic methods that take advantage of the differential expression of these genes in mammalian cancer. Such methods can be useful in determining the ability of a subject to respond to a particular therapy, e.g., as the basis of rational therapy. In addition, the invention provides assays for identifying pharmaceuticals that modulate activity of these genes in cancers in which these genes are involved, as well as methods of inhibiting tumor growth by inhibiting activity of TTK.

31 Claims, 12 Drawing Sheets

OTHER PUBLICATIONS

European Office Action mailed on Apr. 21, 2008, for European Patent Application 02709637.9 filed on Feb. 21, 2002, 15 pages.

GenBank Accession No. A42861 (NCBI nucleotide database), last updated Apr. 29, 2008, located at <http://www.ncbi.nlm.nih.gov/entrez/viewer.fcgi?db=nuccore&id=2298310>, last visited on May 12, 2008, 1 page.

GenBank Accession No. A42861 (NCBI protein database), last updated Apr. 29, 2008, located at <http://www.ncbi.nlm.nih.gov/sites/entrez?db=protein&cmd=search&term=A42861>, last visited on May 12, 2008, 1 page.

GenBank Accession No. NM 003318, version 003318.3, last updated Feb. 11, 2008, located at <http://www.ncbi.nlm.nih.gov/entrez/viewer.fcgi?db=nuccore&id=34303964>, last visited on May 12, 2008, 4 pages.

GenBank Accession No. NM 003318, version 003318.1, last updated Oct. 31, 2000, located at <http://www.ncbi.nlm.nih.gov/entrez/viewer.fcgi?db=nuccore&id=4507718>, last visited on May 12, 2008, 3 pages.

Iwase, T. et al., (1993). "Identification of Protein-tyrosine Kinase Genes Preferentially Expressed in Embryo Stomach and Gastric Cancer," *Biomedical and Biophysical Research Communications* 194(2):698-705.

Japanese Office Action mailed on Apr. 30, 2008, for Japanese Patent Application 2002-567954 filed Feb. 21, 2002, 8 pages.

\* cited by examiner

DETECTION OF COLON OR BREAST CANCER BY MEASURING TTK POLYPEPTIDE EXPRESSION

CROSS-REFERENCE TO RELATED APPLICATION

This application claims the benefit of U.S. provisional application Ser. No. 60/289,813, filed Feb. 21, 2001, which application is hereby incorporated by reference.

FIELD OF THE INVENTION

The field of the present invention relates to disease diagnosis and treatment of cancer and identification of anti-cancer agents.

BACKGROUND OF THE INVENTION

Mitotic checkpoint genes have become widely studied for their roles in development as well as for their potential role in disease such as cancer. The mitotic checkpoint involves a number of different mechanisms to ensure proper cellular division. For example, the spindle assembly checkpoint modulates the timing of anaphase initiation in response to the improper alignment of chromosomes at the metaphase plate. If defects are detected, a signal is transduced to halt further progression of the cell cycle until correct bipolar attachment to the spindle is achieved. Initially identified in budding yeast, several mammalian spindle checkpoint-associated proteins have recently been identified and partially characterized. These proteins associate with all active human centromeres, including neocentromeres, in the early stages of mitosis prior to the commencement of anaphase. The proteins associated with the checkpoint protein complex (BUB1, BUBR1, BUB3, MAD2), the anaphase-promoting complex (Tsg24, p55CDC), and other proteins associated with mitotic checkpoint control (ERK1, 3F3/2 epitope, hZW10), were found to specifically associate with only the active centromere, suggesting that only active centromeres participate in the spindle checkpoint. Saffery R et al., *Hum Genet.* 107:376-84 (2000).

Tyrosine threonine kinase (TTK), a protein kinase, phosphorylates serine, threonine, and tyrosine hydroxyamino acids (Mills et al,. *Biol. Chem.* 267:16000-6 (1992)). The kinases most closely related to TTK include SPK1 serine, threonine, and tyrosine kinase, the Pim1, PBS2, and CDC2 serine/threonine kinases, and the TIK kinase (Mills et al. *J. Biol. Chem.* 267:16000-6 (1992)). The nucleotide and amino acid sequences of human TTK are provided at, for example, GenBank Accession No. M86699. Expression of TTK is markedly reduced or absent in resting cells and in tissues with a low proliferative index (Hogg et al. *Oncogene* 9:89-96 (1994)). TTK mRNA is expressed in human testis, thymus, bone marrow, and other tissues that contain a large number of proliferating cells and is not detected in tissues that contain few or no dividing cells. TTK expression was detected in several rapidly proliferating cells lines, including various cancer cell lines. TTK expression was also detected and in samples tissue samples from two patients with malignant ovarian cancer (Mills et al., ibid.; Schmandt et al. *J. Immunol.* 152:96-105 (1994)). TTK expression is correlated with cell proliferation, and plays a role in cell cycle control (Hogg et al., ibid.). Very low levels of TTK mRNA and protein are present in starved cells. When cells are induced to enter the cell cycle, levels of TTK mRNA, protein, and kinase activity increase at the G1/S phase of the cell cycle and peak in G2/M. TTK mRNA levels, as well as kinase activity, drop sharply in early G1, whereas protein levels are largely maintained. TTK is a human homologue of the *S. cerevesiae* kinase mps 1 and the *S. pombe* protein mph1, both of which are involved in cell cycle spindle assembly checkpoint, thus indicating that TTK is a spindle checkpoint gene (see, e.g., Cahill et al. *Genomics* 58:181-7 (1999)).

Although mitotic checkpoint impairment has been detected in human cancers (e.g., such impairment is present in about 40% of human lung cancer cell lines) mutations in the MAD mitotic checkpoint genes and the BUB gene family are infrequent. Haruki N et al., *Cancer Lett.* 162:201-205 (2001); Mimori K et al., *Oncol Rep.* 8:39-42 (2001); Cahill et al., ibid.). There is thus a need for identification of mitotic checkpoint genes that have a role in human cancers, as they can serve as informative diagnostic and/or prognostic indicators, and therapeutic targets.

SUMMARY OF THE INVENTION

The present invention provides methods for identification of cancerous cells by detection of expression levels of TTK, as well as diagnostic, prognostic and therapeutic methods that take advantage of the differential expression of these genes in mammalian cancer. Such methods can be useful in determining the ability of a subject to respond to a particular therapy, e.g., as the basis of rational therapy. In addition, the invention provides assays for identifying pharmaceuticals that modulate activity of these genes in cancers in which these genes are involved, as well as methods of inhibiting tumor growth by inhibiting activity of TTK.

In a first embodiment, the present invention provides a method for identifying TTK levels in a sample of a subject suspected of having cancer (e.g., a lung, colon, prostrate or breast tissue biopsy) comprising quantifying the level of TTK in the sample. The identification of increased levels of TTK in the sample provides an indication of impairment of the cell cycle checkpoint in the sampled cells.

In another embodiment, the invention provides a method for determining the characteristics of a malignant or pre-malignant growth comprising determining (either qualitatively or quantitatively) the level of TTK in the cells of the growth, and comparing levels with known levels in various stages of cancer and/or normal tissue. For example, to determine the characteristics of a particular subject's colon cancer, a sample of the cancer may be removed, the levels of TTK in the cancer determined, and the levels compared to normal tissue and/or levels in various stage colon cancers derived from the same cell type. The levels of TTK identified in the sample can thus be indicative of various characteristics of the malignant or pre-malignant growth, as determined by the characteristics of known tissue and cancers. The TTK levels can be compared directly to the levels in other single samples, or may be compared to a standard that is derived from the data of multiple samples.

In another embodiment, the TTK levels of a sample can be used as one index for determining the appropriate therapeutic intervention for a subject with a malignant or pre-malignant growth. Highly increased levels of TTK, for example, can be indicative of the need for more aggressive therapy, as it is indicative of a later stage cancer. Alternatively, the level of TTK expression may be indicative of the responsiveness of a subject to a particular pharmaceutical, and in particular to a therapeutic intervention that affects the cancer via the mitotic checkpoint.

In another embodiment, the invention features a method for identifying agents for inhibiting growth of a tumor, particular by a breast or colon tumor, by contacting a cell expressing TTK with a candidate agent, and assessing the effect of the agent upon TTK activity.

Accordingly, in one aspect the invention features a method of diagnosing cancer in a subject, the method comprising detection of TTK polynucleotide or polypeptide in a test sample obtained from a subject so as to determine a level of expression of the gene product; and comparing the level of expression of the TTK in the test sample to a level of expression in a normal cell corresponding to the same tissue; wherein detection of an expression level of TTK in the test sample that is significantly increased from the level of expression in a normal cell indicates that the test cell is cancerous. In specific embodiments, the cancer is other than ovarian cancer, with colon cancer and breast cancer being of particular interest.

In another aspect, the invention features a method for determining the prognosis of a cancerous disease in a subject, the method comprising detecting expression of TTK in a test cell from the subject; and comparing a level of expression of TTK in the test cell with a level of TTK expression in a control cell; wherein the level of expression of TTK in the test cell relative to the level of expression in the control cell is indicative of the prognosis of the cancerous disease. For example, where the control cell is a normal cell, an elevated level of TTK expression in the test cell relative to the normal cell is indicative of the continued presence of cancerous cells in the subject and thus a relatively poorer prognosis than where the level of TTK expression in the test cell is at a level comparable to that found in an normal (non-cancer) cell. In specific embodiments, progress of a cancer other than ovarian cancer is of particular interest, especially colon and breast cancer.

In another aspect, the invention features a method for inhibiting growth of a cancerous cell comprising introducing into a cell an antisense polynucleotide for inhibition of TTK expression, wherein inhibition of TTK expression inhibits replication of the cancerous cell.

In still another aspect, the invention features a method for assessing the tumor burden of a subject, the method comprising detecting a level of TTK expression in a test sample from a subject, the test sample suspected of comprising increased TTK expression; wherein detection of the level of TTK expression in the test sample is indicative of the tumor burden in the subject, with an increased level of TTK expression in the test sample relative to a control non-cancer cell indicates the presence of a tumor in the subject.

In yet another aspect, the invention features a method of identifying an agent having anti-TTK activity, the method comprising contacting a cancerous cell displaying elevated expression of TTK with a candidate agent; and determining the effect of the candidate agent on TTK activity; wherein a decrease in TTK activity indicates that the agent has anti-TTK activity. In specific embodiments, TTK activity is detected by detecting TTK expression or by detecting a biological activity of TTK In yet another aspect, the invention features an assay for identifying a candidate agent that inhibits growth of a cancerous cell, comprising contacting a cell expressing TTK polypeptide with a candidate agent; and detecting activity of the TTK polypeptide, comparing the activity of the TTK polypeptide in the cell in the presence of the candidate agent to activity of a TTK polypeptide in a cell in the absence of the candidate agent; wherein reduction of TTK activity in the presence of the candidate agent relative to TTK activity in the absence of the candidate agent indicates that the candidate agent reduces TTK activity and inhibits growth of a cancerous cell.

A primary object of the invention is to exploit TTK as a therapeutic target, e.g. by identifing candidate agents that modulate, usually that decrease, TTK activity in a target cell in order to, for example, inhibit cell growth.

An object of the present invention is to inhibit tumor growth by inhibition of activity of a mitotic checkpoint gene product, particularly though inhibition of TTK activity in the target tumor cell.

Another object of the invention is to facilitate rational cancer therapy. For example, where the cancer in the subject is associated with increased TTK activity levels, a therapeutic agent is selected accordingly so as to facilitate reduction of TTK activity levels.

Another object of the present invention is to design clinical trials based on levels of TTK expression in a cancer, and more particularly to design clinical trials based on TTK expression in combination with other patient attributes.

Yet another object of the invention is to identify the association of TTK expression and intervention attributes that yield efficacious changes in selected disease progression measures.

An advantage of the invention is the ability to project disease progression based on expression of TTK in a malignant or pre-malignant growth.

Another advantage of the present invention is that it allows a more systematic approach for intervention of a cancerous disease based upon objective indicia.

These and other objects, advantages, and features of the invention will become apparent to those persons skilled in the art upon reading the details of the methods as more fully described below.

DETAILED DESCRIPTION OF PREFERRED EMBODIMENTS

Figure 1:
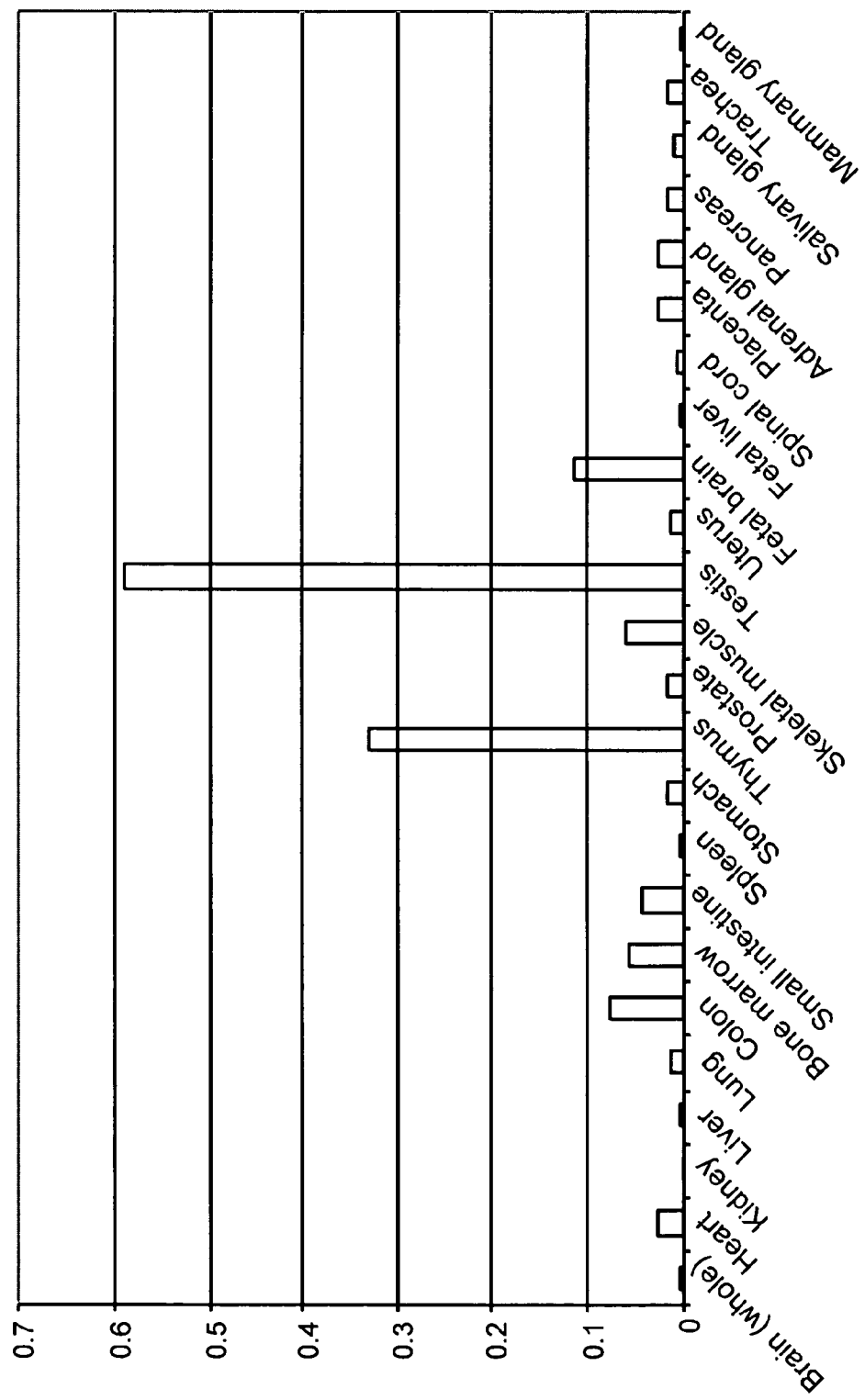
FIG. 1 is a bar graph illustrating expression of TTK in various normal tissue types as detected by PCR.

Before the present invention is described, it is to be understood that this invention is not limited to particular methodologies described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of such cells and reference to "the agent" includes reference to one or more agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "polynucleotide" and "nucleic acid", used interchangeably herein, refer to a polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences (see, e.g., Niwa et al. (1999) *Cell* 99(7):691-702). The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) *Nucl. Acids Res.* 24:1841-1848; Chaturvedi et al. (1996) *Nucl. Acids Res.* 24:2318-2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein "TTK polynucleotide" and "TTK polypeptide" encompass polynucleotides and polypeptides having sequence similarity or sequence identity to the human TTK (having GenBank accession number M86699; SEQ ID NO:13 and 14), or the *S. cerevesiae* kinase mps1 gene and gene products (SEQ ID NO:29 and 30), the *S. pombe* protein mph1 gene and gene products (SEQ ID NO:31 and 32), and other genes and gene products related to TTK, such as SPK1 (SEQ ID NO: 15 and 16), Pim1 (SEQ ID NO:17 and 18), PBS2 (SEQ ID NO:19 and 20), CDC2 (SEQ ID NO:21 and 22), and TIK (SEQ ID NO:23 and 24) of at least about 65%, preferably at least about 80%, more preferably at least about 85%, and can be about 90%, 91%, 92%, 93%, 94%, 95%, 96%, 97%, 98%,99% or more. Sequence similarity and sequence identity are calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. In general, percent sequence identity is calculated by counting the number of residue matches (e.g., nucleotide residue or amino acid residue) between the query and test sequence and dividing total number of matches by the number of residues of the individual sequences found in the region of strongest alignment. Thus, where 10 residues of an 11 residue query sequence matches a test sequence, the percent identity above would be 10 divided by 11, or approximately, 90.9%. Algorithms for computer-based sequence analysis are known in the art, such as BLAST (see, e.g., Altschul et al., *J. Mol. Biol.*, 215:403-10 (1990)), particularly the Smith-Waterman homology search algorithm as implemented in MPSRCH program (Oxford Molecular). For the purposes of this invention, a preferred method of calculating percent identity is the Smith-Waterman algorithm, using the following. Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1. The human TTK cDNA is represented by the polynucleotide sequence of SEQ ID NO:13 and the human TTK polypeptide is represented by the sequence of SEQ ID NO:14.

"Antisense polynucleotide" or "antisense oligonucleotide" are used interchangeably herein to mean an unmodified or modified nucleic acid having a nucleotide sequence complementary to a given polynucleotide sequence (e.g., a polynucleotide sequence encoding. TTK) including polynucleotide sequences associated with the transcription or translation of the given polynucleotide sequence (e.g., a promoter of a polynucleotide encoding TTK), where the antisense polynucleotide is capable of hybridizing to a TTK-encoding polynucleotide sequence. Of particular interest are antisense polynucleotides capable of inhibiting transcription and/or translation of a TTK-encoding polynucleotide either in vitro or in vivo.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing to create a continuous open reading frame encoding TTK.

A "variant" as used in the context of a "variant polypeptide" refers to an amino acid sequence that is altered by one or more amino acids relative to a reference amino acid sequence. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, inserted, or deleted without abolishing biological or immunological activity can be found using computer programs well known in the art, for example, DNAStar software.

A "deletion" is defined as a change in either amino acid or nucleotide sequence in which one or more amino acid or nucleotide residues, respectively, are absent as compared to reference amino acid sequence or nucleotide sequence. Deletions can be of any length, but are preferably approximately 50, 20, 15, 10, 5 or 3 amino acids or nucleotides in length.

An "insertion" or "addition" is that change in an amino acid or nucleotide sequence which has resulted in the addition of one or more amino acid or nucleotide residues, respectively, as compared to a reference amino acid sequence or nucleotide sequence. Insertions or additions can be of any length, but are preferably approximately 50, 20, 15, 10, 5 or 3 amino acids or nucleotides in length.

A "substitution" results from the replacement of one or more amino acids or nucleotides by different amino acids or nucleotides, respectively, as compared to a reference amino acid sequence or nucleotide sequence. Substitutions can be of any length, but are preferably approximately 50, 20, 15, 10, 5 or 3 amino acids or nucleotides in length.

The terms "single nucleotide polymorphism" and "SNP" refer to polymorphisms of a single base change relative to a reference sequence.

The term "biologically active" refers to gene product, usually a polypeptide, having structural, regulatory, or biochemical functions of a naturally occurring gene product, e.g., protein. "Immunologically active" defines the capability of the natural, recombinant, or synthetic polypeptide, or any oligopeptide thereof, to elicit a specific immune response in appropriate animals or cells and to bind with specific antibodies.

The term "derivative" as used herein refers to the chemical modification of a nucleic acid or amino acid sequence relative to a reference nucleic acid or amino acid sequence. Illustrative of such modifications would be replacement of hydrogen by an alkyl, acyl, or amino group. A nucleic acid derivative generally encodes a polypeptide which retains essential biological characteristics of the polypeptide encoded by the reference nucleic acid (e.g., the "parent" molecule).

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

"Stringency" typically occurs in a range from about Tm −5° C. (5° C. below the Tm of the probe or antibody) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs, Dictionary of Biotechnology, Stockton Press, New York N.Y. (1994)). Amplification as carried out in the polymerase chain reaction technologies is described in Dieffenbach et al., PCR Primer, a Laboratory Manual, Cold Spring Harbor Press, Plainview N.Y. (1995).

The term "transformation" as used herein refers to a permanent or transient genetic change, induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

The term "construct" as used herein refers to a recombinant nucleic acid, generally recombinant DNA, that has been generated for the purpose of the expression of a specific nucleotide sequence(s), or is to be used in the construction of other recombinant nucleotide sequences.

As used herein, the term "differentially expressed" generally refers to a polynucleotide that is expressed at levels in a test cell that differ significantly from levels in a reference cell, e.g., mRNA is found at levels at least about 25%, at least about 50% to about 75%, at least about 90% increased or decreased, generally at least about 1.2-fold, at least about 1.5-fold, at least about 2-fold, at least about 5-fold, at least about 10-fold, or at least about 50-fold or more increased or decreased in a cancerous cell when compared with a cell of the same type that is not cancerous. The comparison can be made between two tissues, for example, if one is using in situ hybridization or another assay method that allows some degree of discrimination among cell types in the tissue. The comparison may also be made between cells removed from their tissue source. "Differential expression" refers to both quantitative, as well as qualitative, differences in the genes' temporal and/or cellular expression patterns among, for example, normal and neoplastic tumor cells, and/or among tumor cells which have undergone different tumor progression events.

The terms "correspond to" or "represents" as used in, for example, the phrase "polynucleotide corresponds to a differentially expressed gene" are used to refer to the relationship between a given polynucleotide and the gene from which the polynucleotide sequence is derived (e.g., a polynucleotide that is derived from a coding region of the gene, a splice variant of the gene, an exon, and the like) or to which the polynucleotide hybridizes to under stringer conditions.

"Differentially expressed polynucleotide" as used herein refers to a nucleic acid molecule (RNA or DNA) comprising a sequence that represents or corresponds to a differentially expressed gene, e.g., the differentially expressed polynucleotide comprises a sequence (e.g., an open reading frame encoding a gene product; a non-coding sequence) that uniquely identifies a differentially expressed gene so that detection of the differentially expressed polynucleotide in a sample is correlated with the presence of a differentially expressed gene in a sample. "Differentially expressed polynucleotides" is also meant to encompass fragments of the disclosed polynucleotides, e.g., fragments retaining biological activity, as well as nucleic acids homologous, substantially similar, or substantially identical (e.g., having about 90% sequence identity) to the disclosed polynucleotides.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

As used herein, the term "a polypeptide associated with cancer" (e.g., as in polypeptide associated with colon cancer) refers to a polypeptide that is present at relatively higher or lower levels in a cancer cell relative to a normal cell of the same type.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or relieving the disease symptom, i.e., causing regression of the disease or symptom. Thus "treatment of cancer" thus encompasses one or more of inhibition of cellular proliferation, inhibition of metastasis, and the like.

The terms "individual," "subject," "host," and "patient," used interchangeably herein and refer to any mammalian subject for whom diagnosis, treatment, or therapy is desired, particularly humans. Other subjects may include cattle, dogs, cats, guinea pigs, rabbits, rats, mice, horses, and so on.

The phrase "specific binding pair" as used herein comprises a specific binding member and a binding partner which have a particular specificity for each other and which bind to each other in preference to other molecules under stringent conditions. Examples of specific binding pairs are antigens and antibodies, molecules and receptors and complementary nucleotide sequences. Other examples of binding pairs will be apparent to one skilled in the art upon reading the present disclosure. Further, the term "specific binding pair" is also applicable where either or both of the specific binding member and the binding partner comprise a part of a larger molecule. In embodiments in which the specific binding pair are nucleic acid sequences, they are preferably between 10 to 200 nucleotides long, more preferably greater than 15 to 100 nucleotides long.

By "antibody" is meant an immunoglobulin protein which is capable of binding an antigen. Antibody as used herein is meant to include the entire antibody as well as any antibody fragments (e.g., $F(ab')_2$, Fab', Fab, Fv) capable of binding the epitope, antigen, or antigenic fragment of interest.

Antibodies of the invention are immunoreactive or immunospecific for and therefore specifically and selectively bind to a protein of interest, e.g., human TTK protein. Antibodies which are immunoreactive and immunospecific for human TTK are preferred. Antibodies for human TTK are preferably immunospecific—i.e., not substantially cross-reactive with related materials, although they may recognize TTK homologs across species. The term "antibody" encompasses all types of antibodies (e.g., monoclonal and polyclonal).

By "binds specifically" is meant high avidity and/or high affinity binding of an antibody to a specific polypeptide, e.g., epitope of a TTK protein. Antibody binding to its epitope on this specific polypeptide is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g., by use of appropriate controls.

The terms "cancer", "neoplasm", "tumor", and the like are used interchangeably herein to refer to cells which exhibit relatively autonomous growth, so that they exhibit an aberrant growth phenotype characterized by a significant loss of control of cell proliferation. In general, cells of interest for detection or treatment in the present application include pre-malignant (e.g., benign hyperplasiac), malignant, metastatic, and non-metastatic cells.

"TTK activity" as used herein refers to activity of the TTK polypeptide in phosphorylation of a recipient substrate.

"Modulation of TTK activity" as used herein refers to an increase or decrease in TTK activity that can be a result of, for example, interaction of an agent with a TTK polypeptide (e.g., reversible or irreversible binding of an inhibitory agent so as to interfere with TTK polypeptide interaction with a donor molecule or a recipient (acceptor) molecule in the phosphorylation activity of TTK), inhibition of TTK transcription and/or translation (e.g., through antisense interaction with the TTK gene or TTK transcript, through modulation of transcription factors that facilitate TTK expression), and the like. Modulation of TTK activity that results in a decrease of TTK activity is of particular interest in the invention. In this context, TTK activity can be decreased by an inhibitory agent at least 10%, 25%, 50%, 75%, 85%, 90%, up to 100% relative to TTK activity in the absence of an agent. TTK activity can be assessed by assaying enzymatic activity, by assessing TTK polypeptide levels, or by assessing TTK transcription levels. Comparisons of TTK activity can also be accomplished by comparing TTK activity assessed (either qualitatively or quantitatively) in a test sample to a standard TTK activity (e.g., a level of TTK activity in the absence of an inhibitory agent or agonist, that is associated with a normal cell, a level of TTK activity of a cancerous cell of a selected tissue type, and the like).

Overview

Human TTK is a mitotic checkpoint gene which encodes an 857 amino acid protein that exhibits activity of a mixed specificity (tyr/thr) kinase. TTK is expressed in rapidly proliferating tissues such as testis and thymus. See, e.g., Mills G B et al., *J Biol Chem.* 267:16000-6 (1992). The present invention is based upon the finding that TTK is differentially expressed in colon tumor cells relative to normal colon cells as detected by microarray analysis. Differential expression was confirmed in cell lines derived from various forms of cancer, indicating that the involvement of TTK in cancer as a more general mechanism. In addition, disruption of TTK function using antisense oligonucleotides to "knock-out" TTK message decreased proliferation, inhibited anchorage independent growth, and induced apoptosis of cancer cell lines, including a metastatic breast cancer cell line (MDA-MB-213) and a colorectal carcinoma cell line (SW620). These data indicate that TTK can be a therapeutic target for chemotherapy in cancers in which TTK is overexpressed.

The identification of the association of TTK with cancer, and the confirmation that inhibition of TTK activity (e.g., by reducing TTK expression) serves as the basis for the materials and methods of the invention, such as are disclosed and discussed herein, for use in, for example, diagnosing cancer of a patient, particularly a cancer that is susceptible to treatment by decreasing activity of TTK. The invention also provides for planning and selection of appropriate therapeutic and/or prophylactic treatment, permitting streamlining of treatment by targeting those most likely to benefit. The invention also provides for treatment of a cancer associated with aberrant TTK levels (e.g., associated with overexpression or overproduction of TTK), e.g. by inhibition of gene product production (e.g., decreasing levels of transcription and/or translation), by decreasing TTK activity (e.g., by decreasing TTK gene product production (e.g., at the level of transcription or translation) and/or by reducing one or more of TTK's kinase activities).

Various aspects of the invention will now be described in more detail.

Diagnostic Methods

In one aspect the invention is based on the discovery that TTK activity is present at higher levels in cancerous cells (particularly in colon cancer and breast cancer) than in normal cells of the same cell type. This discovery serves as the basis for identification of cancerous cells, as well as identification of tumors that are susceptible to therapy by inhibiting activity of TTK, e.g., by inhibiting TTK expression at the level of transcription or translation or both, by inhibiting TTK activity, and the like.

TTK gene products e.g. TTK encoding mRNA or TTK polypeptides are of particular interest as markers (e.g., in bodily fluids (such as blood) or in tissues) to detect the earliest changes along the carcinogenesis pathway (e.g., to differentiate cancerous tissue from non-cancerous tissue) and/or to monitor the efficacy of various therapies and preventive interventions. For example, a relatively increased level of expression of TTK compared to normal cells or tissues of the same type can be indicative of a poorer prognosis, and therefore warrant more aggressive therapy (e.g., chemo- or radiotherapy) for a patient or vice versa. The correlation of surrogate tumor specific features with response to treatment and outcome in patients can define prognostic indicators that allow the design of tailored therapy based on the molecular profile of the tumor. These therapies include antibody targeting, antagonists (e.g., small molecules), and gene therapy. Determining TTK expression and comparison of a patient's profile with known expression in normal tissue and variants of the disease allows a determination of the best possible treatment for a patient, both in terms of specificity of treatment and in terms of comfort level of the patient. Surrogate tumor markers, such as polynucleotide expression, can also be used to better classify, and thus diagnose and treat, different forms and disease states of cancer. Two classifications widely used in oncology that can benefit from identification of TTK expression levels are staging of the cancerous disorder, and grading the nature of the cancerous tissue.

TTK polynucleotides, as well as their encoded gene products, can be useful to monitor patients having or susceptible to cancer to detect potentially malignant events at a molecular level before they are detectable at a gross morphological level. In addition, detection of TTK gene products can be useful as therametrics, e.g., to assess the effectiveness of therapy by using the polynucleotides or their encoded gene products, to assess, for example, tumor burden in the patient before, during, and after therapy.

Furthermore, a polynucleotide identified as corresponding to a gene that is differentially expressed in, and thus is important for, one type of cancer can also have implications for development or risk of development of other types of cancer, e.g., where a polynucleotide represents a gene differentially expressed across various cancer types. Thus, for example, expression of a polynucleotide corresponding to a gene that has clinical implications for metastatic colon cancer can also have clinical implications for stomach cancer or endometrial cancer.

In making a diagnosis, prognosis, risk assessment, or measurement of tumor burden based on the enzymatic activity of TTK or the expression levels of TTK polypeptide or TTK encoding polynucleotides, activity or expression levels may be compared to those of suitable cancerous or non-cancerous control samples. For example, a diagnosis of cancer can be made if TTK activity is increased at by 25%, 50%, 75%, 90%, up to 100%, or, alternatively by 5-fold, 10-fold, 50-fold, or more than 100-fold relative to a normal non-cancerous cell of the same tissue type.

Other gene products that are differentially expressed in cancerous cells relative to, for example, non-cancer cells of between cancer cells of differing malignant potential (e.g., non-malignant tumor cells versus cells of high potential malignancy) can also be assayed in addition to TTK for differential expression in a test cell. Such exemplary gene products include, but are not necessarily limited to MAPKAP kinase 2 (SEQ ID. No. 33 and 34), MARCKS (SEQ ID NO:35 and 36) and/or IGF2 (SEQ ID NO:37 and 38).

Staging. Staging is a process used by physicians to describe how advanced the cancerous state is in a patient. Staging assists the physician in determining a prognosis, planning treatment and evaluating the results of such treatment. Staging systems vary with the types of cancer, but generally involve the following "TNM" system: the type of tumor, indicated by T; whether the cancer has metastasized to nearby lymph nodes, indicated by N; and whether the cancer has metastasized to more distant parts of the body, indicated by M. Generally, if a cancer is only detectable in the area of the primary lesion without having spread to any lymph nodes it is called Stage I. If it has spread only to the closest lymph nodes, it is called Stage II. In Stage II, the cancer has generally spread to the lymph nodes in near proximity to the site of the primary lesion. Cancers that have spread to a distant part of the body, such as the liver, bone, brain or other site, are Stage IV, the most advanced stage.

The differential expression level of TTK can facilitate fine-tuning of the staging process by identifying markers for the aggressiveness of a cancer, e.g. the metastatic potential, as well as the presence in different areas of the body. Thus, a Stage II cancer with a large differential level of expression of TTK can signify a cancer with a high metastatic potential and can be used to change a borderline Stage II tumor to a Stage III tumor, justifying more aggressive therapy.

Grading of cancers. Grade is a term used to describe how closely a tumor resembles normal tissue of its same type. The microscopic appearance of a tumor is used to identify tumor grade based on parameters such as cell morphology, cellular organization, and other markers of differentiation. As a general rule, the grade of a tumor corresponds to its rate of growth or aggressiveness, with undifferentiated or high-grade tumors generally being more aggressive than well differentiated or low-grade tumors. The following guidelines are generally used for grading tumors: 1) GX Grade cannot be assessed; 2) G1 Well differentiated; G2 Moderately well differentiated; 3) G3 Poorly differentiated; 4) G4 Undifferentiated. TTK activity levels (e.g., expression levels) can be especially valuable in determining the grade of the tumor, as they not only can aid in determining the differentiation status of the cells of a tumor, they can also identify factors other than differentiation that are valuable in determining the aggressiveness of a tumor, such as metastatic potential.

Detection of colon cancer. Polynucleotides and polypeptides corresponding to TTK can be used to detect colon cancer in a subject. Colorectal cancer is one of the most common neoplasms in humans and perhaps the most frequent form of hereditary neoplasia. Prevention and early detection are key factors in controlling and curing colorectal cancer. Colorectal cancer begins as polyps, which are small, benign growths of cells that form on the inner lining of the colon. Over a period of several years, some of these polyps accumulate additional mutations and become cancerous. Multiple familial colorectal cancer disorders have been identified, which are summarized as follows: 1) Familial adenomatous polyposis (FAP); 2) Gardner's syndrome; 3) Hereditary nonpolyposis colon cancer (HNPCC); and 4) Familial colorectal cancer in Ashkenazi Jews. The expression of appropriate polypeptide and polynucleotides can be used in the diagnosis, prognosis and management of colorectal cancer. Detection of colon cancer can be determined using expression levels of TTK alone or in combination with the levels of expression of other genes differentially expressed in colon cancer. Determination of the aggressive nature and/or the metastatic potential of a colon cancer can be determined by comparing levels of TTK with a level associated with a normal cell, and comparing total levels of another sequence known to be differentially expressed, or otherwise be a marker of, cancerous tissue, e.g., expression of p53, DCC, ras, FAP (see, e.g., Fearon E R, et al., $Cell$ (1990) 61(5):759; Hamilton S R et al., $Cancer$ (1993) 72:957; Bodmer W, et al., $Nat Genet.$ (1994) 4(3):217; Fearon E R, $Ann N Y Acad Sci.$ (1995) 768:101)or MAPKAP kinase 2 (SEQ ID. No. 33 and 34), MARCKS (SEQ ID NO:35 and 36) and/or IGF2 (SEQ ID NO:37 and 38). For example, development of colon cancer can be detected by examining the level of expression of a gene corresponding to a polynucleotides described herein to the levels of oncogenes (e.g. ras) or tumor suppressor genes (e.g. FAP or p53). Thus expression of specific marker polynucleotides can be used to discriminate between normal and cancerous colon tissue, to discriminate between colon cancers with different cells of origin, to. discriminate between colon cancers with different potential metastatic rates, etc. For a review of markers of cancer, see, e.g., Hanahan et al. (2000) Cell 100:57-70.

Detection of breast cancer. The majority of breast cancers are adenocarcinomas subtypes, which can be summarized as follows: 1) ductal carcinoma in situ (DCIS), including comedocarcinoma; 2) infiltrating (or invasive) ductal carcinoma (IDC); 3) lobular carcinoma in situ (LCIS); 4) infiltrating (or invasive) lobular carcinoma (ILC); 5) inflammatory breast cancer; 6) medullary carcinoma; 7) mucinous carcinoma; 8) Paget's disease of the nipple; 9) Phyllodes tumor; and 10) tubular carcinoma.

The expression levels of TTK can be used in the diagnosis and management of breast cancer, as well as to distinguish between types of breast cancer. Detection of breast cancer can be determined using expression levels of TTK, either alone or in combination with expression of other gene known to be differentially expressed in breast cancer. Determination of the aggressive nature and/or the metastatic potential of a breast cancer can also be determined by comparing levels of TTK and comparing levels of another sequence known to vary in cancerous tissue, e.g. ER expression. In addition, development of breast cancer can be detected by examining the ratio of expression of TTK to the levels of steroid hormones (e.g., testosterone or estrogen) or to other hormones (e.g., growth hormone, insulin). Thus expression of specific marker polynucleotides and polypeptides can be used to discriminate between normal and cancerous breast tissue, to discriminate between breast cancers with different cells of origin, to discriminate between breast cancers with different potential metastatic rates, etc.

Detection Methods

A number of methods are known in the art for analyzing biological samples from individuals to determine whether the individual has increased expression of a TTK gene product (e.g., RNA or protein) by detecting the TTK gene product in a biological sample from that subject. As discussed above, the purpose of such analysis may be used for diagnosis, to detect the presence of an existing cancer, to help identify the type of cancer, to assist a physician in determining the severity or likely course of the cancer, and/or to optimize treatment of it. In specific non-limiting embodiments, the methods are useful for detecting cancer cells, facilitating diagnosis of cancer and the severity of a cancer (e.g., tumor grade, tumor burden, and the like) in a subject, facilitating a determination of the prognosis of a subject, and assessing the responsiveness of the subject to therapy (e.g., by providing a measure of therapeutic effect through, for example, assessing tumor burden during or following a chemotherapeutic regimen). In additional embodiments, the methods are useful for classification or stratification of cancer cells, e.g., for the purpose of selecting patients to be included in a clinical trial population, for selecting an appropriate therapy (e.g., selecting therapy according to an expression profile of the cancerous cells), and the like.

Kits

The detection methods can be provided as part of a kit. Thus, the invention further provides kits for detecting the presence and/or a level of TTK activity e.g., by detection of a TTK-encoding mRNA and/or a polypeptide encoded thereby or by measuring TTK activity, in a biological sample. Procedures using these kits can be performed by clinical laboratories, experimental laboratories, medical practitioners, or private individuals. The kits of the invention for detecting TTK polypeptide that is differentially expressed in cancer cells comprise a moiety that specifically binds the polypeptide, which may be a specific antibody. The kits of the invention for detecting a TTK-encoding polynucleotide that is differentially expressed in cancer cells comprise a moiety that specifically hybridizes to such a polynucleotide such as a primer. The kits of the invention for detecting TTK activity comprise a recipient substrate capable of being phosphorylated by TTK, and a labeled donor substrate. The kits may optionally provide additional components that are useful in the procedure, including, but not limited to, buffers, developing reagents, labels, reacting surfaces, means for detection, control samples, standards, instructions, and interpretive information.

Screening for TTK Nucleic Acid or Polypeptide

Methods for detection of TTK activity include screening for the presence of TTK nucleic acid sequences representing an expressed TTK gene or alleles or variants thereof, and detecting the TTK polypeptide. The methods make use of biological samples from individuals that are suspected of contain the nucleic acid sequences or polypeptide. Examples of biological samples include blood, plasma, serum, tissue samples, tumor samples, saliva and urine.

Exemplary approaches for detecting TTK nucleic acid or polypeptides include: (a) determining the presence of the polypeptide encoded by the TTK gene; (b) using a specific binding member capable of binding to a TTK nucleic acid sequence (e.g., a known complementary sequence), the specific binding member comprising a nucleic acid that hybridizes with the TTK sequence under stringent conditions (c) using a substance comprising an antibody domain with specificity for a TTK nucleic acid sequence or the polypeptide encoded by it, the specific binding member being labeled to allow detection of the specific binding member to its binding partner is detectable; (d) using PCR involving one or more primers to determine relative levels of TTK in a sample from a patient; and (e) using an assay for TTK activity, e.g., phosphorylation of a TTK substrate.

The determination of TTK levels can include both levels of normal TTK and/or variant forms of TTK. A variant form of the gene may contain one or more insertions, deletions, substitutions and/or additions of one or more nucleotides compared with the wild-type sequence which may or may not alter the gene function. Differences at the nucleic acid level are not necessarily reflected by a difference in the amino acid sequence of the encoded polypeptide due to the degeneracy of the genetic code. However, a mutation or other difference in a gene may result in a frame-shift or stop codon, which could seriously affect the nature of the polypeptide produced (if any), or a point mutation or gross mutational change to the encoded polypeptide, including insertion, deletion, substitution and/or addition of one or more amino acids or regions in the polypeptide.

A mutation in a promoter sequence or other regulatory region may alter (e.g., reduce or enhance) expression from the gene or affect the processing or stability of the mRNA transcript.

There are various methods for detecting a particular nucleic acid sequence in a test sample. Tests may be carried out on preparations containing mRNA or cDNA generated from isolated mRNA in a manner that reflects the relative levels of mRNA transcripts in the sample. Levels of RNA can be determined specific amplification reaction such as PCR using one or more pairs of primers may be employed to amplify a region of the nucleic acid, and preferably a region with less homology to other genes. Nucleic acid for testing may be prepared from nucleic acid removed from cells or in a library using a variety of other techniques such as restriction enzyme digest and electrophoresis.

Nucleic acid may be screened using a TTK-specific probe. Such a probe corresponds in sequence to a region of the TTK gene, or its complement. Under stringent conditions, specific hybridization of such a probe to test nucleic acid is indicative of the presence of the TTK nucleic acid in a sample. For efficient screening purposes, more than one probe may be used on the same test sample. The probe may contain as few as 15, 20, 50 or 100 nucleotides of the TTK gene of SEQ ID. No. 13 or may be as long as or 500, 1 kb or as much as 3.8 kb or. longer in length.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the mutation or polymorphism on a denaturing polyacrylamide DNA sequencing gel, with specific bands that are linked to the gene variants being selected. This can be done simultaneous to or sequentially to determining the level of a normal TTK sequence, e.g., to determine the combinatory levels of total TTK.

The presence of absence of a lesion in a promoter or other regulatory sequence may also be assessed by determining the level of mRNA production by transcription or the level of polypeptide production by translation from the mRNA. The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene or a variant or allele is digested with the same enzyme or enzymes.

A test sample of nucleic acid may be provided for example by extracting nucleic acid from cells, e.g., cells from a tumor biopsy.

Detection of TTK Polypeptides

There are various methods for determining the presence or absence in a test sample of a TTK polypeptide. A sample may be tested for the presence of a binding partner for a specific binding member such as an antibody (or mixture of antibodies), specific for wild-type TTK and/or one or more particular variants (e.g., allelic variants) of the TTK polypeptide. In such cases, the sample may be tested by being contacted with a specific binding member such as an antibody under appropriate conditions for specific binding. Where a panel of antibodies is used, different reporting labels may be employed for each antibody so that binding of each can be determined. In addition to detection of TTK polypeptides using anti-TTK antibodies, TTK polypeptide can also be identified using TTK-specific activity assays.

Arrays

Binding agents (such as antibodies or nucleic acid sequences) can also be immobilized in small, discrete locations and/or as arrays on solid supports or on diagnostic chips. These approaches can be particularly valuable as they can provide great sensitivity, particularly through the use of fluorescently labeled reagents, require only very small amounts of biological sample from individuals being tested and allow a variety of separate assays can be carried out simultaneously. This latter advantage can be useful as it provides an assay for different proteins (e.g., an oncogene or tumor suppressor) in tandem with the assay for TTK. Thus, in a further aspect, the present invention provides a support or diagnostic chip having immobilized thereon one or more binding agents capable of specifically binding TTK nucleic acid or polypeptides, optionally in combination with other reagents needed to carrying out an assay.

Methods for Expression of TTK Polypeptide

The full-length or partial polypeptides encoded by TTK may be expressed in any expression system, including, for example, bacterial, yeast, insect, amphibian and mammalian systems. Suitable vectors and host cells for which are described in U.S. Pat. No. 5,654,173. Appropriate polynucleotide constructs are purified using standard recombinant DNA techniques as described in, for example, Sambrook et al., (1989) *Molecular Cloning: A Laboratory Manual*, 2nd ed. (Cold Spring Harbor Press, Cold Spring Harbor, N.Y.), and under current regulations described in United States Dept. of HHS, National Institute of Health (NIH) Guidelines for Recombinant DNA Research.

Bacteria. Expression systems in bacteria include those described in Chang et al., *Nature* (1978) 275:615, Goeddel et al., *Nature* (1979) 281:544, Goeddel et al., *Nucleic Acids Res.* (1980) 8:4057; EP 0 036,776, U.S. Pat. No. 4,551,433, DeBoer et al., *Proc. Natl. Acad. Sci. (USA)* (1983) 80:21-25, and Siebenlist et al., *Cell* (1980) 20:269.

Yeast. Expression systems in yeast include those described in Hinnen et al., *Proc. Natl. Acad. Sci. (USA)* (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459, Roggenkamp et al., *Mol. Gen. Genet.* (1986) 202:302) Das et al., *J. Bacteriol.* (1984) 158:1165; De Louvencourt et al., *J. Bacteriol.* (1983) 154:737, Van den Berg et al., *Bio/Technology* (1990) 8:135; Kunze et al., *J. Basic Microbiol.* (1985) 25:141; Cregg et al., *Mol. Cell. Biol.* (1985) 5:3376, U.S. Pat. Nos. 4,837,148 and 4,929,555; Beach and Nurse, *Nature* (1981) 300:706; Davidow et al., *Curr. Genet.* (1985) 10:380, Gaillardin et al., *Curr. Genet.* (1985) 10:49, Ballance et al., *Biochem. Biophys. Res. Commun.* (1983) 112:284-289; Tilburn et al., *Gene* (1983) 26:205-221, Yelton et al., *Proc. Natl. Acad. Sci. (USA)* (1984) 81:1470-1474, Kelly and Hynes, *EMBO J.* (1985) 4:475479; EP 0 244,234, and WO 91/00357.

Insect Cells. Expression of heterologous genes in insects is accomplished as described in U.S. Pat. No. 4,745,051, Friesen et al. (1986) "The Regulation of Baculovirus Gene Expression" in: The Molecular Biology Of Baculoviruses (W. Doerfler, ed.), EP 0 127,839, EP 0 155,476, and Vlak et al., J. Gen. Virol. (1988) 69:765-776, Miller et al., *Ann. Rev. Microbiol.* (1988) 42:177, Carbonell et al., *Gene* (1988) 73:409, Maeda et al., *Nature* (1985) 315:592-594, Lebacq-Verheyden et al., *Mol. Cell. Biol.* (1988) 8:3129; Smith et al., *Proc. Natl. Acad. Sci. (USA)* (1985) 82:8404, Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., Generic Engineering (Setlow, J. K. et al. eds.), Vol. 8 (Plenum Publishing, 1986), pp. 277-279, and Maeda et al., *Nature*, (1985) 315:592-594.

Mammalian Cells. Mammalian expression is accomplished as described in Dijkema et al., *EMBO J.* (1985) 4:761, Gorman et al., *Proc. Natl. Acad. Sci. (USA)* (1982) 79:6777, Boshart et al., *Cell* (1985) 41:521 and U.S. Pat. No. 4,399, 216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. Pat. No. RE 30,985.

Screening Assays to Identify Chemotherapeutic Agents

The invention also encompasses screening assays to identify agents that modulate TTK activity, specifically that decrease aberrant TTK activity in an affected cell, e.g., a cancerous or pre-cancerous cell in which TTK is differentially expressed. Such assays may be performed either in vitro or in vivo.

Candidate Agents

The term "agent" as used herein describes any molecule with the capability of altering the expression or physiological function of a gene product of a differentially expressed gene. Generally a plurality of assay mixtures are run in parallel with different agent concentrations to obtain a differential response to the various concentrations. Typically, one of these concentrations serves as a negative control, ie., at zero concentration or below the level of detection.

Candidate agents encompass numerous chemical classes, including, but not limited to, organic molecules (e.g., small organic compounds having a molecular weight of more than 50 and less than about 2,500 daltons), peptides, monoclonal antibodies, antisense polynucleotides, and ribozymes, and the like. Candidate agents can comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: polynucleotides, peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known phannacological agents may be subjected to directed or random chemical modifications, such as acylation, alkylation, esterification, amidification, etc. to produce structural analogs. Candidate agents can be assessed for modulation of TTK activity either singly or in pools.

Screening of Candidate Agents In Vitro

A wide variety of in vitro assays may be used to screen candidate agents for the desired biological activity, including, but not limited to, labeled in vitro protein-protein binding assays, protein-DNA binding assays (e.g., to identify agents that affect expression), electrophoretic mobility shift assays, immunoassays for protein binding, and the like. For example, by providing for the production of large amounts of a differentially expressed polypeptide, one can identify ligands or substrates that bind to, modulate or mimic the action of the polypeptide. Further methods for identifying these ligands and substrates are provided below. The purified polypeptide may also be used for determination of three-dimensional crystal structure, which can be used for modeling intermolecular interactions, transcriptional regulation, etc.

The screening assay can be a binding assay, wherein one or more of the molecules may be joined to a label, and the label directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g., albumin, detergents, etc that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Many mammalian genes have homologs in yeast and lower animals. The study of such homologs physiological role and interactions with other proteins in vivo or in vitro can facilitate understanding of biological function. In addition to model systems based on genetic complementation, yeast has been shown to be a powerful tool for studying protein-protein interactions through the two hybrid system described in Chien et al. 1991 *Proc. Natl. Acad. Sci. USA* 88:9578-9582.

Screening of Candidate Agents In Vivo

Candidate agents can be screened in a non-human animal model of cancer (e.g., in animals into which have been injected cancerous cells; in animals that are transgenic for an alteration in expression of a differentially expressed gene as described herein, e.g., a transgenic "knock-out," or a transgenic "knock-in," a polynucleotide encoding all or a portion of a differentially expressed gene product and comprising an operably linked reporter gene, and the like).

In general, the candidate agent is administered to the animal, and the effects of the candidate agent determined. The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent hat approaches an upper limit of the amount that can be delivered successfully to the animal), and may include delivery of the agent in different formulation. The agents can be administered singly or can be combined in combinations of two or more, especially where administration of a combination of agents may result in a synergistic effect.

The effect of agent administration upon the transgenic animal can be monitored by assessing expression of the gene product, growth of the injected tumor cells, and the like.

Identified Candidate Agents

Compounds having the desired pharmacological activity may be administered in a physiologically acceptable carrier to a host for treatment of a condition that is amenable to treatment by modulation of expression of a differentially expressed gene product. The therapeutic agents may be administered in a variety of ways, orally, topically, parenterally e.g.,subcutaneously, intraperitoneally, by viral infection, intravascularly, etc. Oral and inhaled treatments are of particular interest. Depending upon the manner of introduction, the compounds may be formulated in a variety of ways. The concentration of therapeutically active compound in the formulation may vary from about 0.1-100 wt. %. The therapeutic agents can be administered in a single dose, or as multiple doses over a course of treatment.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Methods of Screening for Drugs that Modulate TTK Activity

A TTK polypeptide or TTK-encoding nucleic acid according to the present invention may be used in screening for molecules which affect or modulate TTK activity or function. Such molecules may be useful in a therapeutic and/or prophylactic context. Means for screening for substances potentially useful in treating or preventing cancer is provided by the present invention. In general, the methods of the invention are to facilitate identification of modulators of TTK activity (e.g., by modulating activity of TTK polypeptide or other TTK gene product, or by affecting TTK activity by targeting activity of gene products that act either upstream or downstream of TTK in a cascade that leads to TTK activity), with agents that decrease TTK activity generally being of particular interest. Substances identified as modulators of the TTK activity represent an advance in the fight against cancer since they provide basis for design and investigation of pharmaceuticals for in vivo use.

A method of screening for a substance which modulates activity of a polypeptide may include contacting one or more test substances with the polypeptide in a suitable reaction medium, testing the activity of the treated polypeptide (e.g., the ability to phosphorylate its substrate) and comparing that activity with the activity of the polypeptide in comparable reaction medium untreated with the test substance or substances. A difference in activity between the treated and untreated polypeptides is indicative of a modulating effect of the relevant test substance or substances.

Combinatorial library technology provides an efficient way of testing a potentially vast number of different substances for ability to modulate activity of a polypeptide. Such libraries and their use are known in the art. The use of peptide libraries is preferred. Test substances may also be screened for ability to interact with the polypeptide, e.g., in a yeast two-hybrid system. This may be used as a coarse screen prior to testing a substance for actual ability to modulate activity of the polypeptide. Alternatively, the screen could be used to screen test substances for binding to a TTK specific binding partner.

A substance identified using as a modulator of TTK polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

TTK Activity Assays

The activity of the TTK may be measured using any suitable kinase assay known in the art. For example, and not by way of limitation, the methods described in Hogg et al (Oncogene 1994 9:98-96), Mills et al (J. Biol. Chem. 1992 267: 16000-006) and Tomizawa et al 2001 (FEBS Lett. 2001 492:

221-7), Schmandt et al, (J. Immunol. 1994, 152:96-105) may be used. Further serine, threonine and tyrosine kinase assays are described in Ausubel et al. (Short Protocols in Molecular Biology, 1999, unit 17.6).

TTK assays generally use TTK polypeptide, a labeled donor substrate, and a receptor substrate that is either specific or non-specific for TTK. In such assays TTK transfers a labeled moiety from the donor substrate to the receptor substrate, and kinase activity is measured by the amount of labeled moiety transferred from the donor substrate to the receptor substrate.

TTK polypeptide may be produced using various expression systems as detailed above, may be purified from cells, may be in the form of a cleaved or uncleaved recombinant fusion protein and may have non-TTK polypeptide sequences, for example a His tag or β-galactosidase at its N- or C-terminus. TTK activity may be assayed in cancerous cells lines if the cancerous cell lines are used as a source of the TTK to be assayed. Suitable donor substrates for TTK assays include any molecule that is susceptible to dephosphorylation by TTK include γ-labeled ATP and ATP analogs, wherein the label is $^{33}P$, $^{32}P$, $^{35}S$ or any other radioactive isotope or a suitable fluorescent marker. Suitable recipient substrates for TTK assays include any polypeptide or other molecule that is susceptible to phosphorylation by TTK. Recipient substrates are usually derived from fragments of in vivo targets of TTK. Recipient substrates fragments may be 8 to 50 amino acids in length, usually 10 to 30 amino acids and preferably of about 10, 12, 15, 18, 20 and 25 amino acids in length Further recipient substrates can be determined empirically using a set of different polypeptides or other molecules. Targets of TTK suitable for TTK assays include tau and cdc25. Recipient substrates for TTK are typically capable of being purified from other components of the reaction once the reaction has been performed. This purification is usually done through a molecular interaction, where the recipient substrates is biotinylated and purified through its interaction with streptavidin, or a specific antibody is available that can specifically recognize the recipient substrates. The reaction can be performed in a variety of conditions, such as on a solid support, in a gel, in solution or in living cells.

One exemplary recipient substrate for TTK phosphorylation is the human protein cdc25, SEQ ID NO:26, which is phosphorylated by TTK at the serine residues of amino acid position 214 and 216. Two fragments of cdc25 are used as substrates in the kinase assay described below. These fragments comprise peptides A (SEQ ID NO:27), corresponding to amino acids 209 to 225 of the cdc25 polypeptide sequence or peptide B (SEQ ID NO:28), corresponds to amino acids 210 to 223 of the cdc25 polypeptide. In this assay, two biotinylated polypeptides of comprising either SEQ ID NO:27 (Biotin-SGSGSGLYRSPSMPENLNRPR-NH2) or SEQ ID NO:28 (Biotin-GGGGLYRSPSMPENLNRK-OH) are used.

The choice of detection methods depends on type of label used for the donor molecule and may include, for example, measurement of incorporated radiation or fluorescence by autoradiography, scintillation, scanning or fluorography.

Methods of Inhibiting Tumor Growth and Other Treatment Goals

The invention further provides methods for reducing growth of cancer cells, particular breast or colon cancer cells. In general, the methods comprise contacting a cancer cell that expresses TTK at an aberrant level relative to normal cells with a substance that (1) modulates, generally decreases, expression of TTK (e.g., a antisense polynucleotide corresponding to TTK); or (2) otherwise modulates, generally decreases, TM polypeptide levels and/or TTK activity in a cancerous cell having aberrant TTK activity.

"Reducing growth of a cancer cell" includes, but is not limited to, reducing proliferation of cancer cells, and reducing the incidence of a normal cell from developing a cancerous phenotype or morphology. Whether a reduction in cancer cell growth has been achieved can be readily determined using any known assay, including, but not limited to, [$^3$H]-thymidine incorporation; counting cell number over a period of time; detecting, measuring a marker associated with colon cancer (e.g., CEA, CA19-9, and LASA), and/or methods well known in the art for assessing tumor burden.

The present invention provides methods for treating cancer (particularly breast and colon cancer or other cancer that is associated with aberrantly high TTK activity) which methods generally comprise administering to an individual an agent that reduces TTK activity in an amount sufficient to reduce cancer cell growth to treat the cancer. Whether a substance, or a specific amount of the substance, is effective in treating cancer can be assessed using any of a variety of known diagnostic assays, e.g., in the case of colon cancer, sigmoidoscopy, proctoscopy, rectal examination, colonoscopy with biopsy, contrast radiographic studies, CAT scans, angiography, and detection of a tumor marker associated with colon cancer in the blood of the individual. The substance can be administered systemically or locally. Thus, in some embodiments, the substance is administered locally, and colon cancer growth is decreased at the site of administration. Local administration may be useful in treating, e.g., a solid tumor.

In one embodiment, the invention features polynucleotides that act as antisense polynucleotides and decrease TTK activity. Antisense TTK polynucleotides generally comprise a polynucleotide of at least about 20 to 3000 nucleotides, usually at least about 20 to 1000 nucleotides and more usually at least about 8 to 50 nucleotides, and preferably about 26, 20, 18, 17, 15, 10 and 8 nucleotides. Exemplary TTK polynucleotides are provided in the Examples and in SEQ ID NO:1-12, although any antisense fragment of SEQ ID NO:13 will suffice.

The therapeutic regimen is selected according to the expression profile. For example, if a patient's tumor indicates that the tumor produces aberrantly high level of TTK relative to normal cells, then a drug having efficacy in the treatment of such TTK-expressing tumors is selected for therapy of that patient.

Pharmaceutical Compositions

Pharmaceutical compositions of the invention can comprise a therapeutically effective amount of a polypeptide, antibody, polynucleotide (including antisense nucleotides and ribozymes), or small molecule or other compound identified as modulating activity of TTK, preferably decreasing TTK activity. The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature, and/or in the effect upon tumor load in the subject (e.g., decrease in tumor size or inhibition in tumor growth). The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation is determined by routine experimentation and is within the judgment of the clinician. For purposes of the present invention, an effective dose will generally be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., N.J. 1991). The precise nature of the carrier or other material may depend on the route of administration, e.g., oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is has suitable pH, isotonicity and stability. Suitable solutions, for example, optionally include but are not limited to isotonic vehicles such as sodium chloride, preservatives, stabilizers, buffers, antioxidants and/or other additives as required.

Administration of the pharmaceutical is administered in a prophylactically effective amount or a therapeutically effective amount. The actual amount administered, and rate and time-course of administration, will depend on the nature and severity of what is being treated. Decisions on dosage etc, can be determined by one skilled in the art based upon the disclosed methods, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells. Targeting can be accomplished by, for example, administering a drug-antibody complex to a subject, wherein the antibody is specific for a cancer-associated antigen, and the drug is one that reduces cancer cell growth. Targeting can be accomplished by coupling (e.g., linking, directly or via a linker molecule, either covalently or non-covalently, so as to form a drug-antibody complex) a drug to an antibody specific for a cancer-associated antigen. Methods of coupling a drug to an antibody are well known in the art and need not be elaborated upon herein.

Pharmaceutical agents can also be produced in the target cells by expression from an encoding gene introduced into the cells, e.g., in a viral or liposomal vector. The vector could be targeted to the specific cells to be treated, or it could contain regulatory elements which are switched on more or less selectively by the target cells.

Alternatively, the agent could be administered in a precursor form, for conversion to the active form by an activating agent produced in, or targeted to, the cells to be treated. A composition may be administered alone or in combination with other treatments, either simultaneously or sequentially dependent upon the condition to be treated.

Delivery Methods for Therapy

Once formulated, the compositions of the invention or identified using the methods of the invention can be administered directly to the subject (e.g., as polynucleotide or polypeptides). Direct delivery of the compositions will generally be accomplished by parenteral injection, e.g., subcutaneously, intraperitoneally, intravenously or intramuscularly, intratumoral or to the interstitial space of a tissue. Other modes of administration include oral and pulmonary administration, suppositories, and transdermal applications, needles, and gene guns or hyposprays. Dosage treatment can be a single dose schedule or a multiple dose schedule.

Once a gene corresponding to a polynucleotide of the invention has been found to correlate with a proliferative disorder, such as neoplasia, dysplasia, and hyperplasia, the disorder can be amenable to treatment by administration of a therapeutic agent based on the provided polynucleotide, corresponding polypeptide or other corresponding molecule (e.g., antisense, ribozyme, etc.).

The dose and the means of administration are determined based on the specific qualities of the therapeutic composition, the condition, age, and weight of the patient, the progression of the disease, and other relevant factors. For example, administration of polynucleotide therapeutic compositions agents of the invention includes local or systemic administration, including injection, oral administration, particle gun or catheterized administration, and topical administration. Preferably, the therapeutic polynucleotide composition contains an expression construct comprising a promoter operably linked to a polynucleotide of at least 12, 15, 17, 18, 22, 25, 30, or 35 contiguous -nucleotides of the polynucleotide disclosed herein. Various methods can be used to administer the therapeutic composition directly to a specific site in the body. For example, a small metastatic lesion is located and the therapeutic composition injected several times in several different locations within the body of tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. The antisense composition is directly administered to the surface of the tumor, for example, by topical application of the composition. X-ray imaging is used to assist in certain of the above delivery methods.

Receptor-mediated targeted delivery of therapeutic compositions containing an antisense polynucleotide, subgenomic polynucleotides, or antibodies to specific tissues can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J Biol. Chem.* (1994) 269:542; Zenke et al., *Proc. Natl. Acad. Sci.* (*USA*) (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. Factors such as method of action (e.g., for enhancing or inhibiting levels of the encoded gene product) and efficacy of transformation and expression are considerations which will affect the dosage required for ultimate efficacy of the antisense subgenomic polynucleotides. Where greater expression is desired over a larger area of tissue, larger amounts of antisense subgenomic polynucleotides or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect. For polynucleotide related genes encoding polypeptides or proteins with anti-inflammatory activity, suitable use, doses, and administration are described in U.S. Pat. No. 5,654,173.

The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., WO 90/07936; WO 94/03622; WO 93/25698; WO 93/25234; U.S. Pat. No. 5, 219,740; WO 93/11230; WO 93/10218; U.S. Pat. No. 4,777, 127; GB Patent No. 2,200,651; EP 0 345 242; and WO 91/02805), alphavirus-based vectors.(e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA(see, e.g., Wu, *J. Biol. Chem.* (1989) 264:16985); eukaryotic cell delivery vehicles cells (see, e.g., U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes that can act as gene delivery vehicles are described in U.S. Pat. No. 5,422,120; WO 95/13796; WO 94/23697; WO 91/14445; and EP 0524968. Additional approaches are described in Philip, *Mol. Cell Biol.* (1994) 14:2411, and in Woffendin, *Proc. Natl. Acad. Sci.* (1994) 91:1581.

Further non-viral delivery suitable for use includes mechanical delivery systems such as the approach described in Woffendin et al., *Proc. Natl. Acad. Sci. USA* (1994) 91(24): 11581. Moreover, the coding sequence and the product of expression of such can be delivered through deposition of photopolymerized hydrogel materials or use of ionizing radiation (see, e.g., U.S. Pat. No. 5,206,152 and WO 92/11033). Other conventional methods for gene delivery that can be used for delivery of the coding sequence include, for example, use of hand-held gene transfer particle gun (see, e.g., U.S. Pat. No. 5,149,655); use of ionizing radiation for activating transferred gene (see, e.g., U.S. Pat. No. 5,206,152 and WO 92/11033).

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer. Gene transfer techniques which selectively target the TTK nucleic acid to the affected cell type are preferred. Examples of this included receptor-mediated gene transfer, in which the nucleic acid is linked to a protein ligand via polylysine, with the ligand being specific for a receptor present on the surface of the target cells.

Screening for Substances Affecting TTK Expression

The present invention also provides the use of all or part of the nucleic acid sequence of the TTK promoter and/or enhancer regions in methods of screening for substances which modulate the activity of the promoter and increase or decrease the level of TTK expression. This assay can be performed to identify anti-cancer agents for therapeutic and/or prophylactic purposes. The level of promoter activity, i.e., the ability to initiate transcription, is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridize with the mRNA and which are labeled or may be used in a specific amplification reaction such as PCR. Use of a reporter gene facilitates determination of promoter activity by reference to protein production.

Generally, a reporter gene under control of the TTK promoter and/or enhancers may be transcribed into mRNA which may be translated into a peptide or polypeptide product which may be detected and preferably quantitated following expression. The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue color on substrate, the assay being by eye or by use of a spectrophotometer to measure absorbance. Fluorescence, for example that produced as a result of luciferase activity, may be quantitated using a spectrophotometer. Radioactive assays may be used, for instance using choloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labeled directly or indirectly using any standard technique.

Those skilled in the art are well aware of a multitude of possible reporter genes and assay techniques which may be used to determine gene activity according to the presently disclosed methods. Any suitable reporter/assay may be used and the present invention is intended to encompass such systems.

Following identification of a substance which modulates or affects promoter activity, the substance may be investigated further. Furthermore, it may be manufactured and/or used in preparation, i.e. manufacture or formulation, of a composition such as a medicament, pharmaceutical composition or drug.

Integrated Disease Information System

The levels of TTK in a sample can be used in an integrated disease information system to aid in analysis such as proposed patient interventions, designing clinical trials, performing pharmacoeconomic analysis, and illustrating disease progression for various patients over time. For example, TTK information determined according to the methods of the invention can be used in a system such as that described in U.S. Pat. No. 6,108,635 issued to Herren, et al. on Aug. 22, 2000. Such a system can be for collecting the results of medical treatments given to patients in a plurality of locations. See, e.g, U.S. Pat. No. 5,713,350 issued to Yokota, et al. on Feb. 3, 1998.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Source of Patient Tissue Samples

Normal and cancerous tissues were collected from patients using laser capture microdissection (LCM) techniques, which techniques are well known in the art (see, e.g., Ohyama et al. (2000) *Biotechniques* 29:530-6; Curran et al. (2000) *Mol. Pathol.* 53:64-8; Suarez-Quian et al. (1999) *Biotechniques* 26:328-35; Simone et al. (1998) *Trends Genet* 14:272-6; Conia et al. (1997) *J. Clin. Lab. Anal.* 11:28-38; Emmert-Buck et al. (1996) *Science* 274:998-1001). Adenoma was not described in any of the patients; adenoma dysplasia (described as hyperplasia by the pathologist) was described in Patient ID No. 695. Extranodal extensions were described in two patients, Patient ID Nos. 784 and 791. Lymphovascular invasion was described in seven patients, Patient ID Nos. 128, 278, 517, 534, 784, 786, and 791.. Crohn's-like infiltrates were described in seven patients, Patient ID Nos. 52, 264, 268, 392, 393, 784, and 791.

Example 2

Differential Expression of TTK cDNA probes were prepared from total RNA isolated from the patient cells described in Example 1. Since LCM provides for the isolation of specific cell types to provide a substantially homogenous cell sample, this provided for a similarly pure RNA sample.

Total RNA was first reverse transcribed into cDNA using a primer containing a T7 RNA polymerase promoter, followed by second strand DNA synthesis. cDNA was then transcribed in vitro to produce antisense RNA using the T7 promoter-mediated expression (see, e.g., Luo et al. (1999) *Nature Med* 5:117-122), and the antisense RNA was then converted into cDNA. The second set of cDNAs were again transcribed in vitro, using the T7 promoter, to provide antisense RNA. Optionally, the RNA was again converted into cDNA, allowing for up to a third round of T7-mediated amplification to produce more antisense RNA. Thus the procedure provided for two or three rounds of in vitro transcription to produce the final RNA used for fluorescent labeling. Fluorescent probes were generated by first adding control RNA to the antisense RNA mix, and producing fluorescently labeled cDNA from the RNA starting material. Fluorescently labeled cDNAs prepared from the tumor RNA sample were compared to fluorescently labeled cDNAs prepared from normal cell RNA sample. For example, the cDNA probes from the normal cells were labeled with Cy3 fluorescent dye (green) and the cDNA probes prepared from the tumor cells were labeled with Cy5 fluorescent dye (red).

Each array used had an identical spatial layout and control spot set. Each microarray was divided into two areas, each area having an array with, on each half, twelve groupings of 32×12 spots for a total of about 9,216 spots on each array. The two areas are spotted identically which provide for at least two duplicates of each clone per array. Spotting was accomplished using PCR amplified products from 0.5 kb to 2.0 kb and spotted using a Molecular Dynamics Gen III spotter according to the manufacturer's recommendations. The first row of each of the 24 regions on the array had about 32 control spots, including 4 negative control spots and 8 test polynucleotides. The test polynucleotides were spiked into each sample before the labeling reaction with a range of concentrations from 2-600 pg/slide and ratios of 1:1. For each array design, two slides were hybridized with the test samples reverse-labeled in the labeling reaction. This provided for about 4 duplicate measurements for each clone, two of one color and two of the other, for each sample.

The differential expression assay was performed by mixing equal amounts of probes from tumor cells and normal cells of the same patient. The arrays were prehybridized by incubation for about 2 hrs at 60° C. in 5×SSC/0.2% SDS/1 mM EDTA, and then washed three times in water and twice in isopropanol. Following prehybridization of the array, the probe mixture was then hybridized to the array under conditions of high stringency (overnight at 42° C. in 50% formamide, 5×SSC, and 0.2% SDS. After hybridization, the array was washed at 55° C. three times as follows: 1) first wash in 1×SSC/0.2% SDS; 2) second wash in 0.1×SSC/0.2% SDS; and 3) third wash in 0.1×SSC.

The arrays were then scanned for green and red fluorescence using a Molecular Dynamics Generation III dual color laser-scanner/detector. The images were processed using BioDiscovery Autogene software, and the data from each scan set normalized to provide for a ratio of expression relative to normal. Data from the microarray experiments was analyzed according to the algorithms described in U.S. application Ser. No. 60/252,358, filed Nov. 20, 2000, by E. J. Moler, M. A. Boyle, and F. M. Randazzo, and entitled "Precision and accuracy in cDNA microarray data," which application is specifically incorporated herein by reference.

The experiment was repeated, this time labeling the two probes with the opposite color in order to perform the assay in both "color directions." Each experiment was sometimes repeated with two more slides (one in each color direction). The level fluorescence for each sequence on the array expressed as a ratio of the geometric mean of 8 replicate spots/genes from the four arrays or 4 replicate spots/gene from 2 arrays or some other permutation. The data were normalized using the spiked positive controls present in each duplicated area, and the precision of this normalization was included in the final determination of the significance of each differential. The fluorescent intensity of each spot was also compared to the negative controls in each duplicated area to determine which spots have detected significant expression levels in each sample.

A statistical analysis of the fluorescent intensities was applied to each set of duplicate spots to assess the precision and significance of each differential measurement, resulting in a p-value testing the null hypothesis that there is no differential in the expression level between the tumor and normal samples of each patient. During initial analysis of the microarrays, the hypothesis was accepted if $p>10^{-3}$, and the differential ratio was set to 1.000 for those spots. All other spots have a significant difference in expression between the tumor and normal sample. If the tumor sample has detectable expression and the normal does not, the ratio is truncated at 1000 since the value for expression in the normal sample would be zero, and the ratio would not be a mathematically useful value (e.g., infinity). If the normal sample has detectable expression and the tumor does not, the ratio is truncated to 0.001, since the value for expression in the tumor sample would be zero and the ratio would not be a mathematically useful value. These latter two situations are referred to herein as "on/off." Database tables were populated using a 95% confidence level (p>0.05).

The difference in the expression level of TTK in the colon tumor cells relative to the matched normal colon cells was greater than or equal to 2 fold (">=2×") in 39% of the patients, greater than or equal to 2.5 fold in 36% of the patients, and greater than or equal to 5 fold in 27% of the patients examined.

Figure 2:
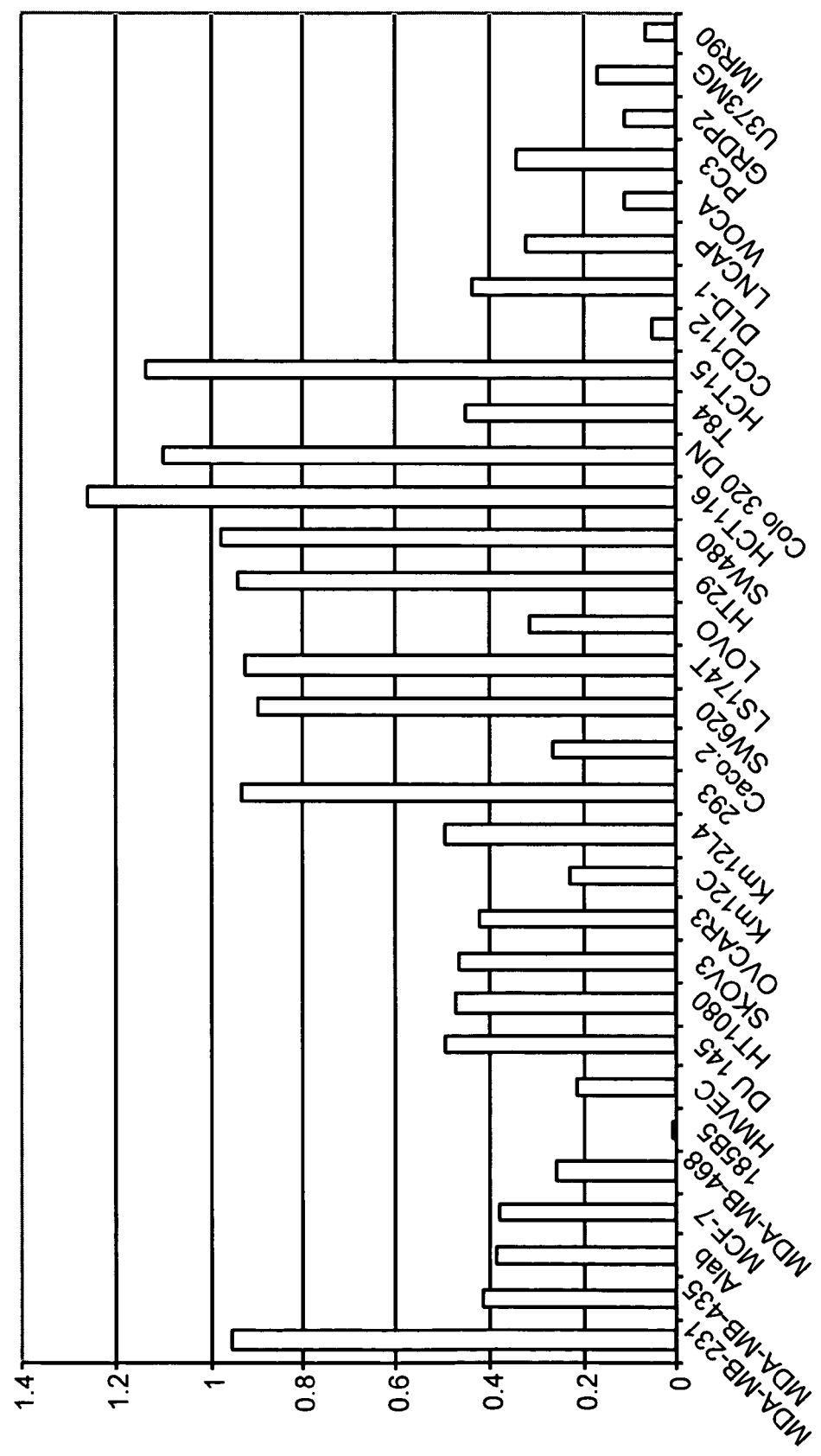
FIG. 2 is a bar graph illustrating expression of TTK in various tumor cell lines as detected by PCR.
Figure 3:
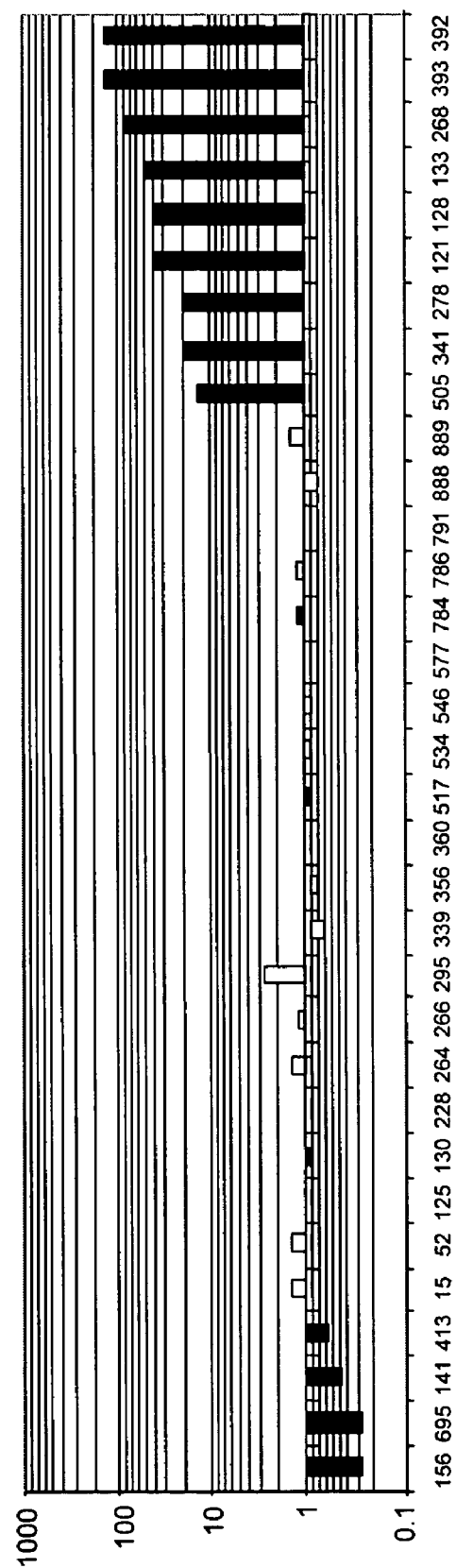
FIGS. 3-6 are graphs illustrating expression profiles for IGF2, MAPKAPK2, TTK, and MARCKS in patients with colorectal carcinoma.
Figure 4:
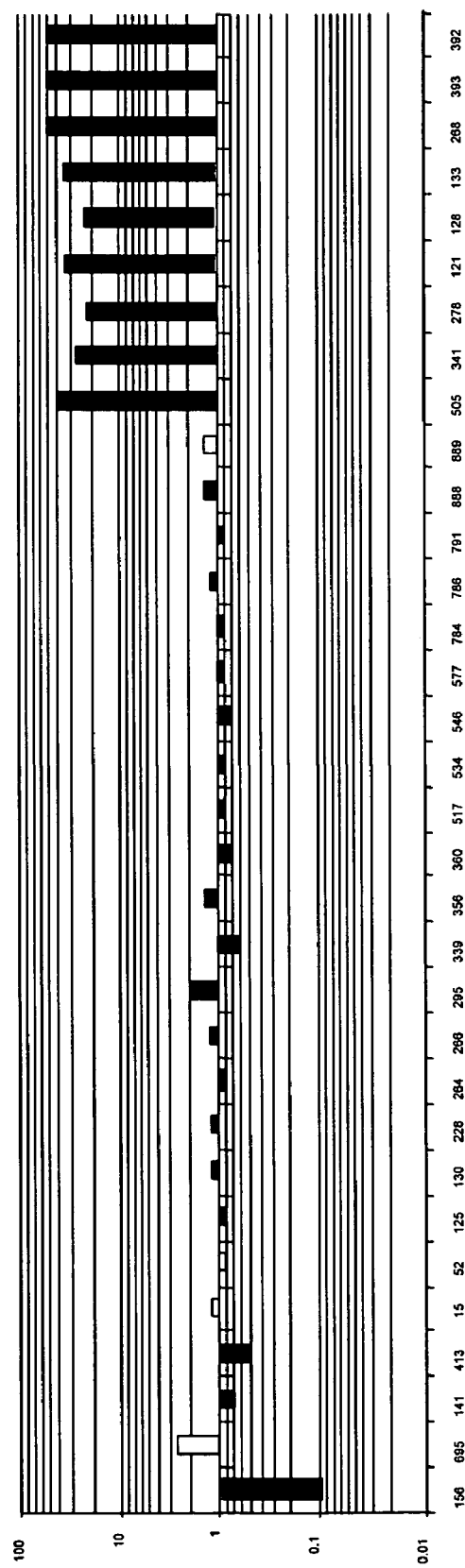
Figure 5:
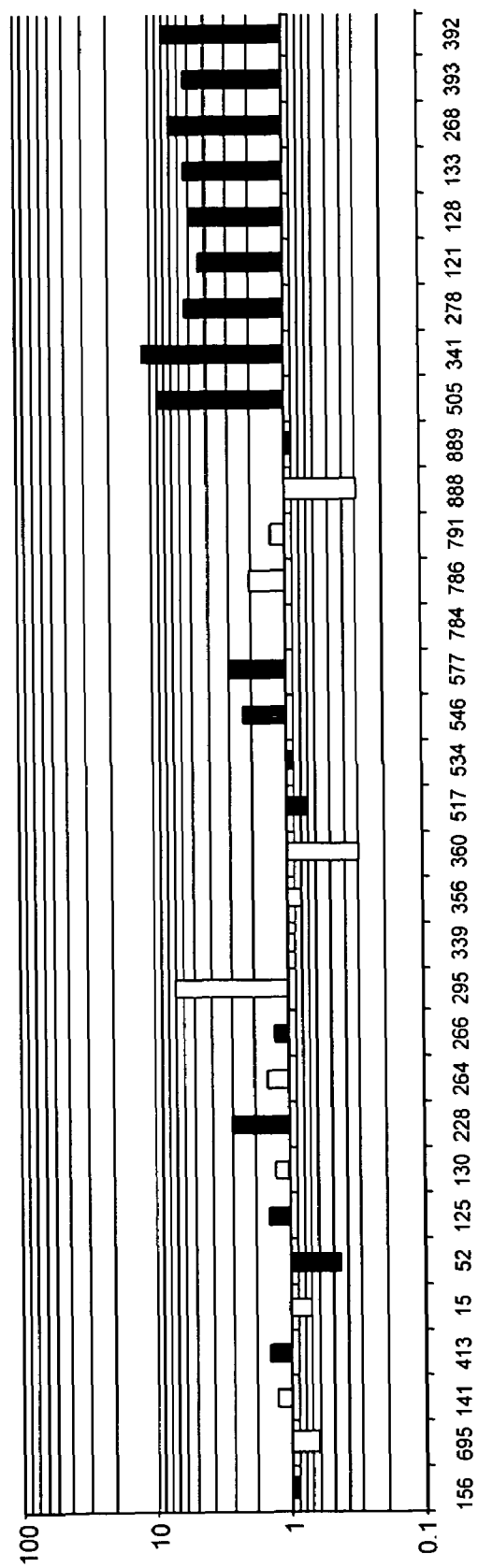
Figure 6:
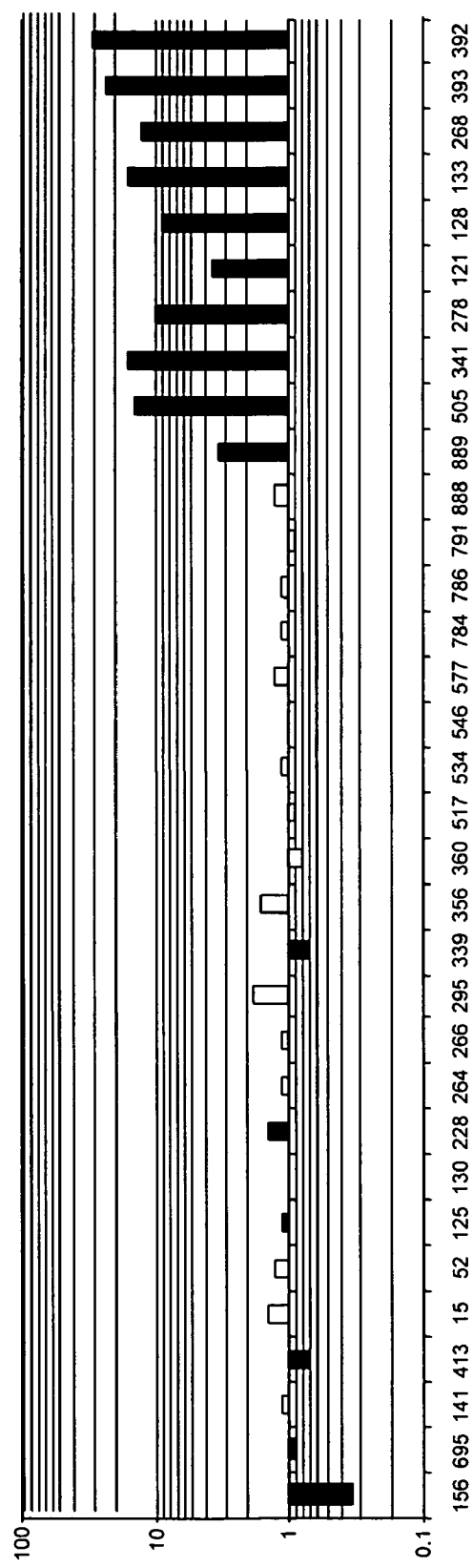

Quantitative PCR of a number of normal tissues and tumor cell lines, particularly colorectal carcinoma cell lines was used to analyze expression of TTK. Quantitative real-time PCR was performed by first isolating RNA from cells using a Roche RNA Isolation kit according to manufacturer's directions. One microgram of RNA was used to synthesize a first-strand cDNA using MMLV reverse transcriptase (Ambion) using the manufacturers buffer and recommended concentrations of oligo dT, nucleotides, and Rnasin. This first-strand cDNA served as a template for quantitative real-time PCR using the Roche light-cycler as recommended in the machine manual. TTK was amplified with the forward primer CGGAATCAAGTCTTCTAGCT (SEQ ID NO:1) and reverse primer GGTTGCTCAAAAGTTGGTATG (SEQ ID NO:2) PCR product was quantified based on the cycle at which the amplification entered the linear phase of amplification in comparison to an internal standard and using the software supplied by the manufacturer. Small differences in amounts or total template in the first-strand cDNA reaction were eliminated by normalizing to amount of actin amplified in a separate quantitative PCR reaction using the forward primer 5'-CGGGAAATCGTGCGTGACATTAAG-3' (SEQ ID NO:3) and the reverse primer: 5'-TGATCTCCTTCTG-CATCCTGTCGG-3' (SEQ ID NO:4). The results for TTK mRNA levels in normal tissues are shown in FIG. 1; the results for TTK mRNA levels in tumor cell lines are shown in FIG. 2. A brief description of the cell lines analyzed is provided in the Table A below.

TABLE A

| Cell Line | Tissue Source |
|---|---|
| MDA-MB-231 | Human breast; high metastatic potential (micromets in lung; adenocarcinoma; pleural effusion |
| MDA-MB-435 | Human breast, high metastatic potential (macrometastases in lung) |
| MCF-7 | Human breast; non-metastatic |
| MDA-MB-468 | Human breast; adenocarcinoma |
| Alab | Human breast, metastatic |
| SKOV3 | Human ovarian adenocarcinoma |
| OVCAR3 | Human ovarian adenocarcinoma |
| KM12C | Human colon; low metastatic potential |
| KM12L4 | Human colon; high metastatic potential (derived from Km12C) |
| DU 145 | Human prostate; carcinoma; from metastatic site: brain |
| HT1080 | Human sarcoma cell line; |
| HMVEC | Primary human microvascular endothelial cells |
| 184B5 | normal breast epithelial cells; chemically transformed |
| LNCAP | prostate carcinoma; metastasis to left supraclavicular lymph |
| U373MG | glioblastoma cell |
| WOCA | primary prostate epithelium |
| Caco-2 | Human colorectal adenocarcinoma |
| SW620 | Human colorectal adenocarcinoma; from metastatic site (lymph node) |
| LS174T | High metastatic potential human colorectal adenocarcinoma |
| LOVO | Human colorectal adenocarcinoma; colon; from metastatic site (colon) |
| HT29 | Human colorectal adenocarcinoma; colon |
| SW480 | Human colorectal adenocarcinoma; colon |
| HCT116 | Human colorectal carcinoma; colon |
| Colo 320DN | Human colorectal adenocarcinoma; colon |
| T84 | Human colorectal carcinoma; colon; from metastatic site (lung) |

TABLE A-continued

| Cell Line | Tissue Source |
|---|---|
| HCT15 | Human colorectal adenocarcinoma; colon |
| CCD112 | Human colorectal adenocarcinoma, low metastatic potential |
| DLD1 | Human colon; colorectal adenocarcinoma |
| 293 | kidney epithelial cells |
| GRDP2 | primary prostate epithelium |
| IMR90 | primary lung fibroblast |
| PC3 | prostate cancer; androgen receptor negative |

TTK was expressed in normal cells (FIG. 1), with thymus and testis identified as the normal tissues that most highly express the gene for TTK. Numerous cancer cells, however, displayed a significantly elevated level of TTK expression (FIG. 2) as compared to most wild-type tissues.

Example 3

Hierarchical Clustering and Stratification of Colon Cancer Using Differential Expression Data Differential expression patterns from Example 2 were analyzed by applying hierarchical clustering methods to the data sets (see Eisen et al. (1998) *PNAS* 95:14863-14868). In short, hierarchical clustering algorithms are based on the average-linkage method of Sokal and Michener (Sokal, R R & Michener, C D (1958) Univ. Kans. Sci. Bull. 38, 1409-1438), which was developed for clustering correlation matrixes. The object of this algorithm is to compute a dendrogram that assembles all elements into a single tree. For any set of n genes, an upper-diagonal similarity matrix is computed which contains similarity scores for all pairs of genes. The matrix is scanned to identify the highest value (representing a similar pair of genes). Using this technique, four groups of differential expression patterns were identified and assigned to clusters.

Application of hierarchical clustering to the data from Example 2 revealed that IGF2 (insulin-like growth factor 2), TTK (serine, threonine, tyrosine kinase implicated in the cell cycle), MAPKAPK2 (mitogen-activated protein (MAP) kinase-activated protein kinase), and MARCKS (myristoylated alanine-rich C kinase substrate, which is a substrate of protein kinase C) are concurrently upregulated as detected in 9 out of the 33 colon cancer patient samples examined. The data for these experiments is presented in graphical form in FIGS. 3-6. The concurrent upregulation suggests that these genes are co-regulated and that patients with an elevated serum level of IGF2 may be candidates for treatment with inhibitors to TTK, MAPKAP kinase 2, MARCKS and/or IGF2.

Example 4

Antisense Regulation of TTK Expression

Additional functional information on TTK was generated using antisense knockout technology. TTK expression in cancerous cells was further analyzed to confirm the role and function of the gene product in tumorgenesis, e.g., in promoting a metastatic phenotype.

A number of different oligonucleotides complementary to TTK mRNA were designed as potential antisense oligonucleotides, and tested for their ability to suppress expression of TTK. The ability of each designed antisense oligonucleotide to inhibit gene expression was tested through transfection into SW620 colon colorectal carcinoma cells. For each transfection mixture, a carrier molecule, preferably a lipitoid or cholesteroid, was prepared to a working concentration of 0.5 mM in water, sonicated to yield a uniform solution, and filtered through a 0.45 µm PVDF membrane. The antisense or control oligonucleotide was then prepared to a working concentration of 100 µM in sterile Millipore water. The oligonucleotide was further diluted in OptiMEM™ (Gibco/BRL), in a microfige tube, to 2 µM, or approximately 20 µg oligo/ml of OptiMEM™. In a separate microfuge tube, lipitoid or cholesteroid, typically in the amount of about 1.5-2 nunol lipitoid/µg antisense oligonucleotide, was diluted into the same volume of OptiMEM™ used to dilute the oligonucleotide. The diluted antisense oligonucleotide was immediately added to the diluted lipitoid and mixed by pipetting up and down. Oligonucleotide was added to the cells to a final concentration of 30 nM.

The level of target mRNA (TTK) in the transfected cells was quantitated in the cancer cell lines using the Roche LightCycler™ real-time PCR machine. Values for the target mRNA were normalized versus an internal control (e.g., beta-actin). For each 20 µl reaction, extracted RNA (generally 0.2-1 µg total) was placed into a sterile 0.5 or 1.5 ml microcentrifuge tube, and water was added to a total volume of 12.5 µl. To each tube was added 7.5 µl of a buffer/enzyme mixture, prepared by mixing (in the order listed) 2.5 µl $H_2O$, 2.0 µl 10×reaction buffer, 10 µl oligo dT (20 pmol), 1.0 µl dNTP mix (10 mM each), 0.5 µl RNAsin® (20 u) (Ambion, Inc., Hialeah, Fla.), and 0.5 µl MMLV reverse transcriptase (50 u) (Ambion, Inc.). The contents were mixed by pipetting up and down, and the reaction mixture was incubated at 42° C. for 1 hour. The contents of each tube were centrifuged prior to amplification.

An amplification mixture was prepared by mixing in the following order: 1×PCR buffer II, 3 mM $MgCl_2$, 140 µM each dNTP, 0.175 pmol each oligo, 1:50,000 dil of_SYBR® Green, 0.25 mg/ml BSA, 1 unit Taq polymerase, and $H_2O$ to 20 µl. (PCR buffer II is available in 10×concentration from Perkin-Elmer, Norwalk, Conn.). In 1X concentration it contains 10 mM Tris pH 8.3 and 50 mM KCl. SYBR® Green (Molecular Probes, Eugene, Oreg.) is a dye which fluoresces when bound to double stranded DNA. As double stranded PCR product is produced during amplification, the fluorescence from SYBR® Green increases. To each 20 µl aliquot of amplification mixture, 2 µl of template RT was added, and amplification was carried out according to standard protocols.

The following antisense oligonucleotides were shown to effectively deplete TTK RNA in the transfection assays:

```
Oligo 79-5AS:
GGGACTCTTCCAAATGGGCATGACT      (SEQ ID NO:5)

Oligo 79-9AS:
TCCAGTAACTCTTGCGTTCCCATGG      (SEQ ID NO:6)
```

The reverse control of each of these antisense oligonucleotides were synthesized, as were oligonucleotides with the identical sequence of the antisense oligonucleotides in reverse orientation (Reverse Control):

```
Oligo 79-5RC:
TCAGTACGGGTAAACCTTCTCAGGG        (SEQ ID NO:7)

Oligo 79-9RC:
GGTACCCTTGCGTTCTCAATGACCT        (SEQ ID NO:8)
```

The antisense oligonucleotides were introduced into a test cell and the effect upon TTK expression of the corresponding gene, as well as the effect induction of the cancerous phenotype, was examined as described below.

Example 5

Effect of TTK Expression on Proliferation

The effect of TTK on proliferation was assessed in metastatic breast cancer cell lines (MDA-MB-231 ("231")), SW620 colon colorectal carcinoma cells, or 847 human immortal fibroblast cells. Transfection was carried out as described above in Example 4.

Cells were plated to approximately 60-80% confluency in 96-well dishes. Antisense or reverse control oligonucleotide was diluted to 2 µM in OptiMEM™ and added to OptiMEM™ into which the delivery vehicle, lipitoid 116-6 in the case of SW620 cells or 1:1 lipitoid 1:cholesteroid 1 in the case of MDA-MB-231 cells, had been diluted. The oligo/delivery vehicle mixture was then further diluted into medium with serum on the cells. The final concentration of oligonucleotide for all experiments was 300 nM, and the final ratio of oligo to delivery vehicle for all experiments was 1.5 nmol lipitoid/µg oligonucleotide. Cells were transfected overnight at 37° C. and the transfection mixture was replaced with fresh medium the next morning.

Figure 7:
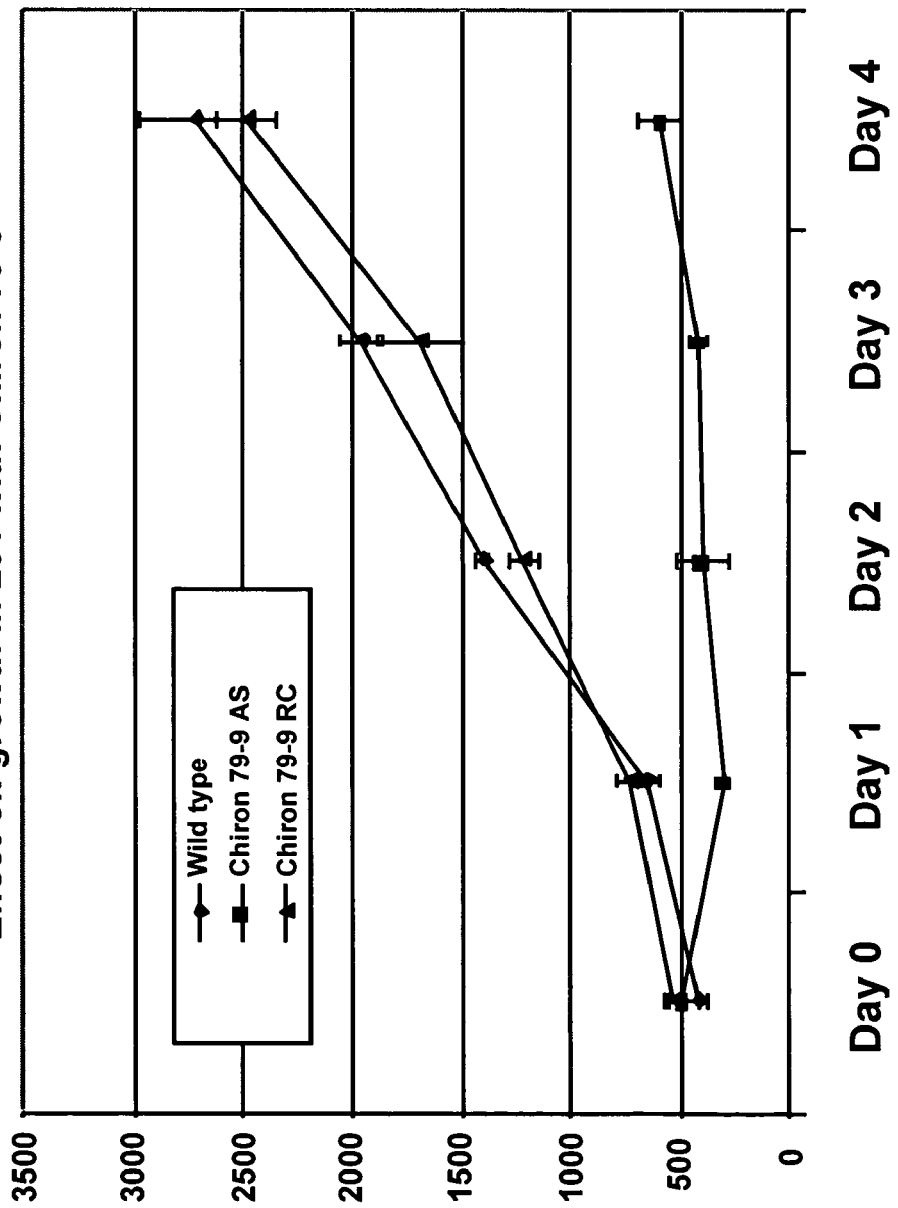
FIGS. 7 and 8 are graphs illustrating growth suppression of MDA-MB-231 cells following antisense suppression of TTK expression.
Figure 8:
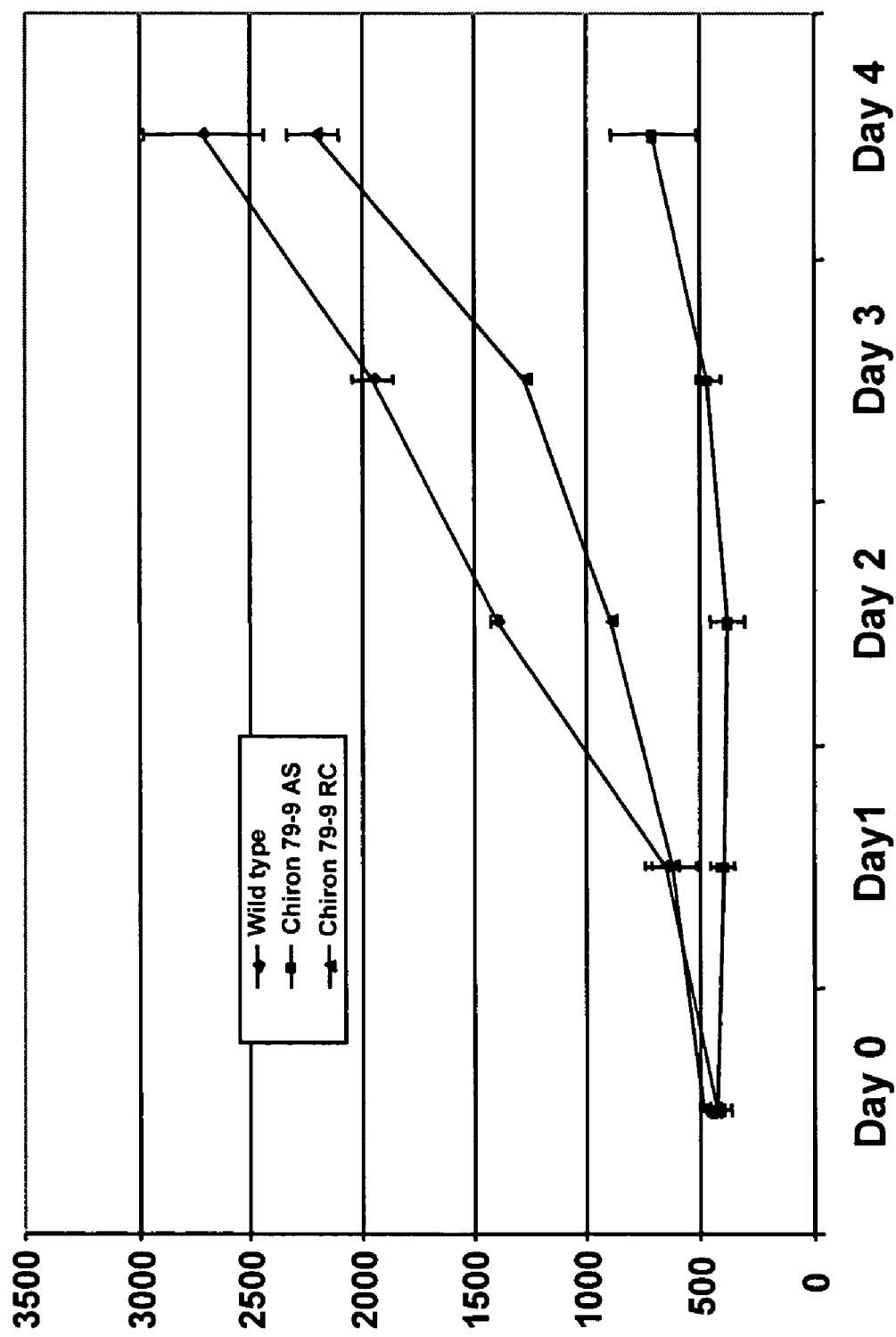
Figure 11:
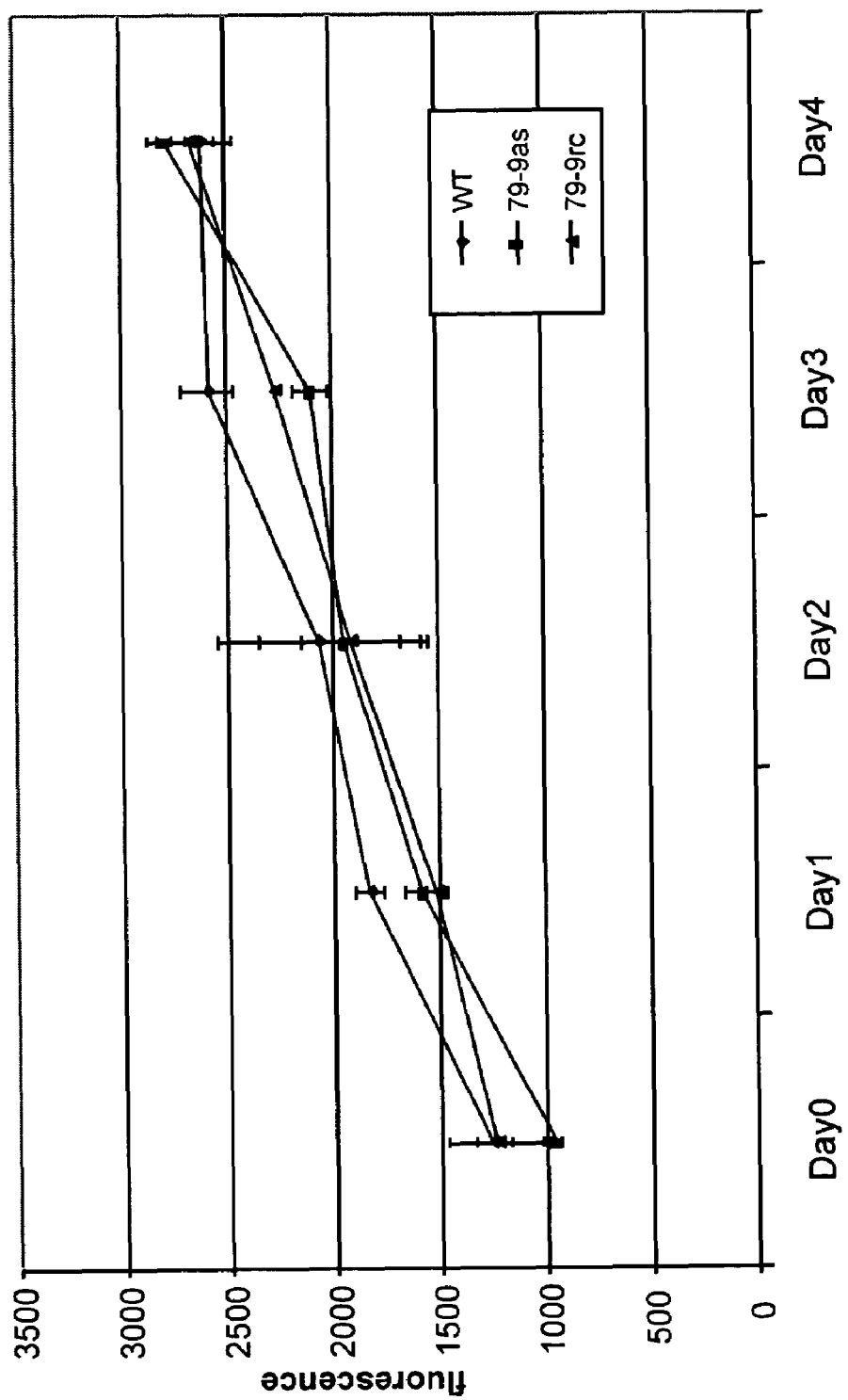
FIG. 11 is a graph illustrating that antisense suppression of TTK has no detectable effect on normal immortal fibroblasts.

Transfection of the antisense oligonucleotides into both SW620 colorectal carcinoma cells (FIG. 7) and 231 cells (FIG. 8) resulted in a decreased rate of proliferation compared to matched reverse control (RC) and oligonucleotides, but no inhibition of growth of 847 human immortal fibroblast cells (FIG. 11), suggesting possible tissue or transformation specificity in the functional role for the TTK protein.

Example 6

Effect of TTK Expression on Colony Formation

The effect of TTK expression upon colony formation was tested in a soft agar assay. Soft agar assays were conducted by first establishing a bottom layer of 2 ml of 0.6% agar in media plated fresh within a few hours of layering on the cells. The cell layer was formed on the bottom layer by removing cells transfected as described above from plates using 0.05% trypsin and washing twice in media. The cells were counted in a Coulter counter, and resuspended to $10^6$ per ml in media. 10 µl aliquots are placed with media in 96-well plates (to check counting with WST1), or diluted further for soft agar assay. 2000 cells are plated in 800 µl 0.4% agar in duplicate wells above 0.6% agar bottom layer. After the cell layer agar solidifies, 2 ml of media is dribbled on top and antisense or reverse control oligo is added without delivery vehicles. Fresh media and oligos are added every 3-4 days. Colonies are formed in 10 days to 3 weeks. Fields of colonies were counted by eye. Wst-1 metabolism values can be used to compensate for small differences in starting cell number. Larger fields can be scanned for visual record of differences.

Figure 9:
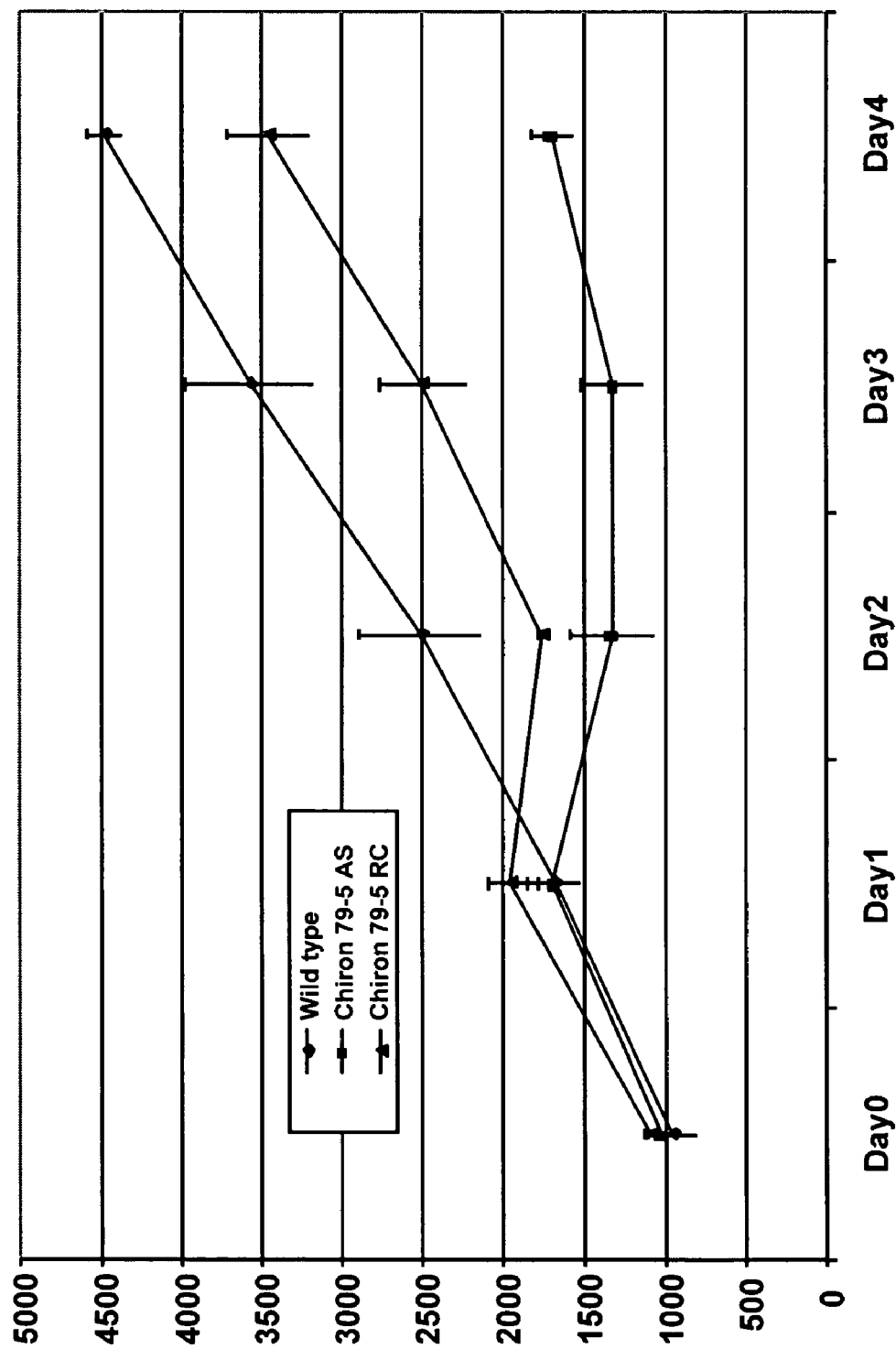
FIG. 9 is a graph illustrating growth suppression of SW620 cells following antisense suppression of TTK expression.
Figure 10:
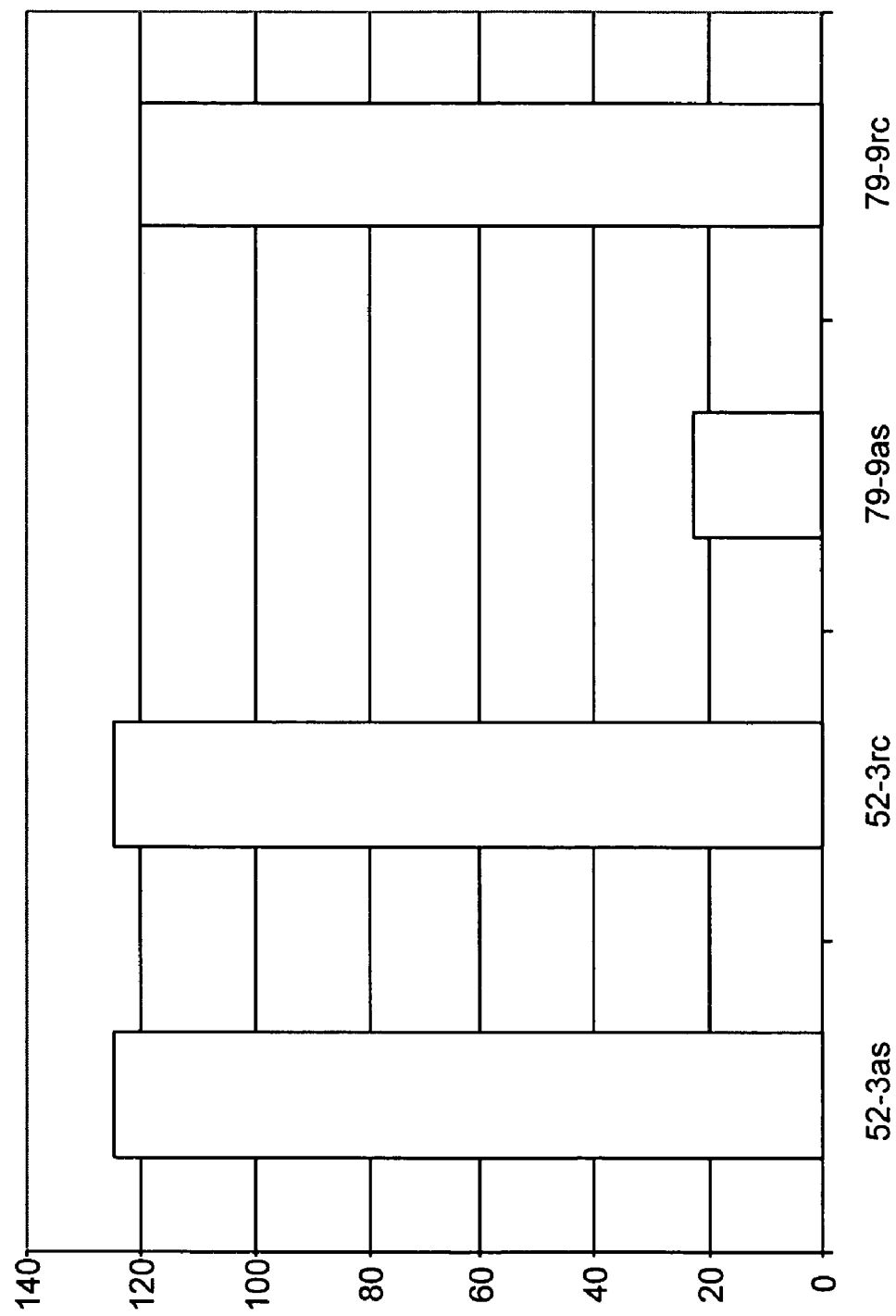
FIG. 10 is a graph illustrating suppression of colony formation of SW620 cells in soft agar following antisense suppression of TTK expression.

As shown in FIG. 9, antisense oligonucleotides to TTK (79-9AS) led to decreased colony size and number compared to control reverse control oligonucleotides (79-9RC) or to control oligonucleotides (52-3AS: TAGGTCTTTGGCCG-GTGATGGGTCG (SEQ ID NO:9) and 52-3RC: GCTGGG-TAGTGGCCGGTTTCTGGAT (SEQ ID NO:10)). The 52-3 antisense oligonucleotide is directed to the hD53 MRNA, and serves as a negative control in the experiment.

Example 7

Induction of Cell Death Upon Depletion of TTK ("Antisense Knockout")

SW620 cells were transfected as described for proliferation assays. For cytotoxic effect in the presence of cisplatin (cis), the same protocol was followed but cells were left in the presence of 2 µM drug. Each day, cytotoxicity was monitored by measuring the amount of LDH enzyme released in the medium due to membrane damage. The activity of LDH was measured using the Cytotoxicity Detection Kit from Roche Molecular Biochemicals. The data is provided as a ratio of LDH released in the medium vs. the total LDH present in the well at the same time point and treatment (rLDH/tLDH). A positive control using antisense and reverse control oligonucleotides for BCL2 (a known anti-apoptotic gene) shows that loss of message for BCL2 leads to an increase in cell death compared with treatment with the control oligonucleotide (background cytotoxicity due to transfection).

The following antisense oligonucleotides were tested for the ability to deplete the message levels of the gene corresponding to the indicated cluster. Oligo Name: AS or RC provides the name of the target gene or name of the oligo, and whether the oligo is antisense (AS) or a reverse control (RC).

TABLE B

| Oligo Name:Antisense (AS) or Reverse Control (RC) | Oligo Sequence | SEQ ID NO: |
|---|---|---|
| Chir39-5:AS | ACTCATCTGGCTGGGCTATGGTGGT | SEQ ID NO:11 |
| Chir39-5:RC | TGGTGGTATCGGGTCGGTCTACTCA | SEQ ID NO:12 |
| Chir79-9:AS | TCCAGTAACTCTTGCGTTCCCATGG | SEQ ID NO:6 |
| Chir79-9:RC | GGTACCCTTGCGTTCTCAATGACCT | SEQ ID NO:8 |

Figure 12:
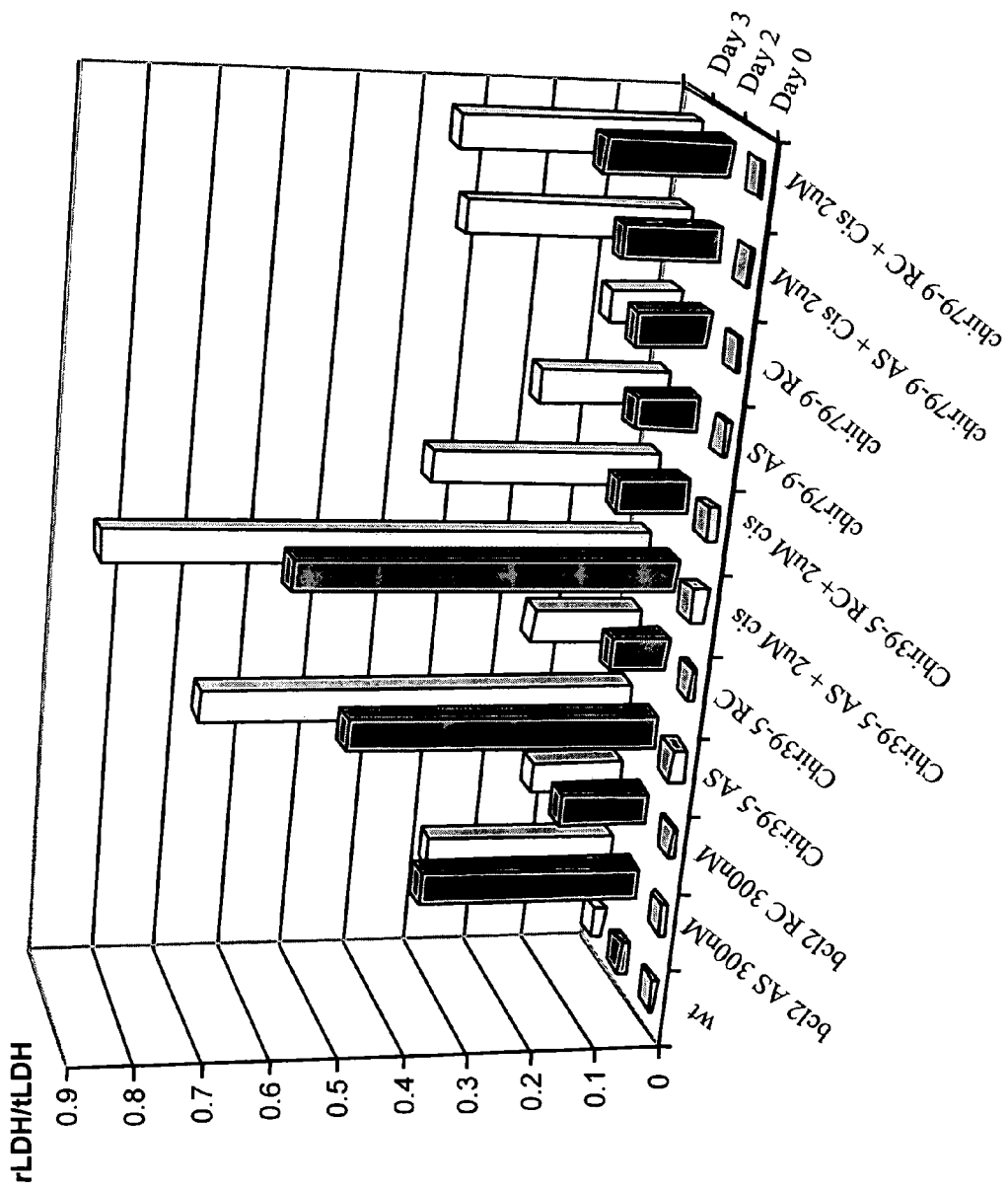
FIG. 12 is a bar graph illustrating induction of cell death upon depletion of TTK from SW620 cells.

As shown in FIG. 12, Chiron 79-9 (TTK) antisense does not sensitize the cells to treatment by cisplatin at a detectable level, but leads to increased death compared to control oligo at day 3.

Example 8

Sample assay for Agents that Modulate TTK Activity

This assay may be performed in microtitre plates. TTK was purified as a 6x His tagged fusion protein using a baculovirus expression system. Essentially 20 ul of 20 nM TTK (100 k Da) in TTK kinase buffer comprising 50 mM Hepes pH 7.4, 2 mM $MgCl_2$, 10 mM $MnCl_2$, 1 mM NaF, 50 mM NaCl, 1 mM DTT and 1 mg/ml BSA was added to 5 ul of a candidate agent diluted in 20% DMSO, 10 ul of a 2.8 uM solution of a biotinylated substrate peptide derived from cdc25, such as Biotin-SGSGSGLYRSPSMPENLNRPR-NH2 (SEQ ID NO:27) or Biotin-GGGGLYRSPSMPENLNRK-OH (SEQ ID NO:28) and 5 ul of 80 nM $^{33}P$-γATP in a well of a microtitre plate. Samples were mixed, incubated for 2 hours and each reaction is terminated using 20 ul of 0.5 M EDTA pH 8.0. 50 ul of the sample is transferred to a 96 well flat bottom Streptavidin coated flash plate, and the sample is incubated with the plate for 1 hr at room temperature. The wells of the plate are washed four times with 250 ul of calcium and magnesium-free phosphate buffered saline, and scintillation fluid is added to the sample. Activity of TTK was measured by calculating the emission of $^{33}P$, transferred by TTK from $^{33}P$-γATP to a substrate peptide, by scintillation.

Agents modulating TTK activity can be identified by comparing the activity of TTK in the presence of a candidate agent to the activity of TTK in the absence of a candidate agent.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the invention.

That which is claimed is:

1. A method of detecting colon or breast cancer expressing increased levels of TTK in a human subject, the method comprising:

detecting a level of expression of a TTK polypeptide in a test sample obtained from the subject, wherein the test sample is derived from tissue, tumor, blood, plasma, or serum; and comparing the level of expression of the TTK polypeptide in the test sample to a level of expression in a normal non-cancer sample of the same type; wherein detection of an expression level of TTK polypeptide in the test sample that is increased at least two fold relative to the level of expression in the normal non-cancer sample indicates that the subject has colon or breast cancer expressing increased levels of TTK.

2. The method of claim 1, wherein the test sample is a colon sample.

3. The method of claim 1, wherein the test sample is a breast sample.

4. The method of claim 1 wherein the cancer is colon cancer.

5. The method of claim 4 wherein the colon cancer is familial adenomatous polyposis, Gardner's syndrome, hereditary nonpolyposis colon cancer or familial colorectal cancer.

6. The method of claim 1 wherein the cancer is a breast cancer selected from the group consisting of ductal carcinoma in situ, infiltrating ductal carcinoma, lobular carcinoma in situ, infiltrating lobular carcinoma, inflammatory breast cancer, medullary carcinoma, mucinous carcinoma, Paget's disease of the nipple, Phyllodes tumor, and tubular carcinoma.

7. The method of claim 1 wherein the expression level of TTK polypeptide in the test sample is increased at least 2.5 fold relative to the level of expression in the normal non-cancer sample.

8. The method of claim 1 wherein the expression level of TTK polypeptide in the test sample is increased at least 5 fold relative to the level of expression in the normal non-cancer sample.

9. The method of claim 1 further comprising detecting differential expression of at least one of p53, DCC, ras, FAP MAPKAPK2, MARCKS and IGF2 polynucleotide in the test sample.

10. The method of claim 9 wherein an upregulation of expression of at least one of p53, DCC, ras, FAP MAPKAPK2, MARCKS and IGF2 combined with an increase in expression level of TTK polypeptide is indicative of colon or breast cancer.

11. The method of claim 9 wherein an upregulation of expression of p53, DCC, ras, FAP MAPKAPK2, MARCKS and IGF2 combined with an increase in expression level of TTK polypeptide is indicative of colon or breast cancer.

12. The method of claim 1 wherein expression levels of TTK polypeptide are measured using TTK-specific antibodies.

13. The method of claim 1 wherein the TTK polypeptide comprises an amino acid sequence at least 95% identical to a sequence of SEQ ID NO:14.

14. The method of claim 1 wherein the TTK polypeptide comprises an amino acid sequence at least 98% identical to a sequence of SEQ ID NO:14.

15. The method of claim 1 wherein the TTK polypeptide comprises the amino acid sequence of SEQ ID NO:14.

16. The method of claim 1 wherein the TTK polypeptide comprises an amino acid comprising at least 25 contiguous amino acids of SEQ ID NO:14.

17. The method of claim 1 wherein the TTK polypeptide comprises an amino acid comprising at least 50 contiguous amino acids of SEQ ID NO:14.

18. The method of claim 13 wherein the TTK polypeptide at least 95% identical to a sequence of SEQ ID NO:14 has protein kinase activity.

19. A method for determining whether cancerous tissue in a subject expresses increased levels of TTK, wherein the method comprises:
    detecting a level of expression of a TTK polypeptide in a cancerous tissue sample obtained from the subject and comparing the level of expression of the TTK polypeptide in the cancerous tissue sample to a level of expression in a normal non-cancerous sample of the same tissue,
    wherein detection of an expression level of TTK polypeptide in the cancerous tissue sample that is increased at least two fold relative to the level of expression in the normal non-cancerous sample indicates that the subject has cancerous tissue expressing increased levels of TTK.

20. The method of claim 19, wherein the tissue sample is a colon sample.

21. The method of claim 19, wherein the tissue sample is a breast sample.

22. The method of claim 19 wherein the cancer is colon cancer.

23. The method of claim 19 wherein the colon cancer is familial adenomatous polyposis, Gardner's syndrome, hereditary nonpolyposis colon cancer or familial colorectal cancer.

24. The method of claim 19 wherein the cancer is a breast cancer selected from the group consisting of ductal carcinoma in situ, infiltrating ductal carcinoma, lobular carcinoma in situ, infiltrating lobular carcinoma, inflammatory breast cancer, medullary carcinoma mucinous carcinoma, Paget's disease of the nipple, Phyllodes tumor, and tubular carcinoma.

25. The method of claim 19 wherein expression levels of TTK polypeptide are measured using TTK-specific antibodies.

26. The method of claim 19 wherein the TTK polypeptide comprises amino acid sequence at least 95% identical to a sequence of SEQ ID NO:14.

27. The method of claim 19 wherein the TTK polypeptide comprises amino acid sequence at least 98% identical to a sequence of SEQ ID NO:14.

28. The method of claim 19 wherein the TTK polypeptide comprises amino acid sequence of SEQ ID NO:14.

29. The method of claim 19 wherein the TTK polypeptide comprises amino acid comprising at least 25 contiguous amino acids of SEQ ID NO:14.

30. The method of claim 19 wherein the TTK polypeptide comprises amino acid comprising at least 50 contiguous amino acids of SEQ ID NO:14.

31. The method of claim 26 wherein the TTK polypeptide at least 95% identical to a sequence of SEQ ID NO:14 has protein kinase activity.

* * * * *

SEQUENCE LISTING

<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 1
cggaatcaag tcttctagct                                                 20

<210> SEQ ID NO 2
<211> LENGTH: 21
<212> TYPE: DNA
<213> ORGANISM: Artificial Sequence
<220> FEATURE:
<223> OTHER INFORMATION: synthesized oligonucleotide

<400> SEQUENCE: 2
ggttgctcaa aagttggtat g                                               21

<210> SEQ ID NO 3
<211> LENGTH: 24
<212> TYPE: DNA
<213> ORGANISM: Artificial Sequence
<220> FEATURE:
<223> OTHER INFORMATION: synthesized oligonucleotide

<400> SEQUENCE: 3
cgggaaatcg tgcgtgacat taag                                            24

<210> SEQ ID NO 4
<211> LENGTH: 24
<212> TYPE: DNA
<213> ORGANISM: Artificial Sequence
<220> FEATURE:
<223> OTHER INFORMATION: synthesized oligonucleotide

<400> SEQUENCE: 4
tgatctcctt ctgcatcctg tcgg                                            24

<210> SEQ ID NO 5
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 5
gggactcttc caaatgggca tgact                                          25

<210> SEQ ID NO 6
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 6
tccagtaact cttgcgttcc catgg                                          25

<210> SEQ ID NO 7
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 7
tcagtacggg taaaccttct caggg                                          25

<210> SEQ ID NO 8
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 8
ggtacccttg cgttctcaat gacct                                          25

<210> SEQ ID NO 9
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 9
taggtctttg gccggtgatg ggtcg                                          25

<210> SEQ ID NO 10
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 10
gctgggtagt ggccggtttc tggat                                          25

<210> SEQ ID NO 11
<211> LENGTH: 25
<212> TYPE: DNA
<213> ORGANISM: Artificial Sequence
<220> FEATURE:

-continued

```
<223> OTHER INFORMATION: synthesized oligonucleotide

<400> SEQUENCE: 11
actcatctgg ctgggctatg gtggt                                           25

<210> SEQ ID NO 12
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 12
tggtggtatc gggtcggtct actca                                           25

<210> SEQ ID NO 13
<211> LENGTH: 3866
<212> TYPE: DNA
<213> ORGANISM: Homo sapien
<220> FEATURE:
<221> NAME/KEY: CDS
<222> LOCATION: (1026)...(3551)
<220> FEATURE:
<221> NAME/KEY: misc_feature
<222> LOCATION: (0)...(0)
<223> OTHER INFORMATION: TTK

<400> SEQUENCE: 13
ggaattcctt ttttttttt tttgagatgg agtttcactc ttgttggcca ggctggagtg       60
caatggcaca atctcagctt actgcaacct ccgcctcccg ggttcaagcg attctcctgc     120
ctcagcctct caagtagctg ggattacagg catgtgccac cacccctggc taactaattt     180
cttttctatt tagtagagat ggggtttcac catgttggtc aggctggtct tgaactcctg     240
acctcaggtg atccacttgc cttggcctcc caaagtgcta ggattacagc cgtgaaactg     300
tgcctggctg attctttttt tgttgttgga tttttgaaac agggtctccc ttggtcgccc     360
aggctggagt gcagtggtgc gatcttggct cactataacc tccacctcct ggtttcaagt     420
gatcctccca ctttagcctc ctgagtagct gtgattacag gcgtgcacca ccacacccgg     480 ctaattttg tatttttatt agagacaggg tttcaccatg ttggccaggc tgttctcaaa     540
ctcctggact caagggatcc gcctgcctcc acttcccaaa gtcccgagat tacaggtgtg     600
agtcaccatg cctgacctta taattcttaa gtcatttttt ctggtccatt tcttccttag     660
ggtcctcaca caaatctgc attaggcggt acaataatcc ttaacttcat gattcacaaa     720
aggaagatga agtgattcat gatttagaaa ggggaagtag taagcccact gcacactcct     780
ggatgatgat cctaaatcca gatacagtaa aaatgggggta tgggaaggta gaatacaaaa    840
tttggtttaa attaattatc taaatatcta aaaacatttt tggatacatt gttgatgtga     900
atgtaagact gtacagactt cctagaaaac agtttgggtt ccatcttttc atttccccag     960
tgcagttttc tgtagaaatg gaatccgagg atttaagtgg cagagaattg acaattgatt    1020 ccata atg aac aaa gtg aga gac att aaa aat aag ttt aaa aat gaa gac   1070
      Met Asn Lys Val Arg Asp Ile Lys Asn Lys Phe Lys Asn Glu Asp
      1               5                  10                  15 ctt act gat gaa cta agc ttg aat aaa att tct gct gat act aca gat    1118
Leu Thr Asp Glu Leu Ser Leu Asn Lys Ile Ser Ala Asp Thr Thr Asp
             20                  25                  30 aac tcg gga act gtt aac caa att atg atg atg gca aac aac cca gag    1166
Asn Ser Gly Thr Val Asn Gln Ile Met Met Met Ala Asn Asn Pro Glu
         35                  40                  45
```

```
gac tgg ttg agt ttg ttg ctc aaa cta gag aaa aac agt gtt ccg cta    1214
Asp Trp Leu Ser Leu Leu Leu Lys Leu Glu Lys Asn Ser Val Pro Leu
         50                  55                  60 agt gat gct ctt tta aat aaa ttg att ggt cgt tac agt caa gca att    1262
Ser Asp Ala Leu Leu Asn Lys Leu Ile Gly Arg Tyr Ser Gln Ala Ile
 65                  70                  75 gaa gcg ctt ccc cca gat aaa tat ggc caa aat gag agt ttt gct aga    1310
Glu Ala Leu Pro Pro Asp Lys Tyr Gly Gln Asn Glu Ser Phe Ala Arg
 80                  85                  90                  95 att caa gtg aga ttt gct gaa tta aaa gct att caa gag cca gat gat    1358
Ile Gln Val Arg Phe Ala Glu Leu Lys Ala Ile Gln Glu Pro Asp Asp
                100                 105                 110 gca cgt gac tac ttt caa atg gcc aga gca aac tgc aag aaa ttt gct    1406
Ala Arg Asp Tyr Phe Gln Met Ala Arg Ala Asn Cys Lys Lys Phe Ala
        115                 120                 125 ttt gtt cat ata tct ttt gca caa ttt gaa ctg tca caa ggt aat gtc    1454
Phe Val His Ile Ser Phe Ala Gln Phe Glu Leu Ser Gln Gly Asn Val
        130                 135                 140 aaa aaa agt aaa caa ctt ctt caa aaa gct gta gaa cgt gga gca gta    1502
Lys Lys Ser Lys Gln Leu Leu Gln Lys Ala Val Glu Arg Gly Ala Val
145                 150                 155 cca cta gaa atg ctg gaa att gcc ctg cgg aat tta aac ctc caa aaa    1550
Pro Leu Glu Met Leu Glu Ile Ala Leu Arg Asn Leu Asn Leu Gln Lys
160                 165                 170                 175 aag cag ctg ctt tca gag gag gaa aag aag aat tta tca gca tct acg    1598
Lys Gln Leu Leu Ser Glu Glu Glu Lys Lys Asn Leu Ser Ala Ser Thr
                180                 185                 190 gta tta act gcc caa gaa tca ttt tcc ggt tca ctt ggg cat tta cag    1646
Val Leu Thr Ala Gln Glu Ser Phe Ser Gly Ser Leu Gly His Leu Gln
        195                 200                 205 aat agg aac aac agt tgt gat tcc aga gga cag act act aaa gcc agg    1694
Asn Arg Asn Asn Ser Cys Asp Ser Arg Gly Gln Thr Thr Lys Ala Arg
        210                 215                 220 ttt tta tat gga gag aac atg cca cca caa gat gca gaa ata ggt tac    1742
Phe Leu Tyr Gly Glu Asn Met Pro Pro Gln Asp Ala Glu Ile Gly Tyr
225                 230                 235 cgg aat tca ttg aga caa act aac aaa act aaa cag tca tgc cca ttt    1790
Arg Asn Ser Leu Arg Gln Thr Asn Lys Thr Lys Gln Ser Cys Pro Phe
240                 245                 250                 255 gga aga gtc cca gtt aac ctt cta aat agc cca gat tgt gat gtg aag    1838
Gly Arg Val Pro Val Asn Leu Leu Asn Ser Pro Asp Cys Asp Val Lys
                260                 265                 270 aca gat gat tca gtt gta cct tgt ttt atg aaa aga caa acc tct aga    1886
Thr Asp Asp Ser Val Val Pro Cys Phe Met Lys Arg Gln Thr Ser Arg
        275                 280                 285 tca gaa tgc cga gat ttg gtt gtg cct gga tct aaa cca agt gga aat    1934
Ser Glu Cys Arg Asp Leu Val Val Pro Gly Ser Lys Pro Ser Gly Asn
        290                 295                 300 gat tcc tgt gaa tta aga aat tta aag tct gtt caa aat agt cat ttc    1982
Asp Ser Cys Glu Leu Arg Asn Leu Lys Ser Val Gln Asn Ser His Phe
305                 310                 315 aag gaa cct ctg gtg tca gat gaa aag agt tct gaa ctt att att act    2030
Lys Glu Pro Leu Val Ser Asp Glu Lys Ser Ser Glu Leu Ile Ile Thr
320                 325                 330                 335 gat tca ata acc ctg aag aat aaa acg gaa tca gtt ctt cta gct aaa    2078
Asp Ser Ile Thr Leu Lys Asn Lys Thr Glu Ser Ser Leu Leu Ala Lys
                340                 345                 350 tta gaa gaa act aaa gag tat caa gaa cca gag gtt cca gag agt aac    2126
Leu Glu Glu Thr Lys Glu Tyr Gln Glu Pro Glu Val Pro Glu Ser Asn
        355                 360                 365
```

-continued

| | |
|---|---|
| cag aaa cag tgg caa gct aag aga aag tca gag tgt att aac cag aat<br>Gln Lys Gln Trp Gln Ala Lys Arg Lys Ser Glu Cys Ile Asn Gln Asn<br>370                       375                   380 | 2174 |
| cct gct gca tct tca aat cac tgg cag att ccg gag tta gcc cga aaa<br>Pro Ala Ala Ser Ser Asn His Trp Gln Ile Pro Glu Leu Ala Arg Lys<br>     385                   390                   395 | 2222 |
| gtt aat aca gag cag aaa cat acc act ttt gag caa cct gtc ttt tca<br>Val Asn Thr Glu Gln Lys His Thr Thr Phe Glu Gln Pro Val Phe Ser<br>400                       405                   410                   415 | 2270 |
| gtt tca aaa cag tca cca cca ata tca aca tct aaa tgg ttt gac cca<br>Val Ser Lys Gln Ser Pro Pro Ile Ser Thr Ser Lys Trp Phe Asp Pro<br>                   420                   425                   430 | 2318 |
| aaa tct att tgt aag aca cca agc agc aat acc ttg gat gat tac atg<br>Lys Ser Ile Cys Lys Thr Pro Ser Ser Asn Thr Leu Asp Asp Tyr Met<br>435                       440                   445 | 2366 |
| agc tgt ttt aga act cca gtt gta aag aat gac ttt cca cct gct tgt<br>Ser Cys Phe Arg Thr Pro Val Val Lys Asn Asp Phe Pro Pro Ala Cys<br>     450                   455                   460 | 2414 |
| cag ttg tca aca cct tat ggc caa cct gcc tgt ttc cag cag caa cag<br>Gln Leu Ser Thr Pro Tyr Gly Gln Pro Ala Cys Phe Gln Gln Gln Gln<br>465                       470                   475 | 2462 |
| cat caa ata ctt gcc act cca ctt caa aat tta cag gtt tta gca tct<br>His Gln Ile Leu Ala Thr Pro Leu Gln Asn Leu Gln Val Leu Ala Ser<br>480                       485                   490                   495 | 2510 |
| tct tca gca aat gaa tgc att tcg gtt aaa gga aga att tat tcc ata<br>Ser Ser Ala Asn Glu Cys Ile Ser Val Lys Gly Arg Ile Tyr Ser Ile<br>                   500                   505                   510 | 2558 |
| tta aag cag ata gga agt gga ggt tca agc aag gta ttt cag gtg tta<br>Leu Lys Gln Ile Gly Ser Gly Gly Ser Ser Lys Val Phe Gln Val Leu<br>515                       520                   525 | 2606 |
| aat gaa aag aaa cag ata tat gct ata aaa tat gtg aac tta gaa gaa<br>Asn Glu Lys Lys Gln Ile Tyr Ala Ile Lys Tyr Val Asn Leu Glu Glu<br>     530                   535                   540 | 2654 |
| gca gat aac caa act ctt gat agt tac cgg aac gaa ata gct tat ttg<br>Ala Asp Asn Gln Thr Leu Asp Ser Tyr Arg Asn Glu Ile Ala Tyr Leu<br>545                       550                   555 | 2702 |
| aat aaa cta caa caa cac agt gat aag atc atc cga ctt tat gat tat<br>Asn Lys Leu Gln Gln His Ser Asp Lys Ile Ile Arg Leu Tyr Asp Tyr<br>560                       565                   570                   575 | 2750 |
| gaa atc acg gac cag tac atc tac atg gta atg gag tgt gga aat att<br>Glu Ile Thr Asp Gln Tyr Ile Tyr Met Val Met Glu Cys Gly Asn Ile<br>                   580                   585                   590 | 2798 |
| gat ctt aat agt tgg ctt aaa aag aaa aaa tcc att gat cca tgg gaa<br>Asp Leu Asn Ser Trp Leu Lys Lys Lys Lys Ser Ile Asp Pro Trp Glu<br>595                       600                   605 | 2846 |
| cgc aag agt tac tgg aaa aat atg tta gag gca gtt cac aca atc cat<br>Arg Lys Ser Tyr Trp Lys Asn Met Leu Glu Ala Val His Thr Ile His<br>     610                   615                   620 | 2894 |
| caa cat ggc att gtt cac agt gat ctt aaa cca gct aac ttt ctg ata<br>Gln His Gly Ile Val His Ser Asp Leu Lys Pro Ala Asn Phe Leu Ile<br>625                       630                   635 | 2942 |
| gtt gat gga atg cta aag cta att gat ttt ggg att gca aac caa atg<br>Val Asp Gly Met Leu Lys Leu Ile Asp Phe Gly Ile Ala Asn Gln Met<br>640                       645                   650                   655 | 2990 |
| caa cca gat aca aca agt gtt gtt aaa gat tct cag gtt ggc aca gtt<br>Gln Pro Asp Thr Thr Ser Val Val Lys Asp Ser Gln Val Gly Thr Val<br>                   660                   665                   670 | 3038 |
| aat tat atg cca cca gaa gca atc aaa gat atg tct tcc tcc aga gag<br>Asn Tyr Met Pro Pro Glu Ala Ile Lys Asp Met Ser Ser Ser Arg Glu | 3086 |

-continued

```
                 675                 680                 685
aat ggg aaa tct aag tca aag ata agc ccc aaa agt gat gtt tgg tcc    3134
Asn Gly Lys Ser Lys Ser Lys Ile Ser Pro Lys Ser Asp Val Trp Ser
        690                 695                 700 tta gga tgt att ttg tac tat atg act tac ggg aaa aca cca ttt cag    3182
Leu Gly Cys Ile Leu Tyr Tyr Met Thr Tyr Gly Lys Thr Pro Phe Gln
705                 710                 715 cag ata att aat cag att tct aaa tta cat gcc ata att gat cct aat    3230
Gln Ile Ile Asn Gln Ile Ser Lys Leu His Ala Ile Ile Asp Pro Asn
720                 725                 730                 735 cat gaa att gaa ttt ccc gat att cca gag aaa gat ctt caa gat gtg    3278
His Glu Ile Glu Phe Pro Asp Ile Pro Glu Lys Asp Leu Gln Asp Val
                740                 745                 750 tta aag tgt tgt tta aaa agg gac cca aaa cag agg ata tcc att cct    3326
Leu Lys Cys Cys Leu Lys Arg Asp Pro Lys Gln Arg Ile Ser Ile Pro
        755                 760                 765 gag ctc ctg gct cat cca tat gtt caa att caa act cat cca gtt aac    3374
Glu Leu Leu Ala His Pro Tyr Val Gln Ile Gln Thr His Pro Val Asn
770                 775                 780 caa atg gcc aag gga acc act gaa gaa atg aaa tat gtt ctg ggc caa    3422
Gln Met Ala Lys Gly Thr Thr Glu Glu Met Lys Tyr Val Leu Gly Gln
785                 790                 795 ctt gtt ggt ctg aat tct cct aac tcc att ttg aaa gct gct aaa act    3470
Leu Val Gly Leu Asn Ser Pro Asn Ser Ile Leu Lys Ala Ala Lys Thr
800                 805                 810                 815 tta tat gaa cac tat agt ggt ggt gaa agt cat aat tct tca tcc tcc    3518
Leu Tyr Glu His Tyr Ser Gly Gly Glu Ser His Asn Ser Ser Ser Ser
                820                 825                 830 aag act ttt gaa aaa aaa agg gga aaa aaa tga tttgcagtta ttcgtaatgt   3571
Lys Thr Phe Glu Lys Lys Arg Gly Lys Lys *
        835                 840 cagataggag gtataaaata tattggactg ttatactctt gaatccctgt ggaaatctac   3631
atttgaagac aacatcactc tgaagtgtta tcagcaaaaa aaattcagtg agattatctt   3691
taaaagaaaa ctgtaaaaat agcaaccact tatggcactg tatatattgt agacttgttt   3751
tctctgtttt atgctcttgt gtaatctact tgacatcatt ttactcttgg aatagtgggt   3811
ggatagcaag tatattctaa aaactttgt aaataaagtt ttgtggctaa aatga          3866
```

<210> SEQ ID NO 14
<211> LENGTH: 841
<212> TYPE: PRT
<213> ORGANISM: Homo sapiens

<400> SEQUENCE: 14

```
Met Asn Lys Val Arg Asp Ile Lys Asn Lys Phe Lys Asn Glu Asp Leu
1               5                   10                  15

Thr Asp Glu Leu Ser Leu Asn Lys Ile Ser Ala Asp Thr Thr Asp Asn
            20                  25                  30

Ser Gly Thr Val Asn Gln Ile Met Met Met Ala Asn Asn Pro Glu Asp
        35                  40                  45

Trp Leu Ser Leu Leu Leu Lys Leu Glu Lys Asn Ser Val Pro Leu Ser
    50                  55                  60

Asp Ala Leu Leu Asn Lys Leu Ile Gly Arg Tyr Ser Gln Ala Ile Glu
65                  70                  75                  80

Ala Leu Pro Pro Asp Lys Tyr Gly Gln Asn Glu Ser Phe Ala Arg Ile
                85                  90                  95

Gln Val Arg Phe Ala Glu Leu Lys Ala Ile Gln Glu Pro Asp Asp Ala
```

-continued

```
                100                 105                 110
Arg Asp Tyr Phe Gln Met Ala Arg Ala Asn Cys Lys Lys Phe Ala Phe
            115                 120                 125

Val His Ile Ser Phe Ala Gln Phe Glu Leu Ser Gln Gly Asn Val Lys
130                 135                 140

Lys Ser Lys Gln Leu Leu Gln Lys Ala Val Glu Arg Gly Ala Val Pro
145                 150                 155                 160

Leu Glu Met Leu Glu Ile Ala Leu Arg Asn Leu Asn Leu Gln Lys Lys
                165                 170                 175

Gln Leu Leu Ser Glu Glu Lys Lys Asn Leu Ser Ala Ser Thr Val
            180                 185                 190

Leu Thr Ala Gln Glu Ser Phe Ser Gly Ser Leu Gly His Leu Gln Asn
            195                 200                 205

Arg Asn Asn Ser Cys Asp Ser Arg Gly Gln Thr Thr Lys Ala Arg Phe
210                 215                 220

Leu Tyr Gly Glu Asn Met Pro Pro Gln Asp Ala Glu Ile Gly Tyr Arg
225                 230                 235                 240

Asn Ser Leu Arg Gln Thr Asn Lys Thr Lys Gln Ser Cys Pro Phe Gly
                245                 250                 255

Arg Val Pro Val Asn Leu Leu Asn Ser Pro Asp Cys Asp Val Lys Thr
            260                 265                 270

Asp Asp Ser Val Val Pro Cys Phe Met Lys Arg Gln Thr Ser Arg Ser
            275                 280                 285

Glu Cys Arg Asp Leu Val Val Pro Gly Ser Lys Pro Ser Gly Asn Asp
            290                 295                 300

Ser Cys Glu Leu Arg Asn Leu Lys Ser Val Gln Asn Ser His Phe Lys
305                 310                 315                 320

Glu Pro Leu Val Ser Asp Glu Lys Ser Ser Glu Leu Ile Ile Thr Asp
                325                 330                 335

Ser Ile Thr Leu Lys Asn Lys Thr Glu Ser Ser Leu Leu Ala Lys Leu
            340                 345                 350

Glu Glu Thr Lys Glu Tyr Gln Glu Pro Glu Val Pro Glu Ser Asn Gln
            355                 360                 365

Lys Gln Trp Gln Ala Lys Arg Lys Ser Glu Cys Ile Asn Gln Asn Pro
370                 375                 380

Ala Ala Ser Ser Asn His Trp Gln Ile Pro Glu Leu Ala Arg Lys Val
385                 390                 395                 400

Asn Thr Glu Gln Lys His Thr Thr Phe Glu Gln Pro Val Phe Ser Val
                405                 410                 415

Ser Lys Gln Ser Pro Pro Ile Ser Thr Ser Lys Trp Phe Asp Pro Lys
            420                 425                 430

Ser Ile Cys Lys Thr Pro Ser Ser Asn Thr Leu Asp Asp Tyr Met Ser
            435                 440                 445

Cys Phe Arg Thr Pro Val Val Lys Asn Asp Phe Pro Pro Ala Cys Gln
450                 455                 460

Leu Ser Thr Pro Tyr Gly Gln Pro Ala Cys Phe Gln Gln Gln His
465                 470                 475                 480

Gln Ile Leu Ala Thr Pro Leu Gln Asn Leu Gln Val Leu Ala Ser Ser
                485                 490                 495

Ser Ala Asn Glu Cys Ile Ser Val Lys Gly Arg Ile Tyr Ser Ile Leu
            500                 505                 510

Lys Gln Ile Gly Ser Gly Gly Ser Ser Lys Val Phe Gln Val Leu Asn
            515                 520                 525
```

```
Glu Lys Lys Gln Ile Tyr Ala Ile Lys Tyr Val Asn Leu Glu Glu Ala
        530                 535                 540

Asp Asn Gln Thr Leu Asp Ser Tyr Arg Asn Glu Ile Ala Tyr Leu Asn
545                 550                 555                 560

Lys Leu Gln Gln His Ser Asp Lys Ile Ile Arg Leu Tyr Asp Tyr Glu
            565                 570                 575

Ile Thr Asp Gln Tyr Ile Tyr Met Val Met Glu Cys Gly Asn Ile Asp
                580                 585                 590

Leu Asn Ser Trp Leu Lys Lys Lys Ser Ile Asp Pro Trp Glu Arg
        595                 600                 605

Lys Ser Tyr Trp Lys Asn Met Leu Glu Ala Val His Thr Ile His Gln
        610                 615                 620

His Gly Ile Val His Ser Asp Leu Lys Pro Ala Asn Phe Leu Ile Val
625                 630                 635                 640

Asp Gly Met Leu Lys Leu Ile Asp Phe Gly Ile Ala Asn Gln Met Gln
            645                 650                 655

Pro Asp Thr Thr Ser Val Val Lys Asp Ser Gln Val Gly Thr Val Asn
                660                 665                 670

Tyr Met Pro Pro Glu Ala Ile Lys Asp Met Ser Ser Ser Arg Glu Asn
        675                 680                 685

Gly Lys Ser Lys Ser Lys Ile Ser Pro Lys Ser Asp Val Trp Ser Leu
        690                 695                 700

Gly Cys Ile Leu Tyr Tyr Met Thr Tyr Gly Lys Thr Pro Phe Gln Gln
705                 710                 715                 720

Ile Ile Asn Gln Ile Ser Lys Leu His Ala Ile Ile Asp Pro Asn His
            725                 730                 735

Glu Ile Glu Phe Pro Asp Ile Pro Glu Lys Asp Leu Gln Asp Val Leu
                740                 745                 750

Lys Cys Cys Leu Lys Arg Asp Pro Lys Gln Arg Ile Ser Ile Pro Glu
        755                 760                 765

Leu Leu Ala His Pro Tyr Val Gln Ile Gln Thr His Pro Val Asn Gln
        770                 775                 780

Met Ala Lys Gly Thr Thr Glu Glu Met Lys Tyr Val Leu Gly Gln Leu
785                 790                 795                 800

Val Gly Leu Asn Ser Pro Asn Ser Ile Leu Lys Ala Ala Lys Thr Leu
            805                 810                 815

Tyr Glu His Tyr Ser Gly Gly Glu Ser His Asn Ser Ser Ser Ser Lys
                820                 825                 830

Thr Phe Glu Lys Lys Arg Gly Lys Lys
        835                 840

<210> SEQ ID NO 15
<211> LENGTH: 2735
<212> TYPE: DNA
<213> ORGANISM: Saccharomyces cerevisiae
<220> FEATURE:
<221> NAME/KEY: CDS
<222> LOCATION: (34)...(2499)

<400> SEQUENCE: 15 agaaagata gtgttacaca acatcaacta aaa atg gaa aat att aca caa ccc      54
                                    Met Glu Asn Ile Thr Gln Pro
                                      1               5 aca cag caa tcc acg cag gct act caa agg ttt ttg att gag aag ttt    102
Thr Gln Gln Ser Thr Gln Ala Thr Gln Arg Phe Leu Ile Glu Lys Phe
         10                  15                  20
```

-continued

| | | |
|---|---|---|
| tct caa gaa cag atc ggc gaa aac att gtg tgc agg gtc att tgt acc<br>Ser Gln Glu Gln Ile Gly Glu Asn Ile Val Cys Arg Val Ile Cys Thr<br>  25                        30                        35 | 150 |
| acg ggt caa att ccc atc cga gat ttg tca gct gat att tca caa gtg<br>Thr Gly Gln Ile Pro Ile Arg Asp Leu Ser Ala Asp Ile Ser Gln Val<br>40                        45                        50                        55 | 198 |
| ctt aag gaa aaa cga tcc ata aag aaa gtt tgg aca ttt ggt aga aac<br>Leu Lys Glu Lys Arg Ser Ile Lys Lys Val Trp Thr Phe Gly Arg Asn<br>              60                        65                        70 | 246 |
| cca gcc tgt gac tat cat tta gga aac att tca aga ctg tca aat aag<br>Pro Ala Cys Asp Tyr His Leu Gly Asn Ile Ser Arg Leu Ser Asn Lys<br>                   75                        80                        85 | 294 |
| cat ttc caa ata cta cta gga gaa gac ggt aac ctt tta ttg aat gac<br>His Phe Gln Ile Leu Leu Gly Glu Asp Gly Asn Leu Leu Leu Asn Asp<br>          90                        95                        100 | 342 |
| att tcc act aat ggg acc tgg tta aat ggg caa aaa gtc gag aag aac<br>Ile Ser Thr Asn Gly Thr Trp Leu Asn Gly Gln Lys Val Glu Lys Asn<br>105                      110                        115 | 390 |
| agc aat cag tta ctg tct caa ggt gat gaa ata acc gtt ggt gta ggc<br>Ser Asn Gln Leu Leu Ser Gln Gly Asp Glu Ile Thr Val Gly Val Gly<br>120                      125                        130                        135 | 438 |
| gtg gaa tca gat att tta tct ctg gtc att ttc ata aac gac aaa ttt<br>Val Glu Ser Asp Ile Leu Ser Leu Val Ile Phe Ile Asn Asp Lys Phe<br>                  140                        145                        150 | 486 |
| aag cag tgc ctc gag cag aac aaa gtt gat cgc ata aga tct aac ctg<br>Lys Gln Cys Leu Glu Gln Asn Lys Val Asp Arg Ile Arg Ser Asn Leu<br>              155                        160                        165 | 534 |
| aaa aat acc tct aaa ata gct tct cct ggt ctt aca tca tct act gca<br>Lys Asn Thr Ser Lys Ile Ala Ser Pro Gly Leu Thr Ser Ser Thr Ala<br>170                      175                        180 | 582 |
| tca tca atg gtg gcc aac aag act ggt att ttt aag gat ttt tcg att<br>Ser Ser Met Val Ala Asn Lys Thr Gly Ile Phe Lys Asp Phe Ser Ile<br>                185                        190                        195 | 630 |
| att gac gaa gtg gtg ggc cag ggt gca ttt gcc aca gta aag aaa gcc<br>Ile Asp Glu Val Val Gly Gln Gly Ala Phe Ala Thr Val Lys Lys Ala<br>200                      205                        210                        215 | 678 |
| att gaa aga act act ggg aaa aca ttc gcg gtg aag att ata agt aaa<br>Ile Glu Arg Thr Thr Gly Lys Thr Phe Ala Val Lys Ile Ile Ser Lys<br>                220                        225                        230 | 726 |
| cgc aaa gta ata ggc aat atg gat ggt gtg aca aga gag tta gaa gta<br>Arg Lys Val Ile Gly Asn Met Asp Gly Val Thr Arg Glu Leu Glu Val<br>235                      240                        245 | 774 |
| ttg caa aag ctc aat cat cca agg ata gta cga ttg aaa gga ttt tat<br>Leu Gln Lys Leu Asn His Pro Arg Ile Val Arg Leu Lys Gly Phe Tyr<br>              250                        255                        260 | 822 |
| gaa gat act gag agt tat tat atg gtg atg gag ttc gtt tct ggt ggt<br>Glu Asp Thr Glu Ser Tyr Tyr Met Val Met Glu Phe Val Ser Gly Gly<br>265                      270                        275 | 870 |
| gac tta atg gat ttt gtt gct gct cat ggt gcg gtt gga gaa gat gct<br>Asp Leu Met Asp Phe Val Ala Ala His Gly Ala Val Gly Glu Asp Ala<br>280                      285                        290                        295 | 918 |
| ggg agg gag ata tcc agg cag ata ctc aca gca ata aaa tac att cac<br>Gly Arg Glu Ile Ser Arg Gln Ile Leu Thr Ala Ile Lys Tyr Ile His<br>                300                        305                        310 | 966 |
| tct atg ggc atc agc cat cgt gac cta aag ccc gat aat att ctt att<br>Ser Met Gly Ile Ser His Arg Asp Leu Lys Pro Asp Asn Ile Leu Ile<br>              315                        320                        325 | 1014 |
| gaa caa gac gat cct gta ttg gta aag ata acc gac ttt ggt ctg gca<br>Glu Gln Asp Asp Pro Val Leu Val Lys Ile Thr Asp Phe Gly Leu Ala | 1062 |

-continued

```
                330                 335                 340
aaa gta caa gga aat ggg tct ttt atg aaa acc ttc tgt ggc act ttg          1110
Lys Val Gln Gly Asn Gly Ser Phe Met Lys Thr Phe Cys Gly Thr Leu
    345                 350                 355 gca tat gtg gca cct gaa gtc atc aga ggt aaa gat aca tcc gta tct          1158
Ala Tyr Val Ala Pro Glu Val Ile Arg Gly Lys Asp Thr Ser Val Ser
360                 365                 370                 375 cct gat gaa tac gaa gaa agg aat gag tac tct tcg tta gtg gat atg          1206
Pro Asp Glu Tyr Glu Glu Arg Asn Glu Tyr Ser Ser Leu Val Asp Met
                380                 385                 390 tgg tca atg gga tgt ctt gtg tat gtt atc cta acg ggc cac tta cct          1254
Trp Ser Met Gly Cys Leu Val Tyr Val Ile Leu Thr Gly His Leu Pro
            395                 400                 405 ttt agt ggt agc aca cag gac caa tta tat aaa cag att gga aga ggc          1302
Phe Ser Gly Ser Thr Gln Asp Gln Leu Tyr Lys Gln Ile Gly Arg Gly
        410                 415                 420 tca tat cat gaa ggg ccc ctc aaa gat ttc cgg ata tct gaa gaa gca          1350
Ser Tyr His Glu Gly Pro Leu Lys Asp Phe Arg Ile Ser Glu Glu Ala
    425                 430                 435 aga gat ttc ata gat tca ttg tta cag gtg gat cca aat aat agg tcg          1398
Arg Asp Phe Ile Asp Ser Leu Leu Gln Val Asp Pro Asn Asn Arg Ser
440                 445                 450                 455 aca gct gca aaa gcc ttg aat cat ccc tgg atc aag atg agt cca ttg          1446
Thr Ala Ala Lys Ala Leu Asn His Pro Trp Ile Lys Met Ser Pro Leu
                460                 465                 470 ggc tca caa tca tat ggt gat ttt tca caa ata tcc tta tca caa tcg          1494
Gly Ser Gln Ser Tyr Gly Asp Phe Ser Gln Ile Ser Leu Ser Gln Ser
            475                 480                 485 ttg tcg cag cag aaa tta tta gaa aat atg gac gat gct caa tac gaa          1542
Leu Ser Gln Gln Lys Leu Leu Glu Asn Met Asp Asp Ala Gln Tyr Glu
        490                 495                 500 ttt gtc aaa gcg caa agg aaa tta caa atg gag caa caa ctt caa gaa          1590
Phe Val Lys Ala Gln Arg Lys Leu Gln Met Glu Gln Gln Leu Gln Glu
    505                 510                 515 cag gat cag gaa gac caa gat gga aaa att caa gga ttt aaa ata ccc          1638
Gln Asp Gln Glu Asp Gln Asp Gly Lys Ile Gln Gly Phe Lys Ile Pro
520                 525                 530                 535 gca cac gcc cct att cga tat aca cag ccc aaa agc att gaa gca gaa          1686
Ala His Ala Pro Ile Arg Tyr Thr Gln Pro Lys Ser Ile Glu Ala Glu
                540                 545                 550 act aga gaa caa aaa ctt tta cat tcc aat aat act gag aat gtc aag          1734
Thr Arg Glu Gln Lys Leu Leu His Ser Asn Asn Thr Glu Asn Val Lys
            555                 560                 565 agc tca aag aaa aag ggt aat ggt agg ttt tta act tta aaa cca ttg          1782
Ser Ser Lys Lys Lys Gly Asn Gly Arg Phe Leu Thr Leu Lys Pro Leu
        570                 575                 580 cct gac agc att att caa gaa agc ctg gag att cag caa ggt gtg aat          1830
Pro Asp Ser Ile Ile Gln Glu Ser Leu Glu Ile Gln Gln Gly Val Asn
    585                 590                 595 cca ttt ttc att ggt aga tcc gag gat tgc aat tgt aaa att gaa gac          1878
Pro Phe Phe Ile Gly Arg Ser Glu Asp Cys Asn Cys Lys Ile Glu Asp
600                 605                 610                 615 aat agg ttg tct cga gtt cat tgc ttc att ttc aaa aag agg cat gct          1926
Asn Arg Leu Ser Arg Val His Cys Phe Ile Phe Lys Lys Arg His Ala
                620                 625                 630 gta ggc aaa agc atg tat gaa tct ccg gca caa ggt tta gat gat att          1974
Val Gly Lys Ser Met Tyr Glu Ser Pro Ala Gln Gly Leu Asp Asp Ile
            635                 640                 645 tgg tat tgc cac acc gga act aac gtg agc tat tta aat aat aac cgc          2022
```

-continued

```
Trp Tyr Cys His Thr Gly Thr Asn Val Ser Tyr Leu Asn Asn Asn Arg
        650                 655                 660 atg ata cag ggt acg aaa ttc ctt tta caa gac gga gat gaa atc aag      2070
Met Ile Gln Gly Thr Lys Phe Leu Leu Gln Asp Gly Asp Glu Ile Lys
665                 670                 675 atc att tgg gat aaa aac aat aaa ttt gtc att ggc ttt aaa gtg gaa      2118
Ile Ile Trp Asp Lys Asn Asn Lys Phe Val Ile Gly Phe Lys Val Glu
680                 685                 690                 695 att aac gat act aca ggt ctg ttt aac gag gga tta ggt atg tta caa      2166
Ile Asn Asp Thr Thr Gly Leu Phe Asn Glu Gly Leu Gly Met Leu Gln
                700                 705                 710 gaa caa aga gta gta ctt aag caa aca gcc gaa gaa aaa gat ttg gtg      2214
Glu Gln Arg Val Val Leu Lys Gln Thr Ala Glu Glu Lys Asp Leu Val
            715                 720                 725 aaa aag tta acc cag atg atg gca gct caa cgt gca aat caa ccc tcg      2262
Lys Lys Leu Thr Gln Met Met Ala Ala Gln Arg Ala Asn Gln Pro Ser
        730                 735                 740 gct tct tct tca tca atg tcg gct aag aag ccg cca gtt agc gat aca      2310
Ala Ser Ser Ser Ser Met Ser Ala Lys Lys Pro Pro Val Ser Asp Thr
    745                 750                 755 aat aat aac ggc aat aat tcg gta cta aac gac ttg gta gag tca ccg      2358
Asn Asn Asn Gly Asn Asn Ser Val Leu Asn Asp Leu Val Glu Ser Pro
760                 765                 770                 775 att aat gcg aat acg ggg aac att ttg aag aga ata cat tcg gta agt      2406
Ile Asn Ala Asn Thr Gly Asn Ile Leu Lys Arg Ile His Ser Val Ser
                780                 785                 790 tta tcg caa tca caa att gat cct agt aag aag gtt aaa agg gca aaa      2454
Leu Ser Gln Ser Gln Ile Asp Pro Ser Lys Lys Val Lys Arg Ala Lys
            795                 800                 805 ttg gac caa acc tca aaa ggc ccc gag aat ttg caa ttt tcg taa          2499
Leu Asp Gln Thr Ser Lys Gly Pro Glu Asn Leu Gln Phe Ser *
        810                 815                 820 ccaaggacaa ataccatag aaaatgctgc ccctttttaa gagagaagat ggtagatacc     2559
aatactcaga attcccagta caaagaacca atatcggagt caataaacag tatgatgaac    2619
ttgctttcgc aaataaaaga tatcactcag aagcacccag taataaagga tgcagatagc    2679
tcgagatttg gtaaggttga gtttagggac ttttatgacg aagtttcacg gaattc        2735
```

<210> SEQ ID NO 16
<211> LENGTH: 821
<212> TYPE: PRT
<213> ORGANISM: Saccharomyces cerevisiae

<400> SEQUENCE: 16

```
Met Glu Asn Ile Thr Gln Pro Thr Gln Gln Ser Thr Gln Ala Thr Gln
1               5                  10                  15

Arg Phe Leu Ile Glu Lys Phe Ser Gln Glu Gln Ile Gly Glu Asn Ile
            20                  25                  30

Val Cys Arg Val Ile Cys Thr Thr Gly Gln Ile Pro Ile Arg Asp Leu
        35                  40                  45

Ser Ala Asp Ile Ser Gln Val Leu Lys Glu Lys Arg Ser Ile Lys Lys
    50                  55                  60

Val Trp Thr Phe Gly Arg Asn Pro Ala Cys Asp Tyr His Leu Gly Asn
65                  70                  75                  80

Ile Ser Arg Leu Ser Asn Lys His Phe Gln Ile Leu Leu Gly Glu Asp
                85                  90                  95

Gly Asn Leu Leu Leu Asn Asp Ile Ser Thr Asn Gly Thr Trp Leu Asn
```

```
                  100                 105                 110
Gly Gln Lys Val Glu Lys Asn Ser Asn Gln Leu Leu Ser Gln Gly Asp
            115                 120                 125
Glu Ile Thr Val Gly Val Gly Val Glu Ser Asp Ile Leu Ser Leu Val
            130                 135                 140
Ile Phe Ile Asn Asp Lys Phe Lys Gln Cys Leu Glu Gln Asn Lys Val
145                 150                 155                 160
Asp Arg Ile Arg Ser Asn Leu Lys Asn Thr Ser Lys Ile Ala Ser Pro
                165                 170                 175
Gly Leu Thr Ser Ser Thr Ala Ser Ser Met Val Ala Asn Lys Thr Gly
            180                 185                 190
Ile Phe Lys Asp Phe Ser Ile Ile Asp Glu Val Val Gly Gln Gly Ala
            195                 200                 205
Phe Ala Thr Val Lys Lys Ala Ile Glu Arg Thr Thr Gly Lys Thr Phe
            210                 215                 220
Ala Val Lys Ile Ile Ser Lys Arg Lys Val Ile Gly Asn Met Asp Gly
225                 230                 235                 240
Val Thr Arg Glu Leu Glu Val Leu Gln Lys Leu Asn His Pro Arg Ile
                245                 250                 255
Val Arg Leu Lys Gly Phe Tyr Glu Asp Thr Glu Ser Tyr Tyr Met Val
            260                 265                 270
Met Glu Phe Val Ser Gly Gly Asp Leu Met Asp Phe Val Ala Ala His
            275                 280                 285
Gly Ala Val Gly Glu Asp Ala Gly Arg Glu Ile Ser Arg Gln Ile Leu
            290                 295                 300
Thr Ala Ile Lys Tyr Ile His Ser Met Gly Ile Ser His Arg Asp Leu
305                 310                 315                 320
Lys Pro Asp Asn Ile Leu Ile Glu Gln Asp Asp Pro Val Leu Val Lys
                325                 330                 335
Ile Thr Asp Phe Gly Leu Ala Lys Val Gln Gly Asn Gly Ser Phe Met
            340                 345                 350
Lys Thr Phe Cys Gly Thr Leu Ala Tyr Val Ala Pro Glu Val Ile Arg
            355                 360                 365
Gly Lys Asp Thr Ser Val Ser Pro Asp Glu Tyr Glu Glu Arg Asn Glu
            370                 375                 380
Tyr Ser Ser Leu Val Asp Met Trp Ser Met Gly Cys Leu Val Tyr Val
385                 390                 395                 400
Ile Leu Thr Gly His Leu Pro Phe Ser Gly Ser Thr Gln Asp Gln Leu
                405                 410                 415
Tyr Lys Gln Ile Gly Arg Gly Ser Tyr His Glu Gly Pro Leu Lys Asp
            420                 425                 430
Phe Arg Ile Ser Glu Glu Ala Arg Asp Phe Ile Asp Ser Leu Leu Gln
            435                 440                 445
Val Asp Pro Asn Asn Arg Ser Thr Ala Ala Lys Ala Leu Asn His Pro
            450                 455                 460
Trp Ile Lys Met Ser Pro Leu Gly Ser Gln Ser Tyr Gly Asp Phe Ser
465                 470                 475                 480
Gln Ile Ser Leu Ser Gln Ser Leu Ser Gln Gln Lys Leu Leu Glu Asn
                485                 490                 495
Met Asp Asp Ala Gln Tyr Glu Phe Val Lys Ala Gln Arg Lys Leu Gln
            500                 505                 510
Met Glu Gln Gln Leu Gln Glu Gln Asp Gln Glu Asp Gln Asp Gly Lys
            515                 520                 525
```

```
Ile Gln Gly Phe Lys Ile Pro Ala His Ala Pro Ile Arg Tyr Thr Gln
    530                 535                 540
Pro Lys Ser Ile Glu Ala Glu Thr Arg Glu Gln Lys Leu Leu His Ser
545                 550                 555                 560
Asn Asn Thr Glu Asn Val Lys Ser Ser Lys Lys Gly Asn Gly Arg
                565                 570                 575
Phe Leu Thr Leu Lys Pro Leu Pro Asp Ser Ile Ile Gln Glu Ser Leu
                580                 585                 590
Glu Ile Gln Gln Gly Val Asn Pro Phe Phe Ile Gly Arg Ser Glu Asp
                595                 600                 605
Cys Asn Cys Lys Ile Glu Asp Asn Arg Leu Ser Arg Val His Cys Phe
            610                 615                 620
Ile Phe Lys Lys Arg His Ala Val Gly Lys Ser Met Tyr Glu Ser Pro
625                 630                 635                 640
Ala Gln Gly Leu Asp Asp Ile Trp Tyr Cys His Thr Gly Thr Asn Val
                645                 650                 655
Ser Tyr Leu Asn Asn Asn Arg Met Ile Gln Gly Thr Lys Phe Leu Leu
                660                 665                 670
Gln Asp Gly Asp Glu Ile Lys Ile Ile Trp Asp Lys Asn Asn Lys Phe
            675                 680                 685
Val Ile Gly Phe Lys Val Glu Ile Asn Asp Thr Thr Gly Leu Phe Asn
            690                 695                 700
Glu Gly Leu Gly Met Leu Gln Glu Gln Arg Val Val Leu Lys Gln Thr
705                 710                 715                 720
Ala Glu Glu Lys Asp Leu Val Lys Lys Leu Thr Gln Met Met Ala Ala
                725                 730                 735
Gln Arg Ala Asn Gln Pro Ser Ala Ser Ser Ser Met Ser Ala Lys
                740                 745                 750
Lys Pro Pro Val Ser Asp Thr Asn Asn Asn Gly Asn Asn Ser Val Leu
            755                 760                 765
Asn Asp Leu Val Glu Ser Pro Ile Ala Asn Thr Gly Asn Ile Leu
            770                 775                 780
Lys Arg Ile His Ser Val Ser Leu Ser Gln Ser Gln Ile Asp Pro Ser
785                 790                 795                 800
Lys Lys Val Lys Arg Ala Lys Leu Asp Gln Thr Ser Lys Gly Pro Glu
                805                 810                 815
Asn Leu Gln Phe Ser
            820

<210> SEQ ID NO 17
<211> LENGTH: 2525
<212> TYPE: DNA
<213> ORGANISM: Homo sapiens
<220> FEATURE:
<221> NAME/KEY: CDS
<222> LOCATION: (289)...(1230)

<400> SEQUENCE: 17
tcctgccccg cggcgctgcc gcacgagccc cacgagccgc tcaccccgcc gttctcagcg      60
ctgcccgacc ccgctggcgc gccctcccgc cgccagtccc ggcagcgccc tcagttgtcc     120
tccgactcgc cctcggcctt ccgcgccagc cgcagccaca gccgcaacgc cacccgcagc     180
cacagccaca gccacagccc caggcatagc cttcggcaca gccccggctc cggtcctgc      240 ggcagctcct ctgggcaccg tccctgcgcc gacatcctgg aggttggg atg ctc ttg      297
                                                    Met Leu Leu
```

-continued

```
                                1
tcc aaa atc aac tcg ctt gcc cac ctg cgc gcc gcg ccc tgc aac gac        345
Ser Lys Ile Asn Ser Leu Ala His Leu Arg Ala Ala Pro Cys Asn Asp
    5                  10                  15 ctg cac gcc acc aag ctg gcg ccc ggc aag gag aag gag ccc ctg gag        393
Leu His Ala Thr Lys Leu Ala Pro Gly Lys Glu Lys Glu Pro Leu Glu
 20                  25                  30                  35 tcg cag tac cag gtg ggc ccg cta ctg ggc agc ggc ggc ttc ggc tcg        441
Ser Gln Tyr Gln Val Gly Pro Leu Leu Gly Ser Gly Gly Phe Gly Ser
                 40                  45                  50 gtc tac tca ggc atc cgc gtc tcc gac aac ttg ccg gtg gcc atc aaa        489
Val Tyr Ser Gly Ile Arg Val Ser Asp Asn Leu Pro Val Ala Ile Lys
 55                  60                  65 cac gtg gag aag gac cgg att tcc gac tgg gga gag ctg cct aat ggc        537
His Val Glu Lys Asp Arg Ile Ser Asp Trp Gly Glu Leu Pro Asn Gly
             70                  75                  80 act cga gtg ccc atg gaa gtg gtc ctg ctg aag aag gtg agc tcg ggt        585
Thr Arg Val Pro Met Glu Val Val Leu Leu Lys Lys Val Ser Ser Gly
 85                  90                  95 ttc tcc ggc gtc att agg ctc ctg gac tgg ttc gag agg ccc gac agt        633
Phe Ser Gly Val Ile Arg Leu Leu Asp Trp Phe Glu Arg Pro Asp Ser
100                 105                 110                 115 ttc gtc ctg atc ctg gag agg ccc gag ccg gtg caa gat ctc ttc gac        681
Phe Val Leu Ile Leu Glu Arg Pro Glu Pro Val Gln Asp Leu Phe Asp
                120                 125                 130 ttc atc acg gaa agg gga gcc ctg caa gag gag ctc gcc cgc agc ttc        729
Phe Ile Thr Glu Arg Gly Ala Leu Gln Glu Glu Leu Ala Arg Ser Phe
            135                 140                 145 ttc tgg cag gtg ctg gag gcc gtg cgg cac tgc cac aac tgc ggg gtg        777
Phe Trp Gln Val Leu Glu Ala Val Arg His Cys His Asn Cys Gly Val
150                 155                 160 ctc cac cgc gac atc aag gac gaa aac atc ctt atc gac ctc aat cgc        825
Leu His Arg Asp Ile Lys Asp Glu Asn Ile Leu Ile Asp Leu Asn Arg
165                 170                 175 ggc gag ctc aag ctc atc gac ttc ggg tcg ggg gcg ctg ctc aaa gac        873
Gly Glu Leu Lys Leu Ile Asp Phe Gly Ser Gly Ala Leu Leu Lys Asp
180                 185                 190                 195 acc gtc tac acg gac ttc gat ggg acc cga gtg tat agc cct cca gag        921
Thr Val Tyr Thr Asp Phe Asp Gly Thr Arg Val Tyr Ser Pro Pro Glu
                200                 205                 210 tgg atc cgc tac cat cgc tac cat ggc agg tcg gcg gca gtc tgg tcc        969
Trp Ile Arg Tyr His Arg Tyr His Gly Arg Ser Ala Ala Val Trp Ser
            215                 220                 225 ctg ggg atc ctg ctg tat gat atg gtg tgt gga gat att cct ttc gag       1017
Leu Gly Ile Leu Leu Tyr Asp Met Val Cys Gly Asp Ile Pro Phe Glu
230                 235                 240 cat gac gaa gag atc atc agg ggc cag gtt ttc ttc agg cag agg gtc       1065
His Asp Glu Glu Ile Ile Arg Gly Gln Val Phe Phe Arg Gln Arg Val
245                 250                 255 tct tca gaa tgt cag cat ctc att aga tgg tgc ttg gcc ctg aga cca       1113
Ser Ser Glu Cys Gln His Leu Ile Arg Trp Cys Leu Ala Leu Arg Pro
260                 265                 270                 275 tca gat agg cca acc ttc gaa gaa atc cag aac cat cca tgg atg caa       1161
Ser Asp Arg Pro Thr Phe Glu Glu Ile Gln Asn His Pro Trp Met Gln
                280                 285                 290 gat gtt ctc ctg ccc cag gaa act gct gag atc cac ctc cac agc ctg       1209
Asp Val Leu Leu Pro Gln Glu Thr Ala Glu Ile His Leu His Ser Leu
            295                 300                 305 tcg ccg ggg ccc agc aaa tag cagcctttct ggcaggtcct ccctctctt          1260
```

```
Ser Pro Gly Pro Ser Lys   *
        310
```

```
gtcagatgcc cgagggaggg gaagcttctg tctccagctt cccgagtacc agtgacacgt    1320
ctcgccaagc aggacagtgc ttgatacagg aacaacattt acaactcatt ccagatccca    1380
ggcccctgga ggctgcctcc caacagtgag gaagagtgac tctccagggg tcctaggcct    1440
caactcctcc catagatact ctcttcttct cataggtgtc cagcattgct ggactgctga    1500
aatatcccgg gggtgggggg tggggtggg tcagaaccct gccatggaac tgtttccttc     1560
atcatgagtt ctgctgaatg ccgcgatggg tcaggtaggg gggaaacagg ttgggatggg    1620
ataggactag caccatttta agtccctgtc acctcttccg actctttctg agtgccttct    1680
gtggggactc cggctgtgct gggagaaata cttgaacttg cctctttttac ctgctgcttc   1740
tccaaaaatc tgcctgggtt ttgttcccta tttttctctc ctgtcctccc tcacccctc     1800
cttcatatga aggtgccat ggaagaggct acagggccaa acgctgagcc acctgccctt     1860
ttttctgcct cctttagtaa aactccgagt gaactggtct tccttttttgg ttttttactta  1920
actgttttcaa agccaagacc tcacacacag aaaaaatgca caaacaatgc aatcaacaga   1980
aaagctgtaa atgtgtgtac agttggcatg gtagtataca aaaagattgt agtggatcta   2040
attttttcaga aattttgcct ttaagttatt ttacctgttt ttgtttcttg ttttgaaaga   2100
tgcgcattct aacctggagg tcaatgttat gtatttattt atttatttat ttggttccct   2160
tcctattcca agcttccata gctgctgccc tagttttctt tcctcctttc ctcctctgac    2220
ttggggaacct tttgggggag ggctgcgacg cttgctctgt ttgtggggtg acgggactca   2280
ggcgggacag tgctgcagct ccctggcttc tgtggggccc ctcacctact tacccaggtg    2340
ggtcccggct ctgtgggtga tggggagggg cattgctgac tgtgtatata ggataattat    2400
gaaaagcagt tctggatggt gtgccttcca gatcctctct ggggctgtgt tttgagcagc    2460
aggtagcctg gctggtttta tctgagtgaa atactgtaca ggggaataaa agagatctta    2520
ttttt                                                                2525
```

```
<210> SEQ ID NO 18
<211> LENGTH: 313
<212> TYPE: PRT
<213> ORGANISM: Homo sapiens

<400> SEQUENCE: 18
```

```
Met Leu Leu Ser Lys Ile Asn Ser Leu Ala His Leu Arg Ala Ala Pro
  1               5                  10                  15

Cys Asn Asp Leu His Ala Thr Lys Leu Ala Pro Gly Lys Glu Lys Glu
                 20                  25                  30

Pro Leu Glu Ser Gln Tyr Gln Val Gly Pro Leu Leu Gly Ser Gly Gly
             35                  40                  45

Phe Gly Ser Val Tyr Ser Gly Ile Arg Val Ser Asp Asn Leu Pro Val
 50                  55                  60

Ala Ile Lys His Val Glu Lys Asp Arg Ile Ser Asp Trp Gly Glu Leu
 65                  70                  75                  80

Pro Asn Gly Thr Arg Val Pro Met Glu Val Val Leu Leu Lys Lys Val
                 85                  90                  95

Ser Ser Gly Phe Ser Gly Val Ile Arg Leu Leu Asp Trp Phe Glu Arg
            100                 105                 110

Pro Asp Ser Phe Val Leu Ile Leu Glu Arg Pro Glu Pro Val Gln Asp
            115                 120                 125
```

| | | | | | | | | | | | | |
|---|---|---|---|---|---|---|---|---|---|---|---|---|
|Leu|Phe|Asp|Phe|Ile|Thr|Glu|Arg|Gly|Ala|Leu|Gln|Glu|Glu|Leu|Ala|
| |130| | | | |135| | | | |140| | | | |

Leu Phe Asp Phe Ile Thr Glu Arg Gly Ala Leu Gln Glu Glu Leu Ala
         130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
    210                 215                 220

Val Trp Ser Leu Gly Ile Leu Leu Tyr Asp Met Val Cys Gly Asp Ile
225                 230                 235                 240

Pro Phe Glu His Asp Glu Glu Ile Ile Arg Gly Gln Val Phe Phe Arg
                245                 250                 255

Gln Arg Val Ser Ser Glu Cys Gln His Leu Ile Arg Trp Cys Leu Ala
            260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
    290                 295                 300

His Ser Leu Ser Pro Gly Pro Ser Lys
305                 310

<210> SEQ ID NO 19
<211> LENGTH: 3401
<212> TYPE: DNA
<213> ORGANISM: Saccharomyces cerevisiae
<220> FEATURE:
<221> NAME/KEY: CDS
<222> LOCATION: (789)...(2795)

<400> SEQUENCE: 19

```
atcgatacaa ctcccagaa atatcactgt tgagagttca tgtcaagacg tagtatagta    60
ttgcaacagg aaaaaaaat cttattgcgt agcactctgt atctatttta tatatctgtt   120
tctatatttg attaatctct tgttatcttg gtgatgatcg cacaagtatg tactcctgta   180
tctgcaagaa tatctgtttt aaacttttca aagcaaggaa accccgtctt atataggtta   240
tccgcaaagg tcacattttc ttgcaaatag aagaaaagc acccacaagc acactaacac   300
agtgccagag caaaactata tcctttgcat ccgatctcaa acgctgttct tatcgcatct   360
gtcttcgtcc tttcatctgc atttaccttt tcttttcat cctctatttg ccttttcatt   420
agtggcaatt tttccagttt tttccctctg cgtcccgttg cacctgaaag gatctttcta   480
acgtgtgttg tctactagtg agcgatttcg tgagccatac acgttctata gaaaattgaa   540
taaactttac ttcaaaggga tctggacaca gagataactg cttacctgct tgccggaaga   600
aaagaattac taaaaagaa gacaagggta gctgctattg tgggtacacg tttcacagaa   660 ctacttttc cttgtccttc tccagacatc aacgtcatac aactaaaact gataaagtac   720
ccgtttttcc gtacatttct atagatacat tattatatta gcagatcga gcgttaatt   780 tctcaaaag atg gaa gac aag ttt gct aac ctc agt ctc cat gag aaa act   830
                     Met Glu Asp Lys Phe Ala Asn Leu Ser Leu His Glu Lys Thr
                      1               5                  10 ggt aag tca tct atc caa tta aac gag caa aca ggc tca gat aat ggc   878
```

```
Gly Lys Ser Ser Ile Gln Leu Asn Glu Gln Thr Gly Ser Asp Asn Gly
 15                  20                  25                  30 tct gct gtc aag aga aca tct tcg acg tcc tcg cac tac aat aac atc        926
Ser Ala Val Lys Arg Thr Ser Ser Thr Ser Ser His Tyr Asn Asn Ile
                 35                  40                  45 aac gct gac ctt cat gct cgt gta aaa gct ttt caa gaa caa cgt gca        974
Asn Ala Asp Leu His Ala Arg Val Lys Ala Phe Gln Glu Gln Arg Ala
             50                  55                  60 ttg aaa agg tct gcc agc gtg ggc agt aat caa agc gag caa gac aaa       1022
Leu Lys Arg Ser Ala Ser Val Gly Ser Asn Gln Ser Glu Gln Asp Lys
         65                  70                  75 ggc agt tca caa tca cct aaa cat att cag cag att gtt aat aag cca       1070
Gly Ser Ser Gln Ser Pro Lys His Ile Gln Gln Ile Val Asn Lys Pro
     80                  85                  90 ttg ccg cct ctt ccc gta gca gga agt tct aag gtt tca caa aga atg       1118
Leu Pro Pro Leu Pro Val Ala Gly Ser Ser Lys Val Ser Gln Arg Met
 95                 100                 105                 110 agt agc caa gtc gtg caa gcg tcc tcc aag agc act ctt aag aac gtt       1166
Ser Ser Gln Val Val Gln Ala Ser Ser Lys Ser Thr Leu Lys Asn Val
                115                 120                 125 ctg gac aat caa gaa aca caa aac att acc gac gta aat att aac atc       1214
Leu Asp Asn Gln Glu Thr Gln Asn Ile Thr Asp Val Asn Ile Asn Ile
            130                 135                 140 gat aca acc aaa att acc gcc aca aca att ggt gta aat act ggc cta       1262
Asp Thr Thr Lys Ile Thr Ala Thr Thr Ile Gly Val Asn Thr Gly Leu
        145                 150                 155 cct gct act gac att acg ccg tca gtt tct aat act gca tca gca aca       1310
Pro Ala Thr Asp Ile Thr Pro Ser Val Ser Asn Thr Ala Ser Ala Thr
    160                 165                 170 cat aag gcg caa ttg ctg aat cct aac aga agg gca cca aga agg ccg       1358
His Lys Ala Gln Leu Leu Asn Pro Asn Arg Arg Ala Pro Arg Arg Pro
175                 180                 185                 190 ctt tct acc cag cac cct aca aga cca aat gtt gcc ccg cat aag gcc       1406
Leu Ser Thr Gln His Pro Thr Arg Pro Asn Val Ala Pro His Lys Ala
                195                 200                 205 cct gct ata atc aac aca cca aaa caa agt tta agt gcc cgt cga ggg       1454
Pro Ala Ile Ile Asn Thr Pro Lys Gln Ser Leu Ser Ala Arg Arg Gly
            210                 215                 220 ctc aaa tta cca cca gga gga atg tca tta aaa atg ccc act aaa aca       1502
Leu Lys Leu Pro Pro Gly Gly Met Ser Leu Lys Met Pro Thr Lys Thr
        225                 230                 235 gct caa cag ccg cag cag ttt gcc cca agc cct tca aac aaa aaa cat       1550
Ala Gln Gln Pro Gln Gln Phe Ala Pro Ser Pro Ser Asn Lys Lys His
    240                 245                 250 ata gaa acc tta tca aac agc aaa gtt gtt gaa ggg aaa aga tcg aat       1598
Ile Glu Thr Leu Ser Asn Ser Lys Val Val Glu Gly Lys Arg Ser Asn
255                 260                 265                 270 ccg ggt tct ttg ata aat ggt gtg caa agc aca tcc acc tca tca agt       1646
Pro Gly Ser Leu Ile Asn Gly Val Gln Ser Thr Ser Thr Ser Ser Ser
                275                 280                 285 acc gaa ggc cca cat gac act gta ggc act aca ccc aga act gga aac       1694
Thr Glu Gly Pro His Asp Thr Val Gly Thr Thr Pro Arg Thr Gly Asn
            290                 295                 300 agc aac aac tct tca aat tct ggt agt agt ggt ggt ggt ggt ctt ttc       1742
Ser Asn Asn Ser Ser Asn Ser Gly Ser Ser Gly Gly Gly Gly Leu Phe
        305                 310                 315 gca aat ttc tcg aaa tac gtg gat atc aaa tcc ggc tct ttg aat ttt       1790
Ala Asn Phe Ser Lys Tyr Val Asp Ile Lys Ser Gly Ser Leu Asn Phe
    320                 325                 330
```

```
gca ggc aaa cta tcg cta tcc tct aaa gga ata gat ttc agc aat ggt      1838
Ala Gly Lys Leu Ser Leu Ser Ser Lys Gly Ile Asp Phe Ser Asn Gly
335             340             345             350 tct agt tcg aga att aca ttg gac gaa cta gaa ttt ttg gat gaa ctg      1886
Ser Ser Ser Arg Ile Thr Leu Asp Glu Leu Glu Phe Leu Asp Glu Leu
                355             360             365 ggt cat ggt aac tat ggt aac gtc tca aag gta ctg cat aag ccc aca      1934
Gly His Gly Asn Tyr Gly Asn Val Ser Lys Val Leu His Lys Pro Thr
        370             375             380 aat gtt att atg gcg acg aag gaa gtc cgt ttg gag cta gat gag gct      1982
Asn Val Ile Met Ala Thr Lys Glu Val Arg Leu Glu Leu Asp Glu Ala
385             390             395 aaa ttt aga caa att tta atg gaa cta gaa gtt ttg cat aaa tgc aat      2030
Lys Phe Arg Gln Ile Leu Met Glu Leu Glu Val Leu His Lys Cys Asn
    400             405             410 tct ccc tat att gtg gat ttt tat ggt gca ttc ttt att gag ggc gcc      2078
Ser Pro Tyr Ile Val Asp Phe Tyr Gly Ala Phe Phe Ile Glu Gly Ala
415             420             425             430 gtc tac atg tgt atg gaa tac atg gat ggt ggt tcc ttg gat aaa ata      2126
Val Tyr Met Cys Met Glu Tyr Met Asp Gly Gly Ser Leu Asp Lys Ile
                435             440             445 tac gac gaa tca tct gaa atc ggc ggc att gat gaa cct cag cta gcg      2174
Tyr Asp Glu Ser Ser Glu Ile Gly Gly Ile Asp Glu Pro Gln Leu Ala
        450             455             460 ttt att gcc aat gct gtc att cat gga cta aaa gaa ctc aaa gag cag      2222
Phe Ile Ala Asn Ala Val Ile His Gly Leu Lys Glu Leu Lys Glu Gln
465             470             475 cat aat atc ata cac aga gat gtc aaa cca aca aat att tta tgt tca      2270
His Asn Ile Ile His Arg Asp Val Lys Pro Thr Asn Ile Leu Cys Ser
    480             485             490 gcc aac caa ggc acc gta aag ctg tgc gat ttc ggt gtt tct ggt aat      2318
Ala Asn Gln Gly Thr Val Lys Leu Cys Asp Phe Gly Val Ser Gly Asn
495             500             505             510 ttg gtg gca tct tta gcg aag act aat att ggt tgt cag tca tac atg      2366
Leu Val Ala Ser Leu Ala Lys Thr Asn Ile Gly Cys Gln Ser Tyr Met
                515             520             525 gca cct gaa cga atc aaa tcg ttg aat cca gat aga gcc acc tat acc      2414
Ala Pro Glu Arg Ile Lys Ser Leu Asn Pro Asp Arg Ala Thr Tyr Thr
        530             535             540 gta cag tca gac atc tgg tct tta ggt tta agc att ctg gaa atg gca      2462
Val Gln Ser Asp Ile Trp Ser Leu Gly Leu Ser Ile Leu Glu Met Ala
                545             550             555 cta ggt aga tat ccg tat cca cca gaa aca tac gac aac att ttc tct      2510
Leu Gly Arg Tyr Pro Tyr Pro Pro Glu Thr Tyr Asp Asn Ile Phe Ser
560             565             570 caa ttg agc gct att gtt gat ggg ccg cca ccg aga tta cct tca gat      2558
Gln Leu Ser Ala Ile Val Asp Gly Pro Pro Pro Arg Leu Pro Ser Asp
575             580             585             590 aaa ttc agt tct gac gca caa gat ttt gtt tct tta tgt cta caa aag      2606
Lys Phe Ser Ser Asp Ala Gln Asp Phe Val Ser Leu Cys Leu Gln Lys
                595             600             605 att ccg gaa aga aga cct aca tac gca gct tta aca gag cat cct tgg      2654
Ile Pro Glu Arg Arg Pro Thr Tyr Ala Ala Leu Thr Glu His Pro Trp
        610             615             620 tta gta aaa tac aga aac cag gat gtc cac atg agt gag tat atc act      2702
Leu Val Lys Tyr Arg Asn Gln Asp Val His Met Ser Glu Tyr Ile Thr
625             630             635 gaa cga tta gaa agg cgc aac aaa atc tta cgg gaa cgt ggt gag aat      2750
Glu Arg Leu Glu Arg Arg Asn Lys Ile Leu Arg Glu Arg Gly Glu Asn
                640             645             650
```

```
ggt tta tct aaa aat gta ccg gca tta cat atg ggt ggt tta tag     2795
Gly Leu Ser Lys Asn Val Pro Ala Leu His Met Gly Gly Leu *
655                 660                 665 cgttaatatc caaataaaag caaacaggca cgtgaatata acaacaaaaa aaaagcagac  2855
gaaaagctac tgtggaaatg atgcggcgaa tacaaaaaaa ccttacatat acatatgttt  2915
attgtaataa acttgcatta tactcgttat agacatatat atatatatat attcatatat  2975
atatatcgtc tgacttcctt ttgtcgaacc taaaaaaggg cacgaattat gacagagtat  3035
tgaggggatg ttatttcaag caccggcaag tgaagcgatg tggacgtcaa tatattgtgt  3095
tattcgatta ttgctacggc catcgactcc tcgaaattat ttacgttcgg ggctgacaac  3155
gcaagaaaga aaaatgctc tggaattgtc tgatggtttt tccgctcttt acggctcaag   3215
gctaggaaag aaaaaaaagt ccaaaatcat cgagaaaata aaaggtgttt tgaaagttca  3275
aatccacgtt attgagagta gatgtggagt ctggaccagg aactatacct gtatcttacc  3335
ctaacttcta aattttgcta ctttcacgga aaacagtaaa taattaccta tcaagataaa  3395
gagctc                                                            3401
```

<210> SEQ ID NO 20
<211> LENGTH: 668
<212> TYPE: PRT
<213> ORGANISM: Saccharomyces cerevisiae

<400> SEQUENCE: 20

```
Met Glu Asp Lys Phe Ala Asn Leu Ser Leu His Glu Lys Thr Gly Lys
1               5                   10                  15

Ser Ser Ile Gln Leu Asn Glu Gln Thr Gly Ser Asp Asn Gly Ser Ala
            20                  25                  30

Val Lys Arg Thr Ser Ser Thr Ser Ser His Tyr Asn Asn Ile Asn Ala
        35                  40                  45

Asp Leu His Ala Arg Val Lys Ala Phe Gln Glu Gln Arg Ala Leu Lys
    50                  55                  60

Arg Ser Ala Ser Val Gly Ser Asn Gln Ser Glu Gln Asp Lys Gly Ser
65                  70                  75                  80

Ser Gln Ser Pro Lys His Ile Gln Gln Ile Val Asn Lys Pro Leu Pro
                85                  90                  95

Pro Leu Pro Val Ala Gly Ser Ser Lys Val Ser Gln Arg Met Ser Ser
            100                 105                 110

Gln Val Val Gln Ala Ser Ser Lys Ser Thr Leu Lys Asn Val Leu Asp
        115                 120                 125

Asn Gln Glu Thr Gln Asn Ile Thr Asp Val Asn Ile Asn Ile Asp Thr
    130                 135                 140

Thr Lys Ile Thr Ala Thr Thr Ile Gly Val Asn Thr Gly Leu Pro Ala
145                 150                 155                 160

Thr Asp Ile Thr Pro Ser Val Ser Asn Thr Ala Ser Ala Thr His Lys
                165                 170                 175

Ala Gln Leu Leu Asn Pro Asn Arg Arg Ala Pro Arg Pro Leu Ser
            180                 185                 190

Thr Gln His Pro Thr Arg Pro Asn Val Ala Pro His Lys Ala Pro Ala
        195                 200                 205

Ile Ile Asn Thr Pro Lys Gln Ser Leu Ser Ala Arg Arg Gly Leu Lys
    210                 215                 220

Leu Pro Pro Gly Gly Met Ser Leu Lys Met Pro Thr Lys Thr Ala Gln
225                 230                 235                 240
```

```
Gln Pro Gln Gln Phe Ala Pro Ser Pro Ser Asn Lys Lys His Ile Glu
                245                 250                 255

Thr Leu Ser Asn Ser Lys Val Val Glu Gly Lys Arg Ser Asn Pro Gly
            260                 265                 270

Ser Leu Ile Asn Gly Val Gln Ser Thr Ser Thr Ser Ser Thr Glu
        275                 280                 285

Gly Pro His Asp Thr Val Gly Thr Thr Pro Arg Thr Gly Asn Ser Asn
            290                 295                 300

Asn Ser Ser Asn Ser Gly Ser Ser Gly Gly Gly Leu Phe Ala Asn
305                 310                 315                 320

Phe Ser Lys Tyr Val Asp Ile Lys Ser Gly Ser Leu Asn Phe Ala Gly
                325                 330                 335

Lys Leu Ser Leu Ser Ser Lys Gly Ile Asp Phe Ser Asn Gly Ser Ser
            340                 345                 350

Ser Arg Ile Thr Leu Asp Glu Leu Glu Phe Leu Asp Glu Leu Gly His
            355                 360                 365

Gly Asn Tyr Gly Asn Val Ser Lys Val Leu His Lys Pro Thr Asn Val
        370                 375                 380

Ile Met Ala Thr Lys Glu Val Arg Leu Glu Leu Asp Glu Ala Lys Phe
385                 390                 395                 400

Arg Gln Ile Leu Met Glu Leu Glu Val Leu His Lys Cys Asn Ser Pro
                405                 410                 415

Tyr Ile Val Asp Phe Tyr Gly Ala Phe Phe Ile Glu Gly Ala Val Tyr
            420                 425                 430

Met Cys Met Glu Tyr Met Asp Gly Gly Ser Leu Asp Lys Ile Tyr Asp
            435                 440                 445

Glu Ser Ser Glu Ile Gly Gly Ile Asp Glu Pro Gln Leu Ala Phe Ile
        450                 455                 460

Ala Asn Ala Val Ile His Gly Leu Lys Glu Leu Lys Glu Gln His Asn
465                 470                 475                 480

Ile Ile His Arg Asp Val Lys Pro Thr Asn Ile Leu Cys Ser Ala Asn
                485                 490                 495

Gln Gly Thr Val Lys Leu Cys Asp Phe Gly Val Ser Gly Asn Leu Val
            500                 505                 510

Ala Ser Leu Ala Lys Thr Asn Ile Gly Cys Gln Ser Tyr Met Ala Pro
            515                 520                 525

Glu Arg Ile Lys Ser Leu Asn Pro Asp Arg Ala Thr Tyr Thr Val Gln
        530                 535                 540

Ser Asp Ile Trp Ser Leu Gly Leu Ser Ile Leu Glu Met Ala Leu Gly
545                 550                 555                 560

Arg Tyr Pro Tyr Pro Pro Glu Thr Tyr Asp Asn Ile Phe Ser Gln Leu
                565                 570                 575

Ser Ala Ile Val Asp Gly Pro Pro Arg Leu Pro Ser Asp Lys Phe
            580                 585                 590

Ser Ser Asp Ala Gln Asp Phe Val Ser Leu Cys Leu Gln Lys Ile Pro
        595                 600                 605

Glu Arg Arg Pro Thr Tyr Ala Ala Leu Thr Glu His Pro Trp Leu Val
        610                 615                 620

Lys Tyr Arg Asn Gln Asp Val His Met Ser Glu Tyr Ile Thr Glu Arg
625                 630                 635                 640

Leu Glu Arg Arg Asn Lys Ile Leu Arg Glu Arg Gly Glu Asn Gly Leu
                645                 650                 655
```

```
Ser Lys Asn Val Pro Ala Leu His Met Gly Gly Leu
            660                 665

<210> SEQ ID NO 21
<211> LENGTH: 1883
<212> TYPE: DNA
<213> ORGANISM: Homo sapiens
<220> FEATURE:
<221> NAME/KEY: CDS
<222> LOCATION: (121)...(1203)

<400> SEQUENCE: 21
gtgagccacc gccccagcc  tggcctggca tttctttgag ttcaggaagt gtgacaagga      60
tttggacacc cagaaataag cgtgtcgaga agagcacaag cagaggatcc agcgctcggc     120 atg gcg gag cca gat ctg gag tgc gag cag atc cgt ctg aag tgt att      168
Met Ala Glu Pro Asp Leu Glu Cys Glu Gln Ile Arg Leu Lys Cys Ile
 1               5                  10                  15 cgt aag gag ggc ttc ttc acg gtg cct ccg gaa cac agg ctg gga cga      216
Arg Lys Glu Gly Phe Phe Thr Val Pro Pro Glu His Arg Leu Gly Arg
             20                  25                  30 tgc cgg agt gtg aag gag ttt gag aag ctg aac cgc att gga gag ggt      264
Cys Arg Ser Val Lys Glu Phe Glu Lys Leu Asn Arg Ile Gly Glu Gly
         35                  40                  45 acc tac ggc att gtg tat cgg gcc cgg gac acc cag aca gat gag att      312
Thr Tyr Gly Ile Val Tyr Arg Ala Arg Asp Thr Gln Thr Asp Glu Ile
     50                  55                  60 gtc gca ctg aag aag gtg cgg atg gac aag gag aag gat ggc atc ccc      360
Val Ala Leu Lys Lys Val Arg Met Asp Lys Glu Lys Asp Gly Ile Pro
 65                  70                  75                  80 atc agc agc ttg cgg gag atc acg ctg ctc cgc ctg cgt cat ccg          408
Ile Ser Ser Leu Arg Glu Ile Thr Leu Leu Arg Leu Arg His Pro
                 85                  90                  95 aac atc gtg gag ctg aag gag gtg gtt gtg ggg aac cac ctg gag agc      456
Asn Ile Val Glu Leu Lys Glu Val Val Val Gly Asn His Leu Glu Ser
            100                 105                 110 atc ttc ctg gtg atg ggt tac tgt gag cag gac ctg gcc agc ctc ctg      504
Ile Phe Leu Val Met Gly Tyr Cys Glu Gln Asp Leu Ala Ser Leu Leu
        115                 120                 125 gag aat atg cca aca ccc ttc tcg gag gct cag gtc aag tgc atc gtg      552
Glu Asn Met Pro Thr Pro Phe Ser Glu Ala Gln Val Lys Cys Ile Val
    130                 135                 140 ctg cag gtg ctc cgg ggc ctc cag tat ctg cac agg aac ttc att atc      600
Leu Gln Val Leu Arg Gly Leu Gln Tyr Leu His Arg Asn Phe Ile Ile
145                 150                 155                 160 cac agg gac ctg aag gtt tcc aac ttg ctc atg acc gac aag ggt tgt      648
His Arg Asp Leu Lys Val Ser Asn Leu Leu Met Thr Asp Lys Gly Cys
                165                 170                 175 gtg aag aca gcg gat ttc ggc ctg gcc cgg gcc tat ggt gtc cca gta      696
Val Lys Thr Ala Asp Phe Gly Leu Ala Arg Ala Tyr Gly Val Pro Val
            180                 185                 190 aag cca atg acc ccc aag gtg gtc act ctc tgg tac cga gcc cct gaa      744
Lys Pro Met Thr Pro Lys Val Val Thr Leu Trp Tyr Arg Ala Pro Glu
        195                 200                 205 ctg ctg ttg gga acc acc acg cag acc acc agc atc gac atg tgg gct      792
Leu Leu Leu Gly Thr Thr Thr Gln Thr Thr Ser Ile Asp Met Trp Ala
    210                 215                 220 gtg ggc tgc ata ctg gcc gag ctg ctg gcg cac agg cct ctt ctc ccc      840
Val Gly Cys Ile Leu Ala Glu Leu Leu Ala His Arg Pro Leu Leu Pro
225                 230                 235                 240 ggc act tcc gag atc cac cag atc gac ttg atc gtg cag ctg ctg ggc      888
```

-continued

```
Gly Thr Ser Glu Ile His Gln Ile Asp Leu Ile Val Gln Leu Leu Gly
            245                 250                 255 acg ccc agt gag aac atc tgg ccg ggc ttt tcc aag ctg cca ctg gtc       936
Thr Pro Ser Glu Asn Ile Trp Pro Gly Phe Ser Lys Leu Pro Leu Val
        260                 265                 270 ggc cag tac agc ctc cgg aag cag ccc tac aac aac ctg aag cac aag       984
Gly Gln Tyr Ser Leu Arg Lys Gln Pro Tyr Asn Asn Leu Lys His Lys
    275                 280                 285 ttc cca tgg ctg tcg gag gcc ggg ctg cgc ctg ctc cac ttc ctg ttc      1032
Phe Pro Trp Leu Ser Glu Ala Gly Leu Arg Leu Leu His Phe Leu Phe
290                 295                 300 atg tac gac cct aag aaa agg gcg acg gcc ggg gac tgc ctg gag agc      1080
Met Tyr Asp Pro Lys Lys Arg Ala Thr Ala Gly Asp Cys Leu Glu Ser
305                 310                 315                 320 tcc tat ttc aag gag aag ccc cta ccc tgt gag ccg gag ctc atg ccg      1128
Ser Tyr Phe Lys Glu Lys Pro Leu Pro Cys Glu Pro Glu Leu Met Pro
                325                 330                 335 acc ttt ccc cac cac cgc aac aag cgg gcc gcc cca gcc acc tcc gag      1176
Thr Phe Pro His His Arg Asn Lys Arg Ala Ala Pro Ala Thr Ser Glu
            340                 345                 350 ggc cag agc aag cgc tgt aaa ccc tga cggtgggcct ggcacacgcc            1223
Gly Gln Ser Lys Arg Cys Lys Pro  *
        355                 360 tgtattccca caccaggtct tccgatcagt ggtgtctgtg aagggtgccg cgagccaggc    1283
tgaccaggcg cccgggatcc agctcatccc cttggctggg aacatcctcc actgacttcc   1343
tcccactgtc tgccctgaac ccactgctgc cccagaaaaa aggccgggtg acaccggggg   1403
ctcccagccc gtgcaccctg gaagggcagg tctgcggct ccatccgtgg ctgcaggggt    1463
ctcatgtggt cctcctcgct atgttggaaa tgtgcaacca ctgcttcttg ggaggagtgg   1523
tgggtgcagt ccccccgctg tctttgagtt gtggtggacc gctggcctgg gatgagaggg   1583
cccagaagac cttcgtatcc cctctcagtc gcccgggggct gtcccgtgca tgggttggct  1643
gtggggaccc caggtgggcc tgcaggact ccagatgagg acaagaggga caaggtatgg    1703
ggtgggagca caattgagg ataccccgag ctaccaggag agccctgggc tggaggctga    1763
gctggatccc tgctccccac acggaggacc caacaggagg ccgtggctct gatgctgagc   1823
gaagctatag gctcttgttg gataaaagct ttttaacag aaaaaaaaaa aaaaaaaaa     1883
```

<210> SEQ ID NO 22
<211> LENGTH: 360
<212> TYPE: PRT
<213> ORGANISM: Homo sapiens

<400> SEQUENCE: 22

```
Met Ala Glu Pro Asp Leu Glu Cys Glu Gln Ile Arg Leu Lys Cys Ile
1               5                   10                  15

Arg Lys Glu Gly Phe Phe Thr Val Pro Pro Glu His Arg Leu Gly Arg
            20                  25                  30

Cys Arg Ser Val Lys Glu Phe Glu Lys Leu Asn Arg Ile Gly Glu Gly
        35                  40                  45

Thr Tyr Gly Ile Val Tyr Arg Ala Arg Asp Thr Gln Thr Asp Glu Ile
    50                  55                  60

Val Ala Leu Lys Lys Val Arg Met Asp Lys Glu Lys Asp Gly Ile Pro
65                  70                  75                  80

Ile Ser Ser Leu Arg Glu Ile Thr Leu Leu Leu Arg Leu Arg His Pro
                85                  90                  95
```

```
Asn Ile Val Glu Leu Lys Glu Val Val Gly Asn His Leu Glu Ser
                100                 105                 110
Ile Phe Leu Val Met Gly Tyr Cys Glu Gln Asp Leu Ala Ser Leu Leu
            115                 120                 125
Glu Asn Met Pro Thr Pro Phe Ser Glu Ala Gln Val Lys Cys Ile Val
        130                 135                 140
Leu Gln Val Leu Arg Gly Leu Gln Tyr Leu His Arg Asn Phe Ile Ile
145                 150                 155                 160
His Arg Asp Leu Lys Val Ser Asn Leu Leu Met Thr Asp Lys Gly Cys
                165                 170                 175
Val Lys Thr Ala Asp Phe Gly Leu Ala Arg Ala Tyr Gly Val Pro Val
            180                 185                 190
Lys Pro Met Thr Pro Lys Val Val Thr Leu Trp Tyr Arg Ala Pro Glu
        195                 200                 205
Leu Leu Leu Gly Thr Thr Thr Gln Thr Thr Ser Ile Asp Met Trp Ala
    210                 215                 220
Val Gly Cys Ile Leu Ala Glu Leu Leu Ala His Arg Pro Leu Leu Pro
225                 230                 235                 240
Gly Thr Ser Glu Ile His Gln Ile Asp Leu Ile Val Gln Leu Leu Gly
                245                 250                 255
Thr Pro Ser Glu Asn Ile Trp Pro Gly Phe Ser Lys Leu Pro Leu Val
            260                 265                 270
Gly Gln Tyr Ser Leu Arg Lys Gln Pro Tyr Asn Asn Leu Lys His Lys
        275                 280                 285
Phe Pro Trp Leu Ser Glu Ala Gly Leu Arg Leu Leu His Phe Leu Phe
    290                 295                 300
Met Tyr Asp Pro Lys Lys Arg Ala Thr Ala Gly Asp Cys Leu Glu Ser
305                 310                 315                 320
Ser Tyr Phe Lys Glu Lys Pro Leu Pro Cys Glu Pro Glu Leu Met Pro
                325                 330                 335
Thr Phe Pro His His Arg Asn Lys Arg Ala Ala Pro Ala Thr Ser Glu
            340                 345                 350
Gly Gln Ser Lys Arg Cys Lys Pro
        355                 360

<210> SEQ ID NO 23
<211> LENGTH: 2299
<212> TYPE: DNA
<213> ORGANISM: Mus musculus
<220> FEATURE:
<221> NAME/KEY: CDS
<222> LOCATION: (142)...(1698)

<400> SEQUENCE: 23
ccggacttcc atgggcagca gcagcggcag ggaacggagg gcgaatagat ttcagagcct       60
gcacctgaag tacaattcga atcctgctcc agggagcgca ccactgtccg gatccagaaa      120
ctttggccac tgggaggaaa a atg gcc agt gat acc cca ggt ttc tac atg        171
                         Met Ala Ser Asp Thr Pro Gly Phe Tyr Met
                           1               5                  10 gac aaa ctt aat aaa tac cgc cag atg cac gga gta gcc att acg tat        219
Asp Lys Leu Asn Lys Tyr Arg Gln Met His Gly Val Ala Ile Thr Tyr
             15                  20                  25 aaa gaa ctt agt act tcg gga cct cca cat gac aga agg ttt aca ttt        267
Lys Glu Leu Ser Thr Ser Gly Pro Pro His Asp Arg Arg Phe Thr Phe
         30                  35                  40 caa gtt tta ata gat gag aag gaa ttt gga gaa gcc aaa ggt aga tca        315
```

```
            Gln Val Leu Ile Asp Glu Lys Glu Phe Gly Glu Ala Lys Gly Arg Ser
                         45                  50                  55 aag acg gag gca aga aac gct gca gcc aaa tta gct gtt gat ata ctt              363
Lys Thr Glu Ala Arg Asn Ala Ala Ala Lys Leu Ala Val Asp Ile Leu
             60                  65                  70 gat aac gaa aac aag gtg gat tgt cac acg agt gca tgt gag caa ggc              411
Asp Asn Glu Asn Lys Val Asp Cys His Thr Ser Ala Cys Glu Gln Gly
 75                  80                  85                  90 ttg ttc gtt ggt aac tac ata ggc ctt gtc aat agc ttt gcc cag aag              459
Leu Phe Val Gly Asn Tyr Ile Gly Leu Val Asn Ser Phe Ala Gln Lys
                 95                 100                 105 aaa aag ctg tct gta aat tat gaa cag tgt gag ccc aac tct gag ttg              507
Lys Lys Leu Ser Val Asn Tyr Glu Gln Cys Glu Pro Asn Ser Glu Leu
            110                 115                 120 cct caa aga ttt att tgt aaa tgc aaa att ggg cag aca atg tat ggt              555
Pro Gln Arg Phe Ile Cys Lys Cys Lys Ile Gly Gln Thr Met Tyr Gly
        125                 130                 135 act ggt tca ggt gtc acc aaa cag gag gca aag cag ttg gct gcg aaa              603
Thr Gly Ser Gly Val Thr Lys Gln Glu Ala Lys Gln Leu Ala Ala Lys
140                 145                 150 gaa gcc tat cag aag ctg tta aag agc ccg ccg aaa act gcc gga aca              651
Glu Ala Tyr Gln Lys Leu Leu Lys Ser Pro Pro Lys Thr Ala Gly Thr
155                 160                 165                 170 tcc tct agc gtt gtc aca tct aca ttc agt ggc ttt tcc agc agc tcg              699
Ser Ser Ser Val Val Thr Ser Thr Phe Ser Gly Phe Ser Ser Ser Ser
                    175                 180                 185 tct atg aca agt aat ggt gtt tcc cag tca gca cct gga agt ttt tcc              747
Ser Met Thr Ser Asn Gly Val Ser Gln Ser Ala Pro Gly Ser Phe Ser
                190                 195                 200 tca gag aac gtg ttt acg aac ggt ctc gga gaa aat aaa agg aaa tca              795
Ser Glu Asn Val Phe Thr Asn Gly Leu Gly Glu Asn Lys Arg Lys Ser
            205                 210                 215 gga gta aaa gta tcc cct gat gat gtg caa aga aat aaa tat acc ttg              843
Gly Val Lys Val Ser Pro Asp Asp Val Gln Arg Asn Lys Tyr Thr Leu
        220                 225                 230 gac gcc agg ttt aac agc gat ttt gaa gac ata gaa gaa att ggc tta              891
Asp Ala Arg Phe Asn Ser Asp Phe Glu Asp Ile Glu Glu Ile Gly Leu
235                 240                 245                 250 ggt gga ttt ggt caa gtt ttc aaa gcg aaa cac aga att gat gga aag              939
Gly Gly Phe Gly Gln Val Phe Lys Ala Lys His Arg Ile Asp Gly Lys
                255                 260                 265 aga tac gct att aag cgc gtt aaa tat aac acg gag aag gcg gag cac              987
Arg Tyr Ala Ile Lys Arg Val Lys Tyr Asn Thr Glu Lys Ala Glu His
            270                 275                 280 gaa gta caa gcg ctg gca gaa ctc aat cac gtc aac att gtc caa tac             1035
Glu Val Gln Ala Leu Ala Glu Leu Asn His Val Asn Ile Val Gln Tyr
        285                 290                 295 cat agt tgt tgg gag gga gtt gac tat gat cct gag cac agc atg agt             1083
His Ser Cys Trp Glu Gly Val Asp Tyr Asp Pro Glu His Ser Met Ser
300                 305                 310 gat aca agt cga tac aaa acc cgg tgc ctc ttt att caa atg gaa ttc             1131
Asp Thr Ser Arg Tyr Lys Thr Arg Cys Leu Phe Ile Gln Met Glu Phe
315                 320                 325                 330 tgt gat aaa gga act ttg gag caa tgg atg aga aac aga aat cag agt             1179
Cys Asp Lys Gly Thr Leu Glu Gln Trp Met Arg Asn Arg Asn Gln Ser
                335                 340                 345 aaa gtg gac aaa gct ttg att ttg gac tta tat gaa caa atc gtg acc             1227
Lys Val Asp Lys Ala Leu Ile Leu Asp Leu Tyr Glu Gln Ile Val Thr
            350                 355                 360
```

```
gga gtg gag tat ata cac tcg aaa ggg tta att cac aga gat ctt aag      1275
Gly Val Glu Tyr Ile His Ser Lys Gly Leu Ile His Arg Asp Leu Lys
            365                 370                 375 cca ggt aat ata ttt tta gta gat gaa aga cac att aag atc gga gac      1323
Pro Gly Asn Ile Phe Leu Val Asp Glu Arg His Ile Lys Ile Gly Asp
        380                 385                 390 ttt ggc ctt gca aca gcc ctg gaa aat gat gga aaa tcc cga aca agg      1371
Phe Gly Leu Ala Thr Ala Leu Glu Asn Asp Gly Lys Ser Arg Thr Arg
395                 400                 405                 410 aga aca gga act ctt caa tac atg agt cca gaa cag tta ttt tta aag      1419
Arg Thr Gly Thr Leu Gln Tyr Met Ser Pro Glu Gln Leu Phe Leu Lys
                415                 420                 425 cac tat gga aaa gaa gtg gac atc ttt gct ttg ggc ctt att cta gct      1467
His Tyr Gly Lys Glu Val Asp Ile Phe Ala Leu Gly Leu Ile Leu Ala
            430                 435                 440 gaa ctt ctt cac acg tgc ttc acg gag tca gag aaa ata aag ttt ttc      1515
Glu Leu Leu His Thr Cys Phe Thr Glu Ser Glu Lys Ile Lys Phe Phe
        445                 450                 455 gaa agt cta aga aaa ggc gac ttc tct aat gat ata ttc gac aac aaa      1563
Glu Ser Leu Arg Lys Gly Asp Phe Ser Asn Asp Ile Phe Asp Asn Lys
    460                 465                 470 gaa aaa agc ctt cta aaa aaa cta ctc tca gag aaa ccc aag gac cga      1611
Glu Lys Ser Leu Leu Lys Lys Leu Leu Ser Glu Lys Pro Lys Asp Arg
475                 480                 485                 490 cct gag aca tct gaa atc ctg aag acc ttg gct gaa tgg agg aac atc      1659
Pro Glu Thr Ser Glu Ile Leu Lys Thr Leu Ala Glu Trp Arg Asn Ile
                495                 500                 505 tca gag aaa gaa aag aaa cac atg tta ggg cct ttc tga gaaaacattc      1708
Ser Glu Lys Glu Lys Lys His Met Leu Gly Pro Phe *
            510                 515 cttctgccgt ggttttcctt taacgatctg cagtctgagg ggagtatcag tgaatattat      1768
ccttcttttc ttaataccac tctcccagac aggttttggt tagggtgacc cacagacatt      1828
gtatttatta ggctatgaaa aagtatgccc atttcctcaa ttgttaattg ctgggcctgt      1888
ggctggctag ctagccaaat atgtaaatgc ttgtttctcg tctgcccaaa gagaaaggca      1948
ggctcctgtg tgggaagtca cagagccccc aaagccaact ggatgaggaa ggactctggc      2008
ttttggcata aaaagagct ggtagtcaga gctggggcag aaggtcctgc agacagacag      2068
acagacagac agacagagac acaaagacat ggactagaat ggaggaggga gggaggaagg      2128
gagggaggga gagagagaga gagaaagaaa gagagagaga ggacatggag acaaaatggc      2188
ttaagttagc tgggctacct gagagactgt cccagaaaac aggccaacaa ccttccttat      2248
gctatataga tgtctcagtg tctttatcat taaacaccaa gcaggagtgc t               2299

<210> SEQ ID NO 24
<211> LENGTH: 518
<212> TYPE: PRT
<213> ORGANISM: Mus musculus

<400> SEQUENCE: 24

Met Ala Ser Asp Thr Pro Gly Phe Tyr Met Asp Lys Leu Asn Lys Tyr
 1               5                  10                  15

Arg Gln Met His Gly Val Ala Ile Thr Tyr Lys Glu Leu Ser Thr Ser
            20                  25                  30

Gly Pro Pro His Asp Arg Arg Phe Thr Phe Gln Val Leu Ile Asp Glu
        35                  40                  45

Lys Glu Phe Gly Glu Ala Lys Gly Arg Ser Lys Thr Glu Ala Arg Asn
    50                  55                  60
```

-continued

```
Ala Ala Ala Lys Leu Ala Val Asp Ile Leu Asp Asn Glu Asn Lys Val
 65                  70                  75                  80

Asp Cys His Thr Ser Ala Cys Glu Gln Gly Leu Phe Val Gly Asn Tyr
                 85                  90                  95

Ile Gly Leu Val Asn Ser Phe Ala Gln Lys Lys Leu Ser Val Asn
            100                 105                 110

Tyr Glu Gln Cys Glu Pro Asn Ser Glu Leu Pro Gln Arg Phe Ile Cys
            115                 120                 125

Lys Cys Lys Ile Gly Gln Thr Met Tyr Gly Thr Gly Ser Gly Val Thr
130                 135                 140

Lys Gln Glu Ala Lys Gln Leu Ala Ala Lys Glu Ala Tyr Gln Lys Leu
145                 150                 155                 160

Leu Lys Ser Pro Pro Lys Thr Ala Gly Thr Ser Ser Val Val Thr
                165                 170                 175

Ser Thr Phe Ser Gly Phe Ser Ser Ser Ser Met Thr Ser Asn Gly
            180                 185                 190

Val Ser Gln Ser Ala Pro Gly Ser Phe Ser Ser Glu Asn Val Phe Thr
            195                 200                 205

Asn Gly Leu Gly Glu Asn Lys Arg Lys Ser Gly Val Lys Val Ser Pro
210                 215                 220

Asp Asp Val Gln Arg Asn Lys Tyr Thr Leu Asp Ala Arg Phe Asn Ser
225                 230                 235                 240

Asp Phe Glu Asp Ile Glu Glu Ile Gly Leu Gly Gly Phe Gly Gln Val
                245                 250                 255

Phe Lys Ala Lys His Arg Ile Asp Gly Lys Arg Tyr Ala Ile Lys Arg
            260                 265                 270

Val Lys Tyr Asn Thr Glu Lys Ala Glu His Glu Val Gln Ala Leu Ala
            275                 280                 285

Glu Leu Asn His Val Asn Ile Val Gln Tyr His Ser Cys Trp Glu Gly
290                 295                 300

Val Asp Tyr Asp Pro Glu His Ser Met Ser Asp Thr Ser Arg Tyr Lys
305                 310                 315                 320

Thr Arg Cys Leu Phe Ile Gln Met Glu Phe Cys Asp Lys Gly Thr Leu
                325                 330                 335

Glu Gln Trp Met Arg Asn Arg Asn Gln Ser Lys Val Asp Lys Ala Leu
            340                 345                 350

Ile Leu Asp Leu Tyr Glu Gln Ile Val Thr Gly Val Glu Tyr Ile His
            355                 360                 365

Ser Lys Gly Leu Ile His Arg Asp Leu Lys Pro Gly Asn Ile Phe Leu
370                 375                 380

Val Asp Glu Arg His Ile Lys Ile Gly Asp Phe Gly Leu Ala Thr Ala
385                 390                 395                 400

Leu Glu Asn Asp Gly Lys Ser Arg Thr Arg Arg Thr Gly Thr Leu Gln
                405                 410                 415

Tyr Met Ser Pro Glu Gln Leu Phe Leu Lys His Tyr Gly Lys Glu Val
            420                 425                 430

Asp Ile Phe Ala Leu Gly Leu Ile Leu Ala Glu Leu His Thr Cys
            435                 440                 445

Phe Thr Glu Ser Glu Lys Ile Lys Phe Glu Ser Leu Arg Lys Gly
            450                 455                 460

Asp Phe Ser Asn Asp Ile Phe Asp Asn Lys Glu Lys Ser Leu Leu Lys
465                 470                 475                 480
```

-continued

```
Lys Leu Leu Ser Glu Lys Pro Lys Asp Arg Pro Glu Thr Ser Glu Ile
            485                 490                 495
Leu Lys Thr Leu Ala Glu Trp Arg Asn Ile Ser Glu Lys Glu Lys Lys
        500                 505                 510
His Met Leu Gly Pro Phe
        515

<210> SEQ ID NO 25
<211> LENGTH: 2055
<212> TYPE: DNA
<213> ORGANISM: Homo sapiens
<220> FEATURE:
<221> NAME/KEY: CDS
<222> LOCATION: (211)...(1632)

<400> SEQUENCE: 25
caggaagact ctgagtccga cgttggccta cccagtcgga aggcagagct gcaatctagt      60
taactacctc ctttccccta gatttccttt cattctgctc aagtcttcgc ctgtgtccga     120
tccctatcta ctttctctcc tcttgtagca agcctcagac tccaggcttg agctaggttt     180 tgttttctc ctggtgagaa ttcgaagacc atg tct acg gaa ctc ttc tca tcc      234
                                 Met Ser Thr Glu Leu Phe Ser Ser
                                  1               5 aca aga gag gaa gga agc tct ggc tca gga ccc agt ttt agg tct aat       282
Thr Arg Glu Glu Gly Ser Ser Gly Ser Gly Pro Ser Phe Arg Ser Asn
         10                  15                  20 caa agg aaa atg tta aac ctg ctc ctg gag aga gac act tcc ttt acc       330
Gln Arg Lys Met Leu Asn Leu Leu Leu Glu Arg Asp Thr Ser Phe Thr
 25                  30                  35                  40 gtc tgt cca gat gtc cct aga act cca gtg ggc aaa ttt ctt ggt gat       378
Val Cys Pro Asp Val Pro Arg Thr Pro Val Gly Lys Phe Leu Gly Asp
                 45                  50                  55 tct gca aac cta agc att ttg tct gga gga acc cca aaa tgt tgc ctc       426
Ser Ala Asn Leu Ser Ile Leu Ser Gly Gly Thr Pro Lys Cys Cys Leu
             60                  65                  70 gat ctt tcg aat ctt agc agt ggg gag ata act gcc act cag ctt acc       474
Asp Leu Ser Asn Leu Ser Ser Gly Glu Ile Thr Ala Thr Gln Leu Thr
         75                  80                  85 act tct gca gac ctt gat gaa act ggt cac ctg gat tct tca gga ctt       522
Thr Ser Ala Asp Leu Asp Glu Thr Gly His Leu Asp Ser Ser Gly Leu
 90                  95                 100 cag gaa gtg cat tta gct ggg atg aat cat gac cag cac cta atg aaa       570
Gln Glu Val His Leu Ala Gly Met Asn His Asp Gln His Leu Met Lys
105                 110                 115                 120 tgt agc cca gca cag ctt ctt tgt agc act ccg aat ggt ttg gac cgt       618
Cys Ser Pro Ala Gln Leu Leu Cys Ser Thr Pro Asn Gly Leu Asp Arg
                125                 130                 135 ggc cat aga aag aga gat gca atg tgt agt tca tct gca aat aaa gaa       666
Gly His Arg Lys Arg Asp Ala Met Cys Ser Ser Ser Ala Asn Lys Glu
            140                 145                 150 aat gac aat gga aac ttg gtg gac agt gaa atg aaa tat ttg ggc agt       714
Asn Asp Asn Gly Asn Leu Val Asp Ser Glu Met Lys Tyr Leu Gly Ser
        155                 160                 165 ccc att act act gtt cca aaa ttg gat aaa aat cca aac cta gga gaa       762
Pro Ile Thr Thr Val Pro Lys Leu Asp Lys Asn Pro Asn Leu Gly Glu
    170                 175                 180 gac cag gca gaa gag att tca gat gaa tta atg gag ttt tcc ctg aaa       810
Asp Gln Ala Glu Glu Ile Ser Asp Glu Leu Met Glu Phe Ser Leu Lys
185                 190                 195                 200 gat caa gaa gca aag gtg agc aga agt ggc cta tat cgc tcc ccg tcg       858
```

```
          Asp Gln Glu Ala Lys Val Ser Arg Ser Gly Leu Tyr Arg Ser Pro Ser
                          205                 210                 215 atg cca gag aac ttg aac agg cca aga ctg aag cag gtg gaa aaa ttc        906
Met Pro Glu Asn Leu Asn Arg Pro Arg Leu Lys Gln Val Glu Lys Phe
            220                 225                 230 aag gac aac aca ata cca gat aaa gtt aaa aaa tat ttt tct ggc            954
Lys Asp Asn Thr Ile Pro Asp Lys Val Lys Lys Tyr Phe Ser Gly
                235                 240                 245 caa gga aag ctc agg aag ggc tta tgt tta aag aag aca gtc tct ctg       1002
Gln Gly Lys Leu Arg Lys Gly Leu Cys Leu Lys Lys Thr Val Ser Leu
        250                 255                 260 tgt gac att act atc act cag atg ctg gag gaa gat tct aac cag ggg       1050
Cys Asp Ile Thr Ile Thr Gln Met Leu Glu Glu Asp Ser Asn Gln Gly
265                 270                 275                 280 cac ctg att ggt gat ttt tcc aag gta tgt gcg ctg cca acc gtg tca       1098
His Leu Ile Gly Asp Phe Ser Lys Val Cys Ala Leu Pro Thr Val Ser
                    285                 290                 295 ggg aaa cac caa gat ctg aag tat gtc aac cca gaa aca gtg gct gcc       1146
Gly Lys His Gln Asp Leu Lys Tyr Val Asn Pro Glu Thr Val Ala Ala
                300                 305                 310 tta ctg tcg ggg aag ttc cag ggt ctg att gag aag ttt tat gtc att       1194
Leu Leu Ser Gly Lys Phe Gln Gly Leu Ile Glu Lys Phe Tyr Val Ile
            315                 320                 325 gat tgt cgc tat cca tat gag tat ctg gga gga cac atc cag gga gcc       1242
Asp Cys Arg Tyr Pro Tyr Glu Tyr Leu Gly Gly His Ile Gln Gly Ala
        330                 335                 340 tta aac tta tat agt cag gaa gaa ctg ttt aac ttc ttt ctg aag aag       1290
Leu Asn Leu Tyr Ser Gln Glu Glu Leu Phe Asn Phe Phe Leu Lys Lys
345                 350                 355                 360 ccc atc gtc cct ttg gac acc cag aag aga ata atc atc gtg ttc cac       1338
Pro Ile Val Pro Leu Asp Thr Gln Lys Arg Ile Ile Ile Val Phe His
                    365                 370                 375 tgt gaa ttc tcc tca gag agg ggc ccc cga atg tgc cgc tgt ctg cgt       1386
Cys Glu Phe Ser Ser Glu Arg Gly Pro Arg Met Cys Arg Cys Leu Arg
                380                 385                 390 gaa gag gac agg tct ctg aac cag tat cct gca ttg tac tac cca gag       1434
Glu Glu Asp Arg Ser Leu Asn Gln Tyr Pro Ala Leu Tyr Tyr Pro Glu
            395                 400                 405 cta tat atc ctt aaa ggc ggc tac aga gac ttc ttt cca gaa tat atg       1482
Leu Tyr Ile Leu Lys Gly Gly Tyr Arg Asp Phe Phe Pro Glu Tyr Met
        410                 415                 420 gaa ctg tgt gaa cca cag agc tac tgc cct atg cat cat cag gac cac       1530
Glu Leu Cys Glu Pro Gln Ser Tyr Cys Pro Met His His Gln Asp His
425                 430                 435                 440 aag act gag ttg ctg agg tgt cga agc cag agc aaa gtg cag gaa ggg       1578
Lys Thr Glu Leu Leu Arg Cys Arg Ser Gln Ser Lys Val Gln Glu Gly
                    445                 450                 455 gag cgg cag ctg cgg gag cag att gcc ctt ctg gtg aag gac atg agc       1626
Glu Arg Gln Leu Arg Glu Gln Ile Ala Leu Leu Val Lys Asp Met Ser
                460                 465                 470 cca tga taacattcca gccactggct gctaacaagt caccaaaaag acactgcaga        1682
Pro * aaccctgagc agaaagaggc cttctggatg ccaaaccca agattattaa aagatgtctc     1742
tgcaaaccaa caggctacca acttgtatcc aggcctggga atggattagg tttcagcaga    1802
gctgaaagct ggtggcagag tcctggagct ggctctataa ggcagccttg agttgcatag    1862
agatttgtat tggttcaggg aactctggca ttccttttcc caactcctca tgtcttctca    1922
caagccagcc aactctttct ctctgggctt cgggctatgc aagagcgttg tctaccttct    1982
```

```
ttctttgtat tttccttctt tgtttccccc tctttcttt ttaaaaatgg aaaaataaac    2042
actacagaat gag                                                      2055
```

<210> SEQ ID NO 26
<211> LENGTH: 473
<212> TYPE: PRT
<213> ORGANISM: Homo sapiens

<400> SEQUENCE: 26

```
Met Ser Thr Glu Leu Phe Ser Thr Arg Glu Glu Gly Ser Ser Gly
 1               5                  10                  15

Ser Gly Pro Ser Phe Arg Ser Asn Gln Arg Lys Met Leu Asn Leu
                20                  25                  30

Leu Glu Arg Asp Thr Ser Phe Thr Val Cys Pro Asp Val Pro Arg Thr
                35                  40                  45

Pro Val Gly Lys Phe Leu Gly Asp Ser Ala Asn Leu Ser Ile Leu Ser
                50                  55                  60

Gly Gly Thr Pro Lys Cys Cys Leu Asp Leu Ser Asn Leu Ser Ser Gly
65                  70                  75                  80

Glu Ile Thr Ala Thr Gln Leu Thr Thr Ser Ala Asp Leu Asp Glu Thr
                85                  90                  95

Gly His Leu Asp Ser Ser Gly Leu Gln Glu Val His Leu Ala Gly Met
                100                 105                 110

Asn His Asp Gln His Leu Met Lys Cys Ser Pro Ala Gln Leu Leu Cys
            115                 120                 125

Ser Thr Pro Asn Gly Leu Asp Arg Gly His Arg Lys Arg Asp Ala Met
130                 135                 140

Cys Ser Ser Ser Ala Asn Lys Glu Asn Asp Asn Gly Asn Leu Val Asp
145                 150                 155                 160

Ser Glu Met Lys Tyr Leu Gly Ser Pro Ile Thr Thr Val Pro Lys Leu
                165                 170                 175

Asp Lys Asn Pro Asn Leu Gly Glu Asp Gln Ala Glu Glu Ile Ser Asp
                180                 185                 190

Glu Leu Met Glu Phe Ser Leu Lys Asp Gln Glu Ala Lys Val Ser Arg
            195                 200                 205

Ser Gly Leu Tyr Arg Ser Pro Ser Met Pro Glu Asn Leu Asn Arg Pro
            210                 215                 220

Arg Leu Lys Gln Val Glu Lys Phe Lys Asp Asn Thr Ile Pro Asp Lys
225                 230                 235                 240

Val Lys Lys Lys Tyr Phe Ser Gly Gln Gly Lys Leu Arg Lys Gly Leu
                245                 250                 255

Cys Leu Lys Lys Thr Val Ser Leu Cys Asp Ile Thr Ile Thr Gln Met
                260                 265                 270

Leu Glu Glu Asp Ser Asn Gln Gly His Leu Ile Gly Asp Phe Ser Lys
            275                 280                 285

Val Cys Ala Leu Pro Thr Val Ser Gly Lys His Gln Asp Leu Lys Tyr
            290                 295                 300

Val Asn Pro Glu Thr Val Ala Ala Leu Leu Ser Gly Lys Phe Gln Gly
305                 310                 315                 320

Leu Ile Glu Lys Phe Tyr Val Ile Asp Cys Arg Tyr Pro Tyr Glu Tyr
                325                 330                 335

Leu Gly Gly His Ile Gln Gly Ala Leu Asn Leu Tyr Ser Gln Glu Glu
            340                 345                 350
```

```
Leu Phe Asn Phe Phe Leu Lys Lys Pro Ile Val Pro Leu Asp Thr Gln
        355                 360                 365
Lys Arg Ile Ile Ile Val Phe His Cys Glu Phe Ser Ser Glu Arg Gly
    370                 375                 380
Pro Arg Met Cys Arg Cys Leu Arg Glu Glu Asp Arg Ser Leu Asn Gln
385                 390                 395                 400
Tyr Pro Ala Leu Tyr Tyr Pro Glu Leu Tyr Ile Leu Lys Gly Gly Tyr
                405                 410                 415
Arg Asp Phe Phe Pro Glu Tyr Met Glu Leu Cys Glu Pro Gln Ser Tyr
            420                 425                 430
Cys Pro Met His His Gln Asp His Lys Thr Glu Leu Leu Arg Cys Arg
        435                 440                 445
Ser Gln Ser Lys Val Gln Glu Gly Glu Arg Gln Leu Arg Glu Gln Ile
    450                 455                 460
Ala Leu Leu Val Lys Asp Met Ser Pro
465                 470

<210> SEQ ID NO 27
<211> LENGTH: 17
<212> TYPE: PRT
<213> ORGANISM: Homo sapiens

<400> SEQUENCE: 27

Ser Gly Leu Tyr Arg Ser Pro Ser Met Pro Glu Asn Leu Asn Arg Pro
1               5                   10                  15
Arg

<210> SEQ ID NO 28
<211> LENGTH: 14
<212> TYPE: PRT
<213> ORGANISM: Homo sapiens

<400> SEQUENCE: 28

Gly Leu Tyr Arg Ser Pro Ser Met Pro Glu Asn Leu Asn Arg
1               5                   10

<210> SEQ ID NO 29
<211> LENGTH: 2295
<212> TYPE: DNA
<213> ORGANISM: Saccharomyces cerevisiae
<220> FEATURE:
<221> NAME/KEY: CDS
<222> LOCATION: (1)...(2295)

<400> SEQUENCE: 29 atg tca aca aac tca ttc cat gat tat gtg gat tta aaa tcg aga act     48
Met Ser Thr Asn Ser Phe His Asp Tyr Val Asp Leu Lys Ser Arg Thr
1               5                   10                  15 aat aca cga cag ttt tca gat gac gaa gag ttc act acg cct cca aaa     96
Asn Thr Arg Gln Phe Ser Asp Asp Glu Glu Phe Thr Thr Pro Pro Lys
                20                  25                  30 cta agc aat ttc gga tca gct tta ctt tcc cac aca gaa aaa act tca    144
Leu Ser Asn Phe Gly Ser Ala Leu Leu Ser His Thr Glu Lys Thr Ser
            35                  40                  45 gca tca gag ata tta tca agt cat aat aat gac aag atc gca aat cga    192
Ala Ser Glu Ile Leu Ser Ser His Asn Asn Asp Lys Ile Ala Asn Arg
        50                  55                  60 tta gaa gaa atg gac agg agt tca tca agg agt cac ccc cca ccg tca    240
Leu Glu Glu Met Asp Arg Ser Ser Ser Arg Ser His Pro Pro Pro Ser
65                  70                  75                  80
```

-continued

```
atg ggc aat ttg aca tcc ggt cat act agt acc tca tcg cat tca acc      288
Met Gly Asn Leu Thr Ser Gly His Thr Ser Thr Ser Ser His Ser Thr
                 85                  90                  95 ttg ttc gga cga tat ctg aga aat aat cac cag act agc atg acg acg      336
Leu Phe Gly Arg Tyr Leu Arg Asn Asn His Gln Thr Ser Met Thr Thr
            100                 105                 110 atg aac act agt gac ata gag ata aat gtt gga aat agt ctt gat aag      384
Met Asn Thr Ser Asp Ile Glu Ile Asn Val Gly Asn Ser Leu Asp Lys
        115                 120                 125 agt ttt gaa agg ata agg aat ttg cga caa aat atg aaa gaa gat att      432
Ser Phe Glu Arg Ile Arg Asn Leu Arg Gln Asn Met Lys Glu Asp Ile
    130                 135                 140 acg gca aag tat gct gaa agg aga agt aag aga ttt tta ata tcc aat      480
Thr Ala Lys Tyr Ala Glu Arg Arg Ser Lys Arg Phe Leu Ile Ser Asn
145                 150                 155                 160 agg aca acg aag ctg ggt cct gca aag aga gcg atg act ttg aca aat      528
Arg Thr Thr Lys Leu Gly Pro Ala Lys Arg Ala Met Thr Leu Thr Asn
                165                 170                 175 atc ttt gat gag gat gtg cct aac tct cca aac cag cca ata aat gca      576
Ile Phe Asp Glu Asp Val Pro Asn Ser Pro Asn Gln Pro Ile Asn Ala
            180                 185                 190 agg gag aca gtg gaa tta cca ctt gag gat tct cac caa aca aac ttt      624
Arg Glu Thr Val Glu Leu Pro Leu Glu Asp Ser His Gln Thr Asn Phe
        195                 200                 205 aaa gaa cga aga gag aat acg gat tat gat tca att gat ttt gga gat      672
Lys Glu Arg Arg Glu Asn Thr Asp Tyr Asp Ser Ile Asp Phe Gly Asp
    210                 215                 220 ttg aat cct atc cag tat att aaa aaa cat aat ctt ccc aca agt gac      720
Leu Asn Pro Ile Gln Tyr Ile Lys Lys His Asn Leu Pro Thr Ser Asp
225                 230                 235                 240 ctt cca cta ata tct caa atc tac ttt gat aaa caa aga gaa gaa aat      768
Leu Pro Leu Ile Ser Gln Ile Tyr Phe Asp Lys Gln Arg Glu Glu Asn
                245                 250                 255 aga caa gca gca ctc cga aaa cat agt tcc aga gaa ttg ctt tat aaa      816
Arg Gln Ala Ala Leu Arg Lys His Ser Ser Arg Glu Leu Leu Tyr Lys
            260                 265                 270 agt agg tct tct tcc tct tca ctt tct agt aac aac tta ttg gca aac      864
Ser Arg Ser Ser Ser Ser Ser Leu Ser Ser Asn Asn Leu Leu Ala Asn
        275                 280                 285 aag gac aat tct ata aca tcc aat aat ggt tct caa ccc agg cga aaa      912
Lys Asp Asn Ser Ile Thr Ser Asn Asn Gly Ser Gln Pro Arg Arg Lys
    290                 295                 300 gtt tct act gga tca tct tca tct aag tca tcg atc gaa ata aga aga      960
Val Ser Thr Gly Ser Ser Ser Ser Lys Ser Ser Ile Glu Ile Arg Arg
305                 310                 315                 320 gct ctc aag gag aat att gat act agc aat aac agc aat ttc aac agc     1008
Ala Leu Lys Glu Asn Ile Asp Thr Ser Asn Asn Ser Asn Phe Asn Ser
                325                 330                 335 cca att cat aaa att tat aaa gga att tcc aga aat aaa gat tcc gac     1056
Pro Ile His Lys Ile Tyr Lys Gly Ile Ser Arg Asn Lys Asp Ser Asp
            340                 345                 350 tcc gaa aaa aga gaa gta ctg cga aac ata agc ata aat gca aat cac     1104
Ser Glu Lys Arg Glu Val Leu Arg Asn Ile Ser Ile Asn Ala Asn His
        355                 360                 365 gct gat aat ctc ctt caa caa gag aat aag aga cta aaa cga tca ttg     1152
Ala Asp Asn Leu Leu Gln Gln Glu Asn Lys Arg Leu Lys Arg Ser Leu
    370                 375                 380 gat gat gca ata acg aat gag aat ata aac agt aaa aat cta gaa gta     1200
Asp Asp Ala Ile Thr Asn Glu Asn Ile Asn Ser Lys Asn Leu Glu Val
385                 390                 395                 400
```

```
ttt tac cat cga cct gct ccc aaa cct cca gtc acc aag aaa gtt gaa      1248
Phe Tyr His Arg Pro Ala Pro Lys Pro Pro Val Thr Lys Lys Val Glu
                405                 410                 415 att gtt gaa cct gca aag tcc gct tct tta tcg aat aat aga aat ata      1296
Ile Val Glu Pro Ala Lys Ser Ala Ser Leu Ser Asn Asn Arg Asn Ile
            420                 425                 430 att aca gta aat gac tcc cag tac gaa aaa ata gaa ctt ttg ggt aga      1344
Ile Thr Val Asn Asp Ser Gln Tyr Glu Lys Ile Glu Leu Leu Gly Arg
                435                 440                 445 ggt gga tcc tcc aga gtt tac aag gtg aaa gga tct ggc aat agg gta      1392
Gly Gly Ser Ser Arg Val Tyr Lys Val Lys Gly Ser Gly Asn Arg Val
        450                 455                 460 tac gcg ctc aaa agg gtg tct ttt gac gct ttt gac gat tca agt att      1440
Tyr Ala Leu Lys Arg Val Ser Phe Asp Ala Phe Asp Asp Ser Ser Ile
465                 470                 475                 480 gat gga ttc aaa gga gaa ata gaa ctt ctg gaa aaa ttg aaa gac caa      1488
Asp Gly Phe Lys Gly Glu Ile Glu Leu Leu Glu Lys Leu Lys Asp Gln
                485                 490                 495 aag cgt gta atc caa cta cta gat tat gaa atg ggg gat ggt tta ttg      1536
Lys Arg Val Ile Gln Leu Leu Asp Tyr Glu Met Gly Asp Gly Leu Leu
            500                 505                 510 tat ttg ata atg gaa tgt ggt gat cat gat ttg tca caa atc ctt aac      1584
Tyr Leu Ile Met Glu Cys Gly Asp His Asp Leu Ser Gln Ile Leu Asn
                515                 520                 525 caa aga agc ggc atg cca ctg gat ttt aat ttt gtt aga ttc tat aca      1632
Gln Arg Ser Gly Met Pro Leu Asp Phe Asn Phe Val Arg Phe Tyr Thr
        530                 535                 540 aag gaa atg ttg ctg tgc att aaa gta gtt cat gat gcg ggc ata gtt      1680
Lys Glu Met Leu Leu Cys Ile Lys Val Val His Asp Ala Gly Ile Val
545                 550                 555                 560 cat tcg gat tta aaa cct gca aat ttt gtt tta gtg aaa ggt atc tta      1728
His Ser Asp Leu Lys Pro Ala Asn Phe Val Leu Val Lys Gly Ile Leu
                565                 570                 575 aaa atc att gat ttt ggt ata gca aac gcg gta ccg gaa cat acg gtg      1776
Lys Ile Ile Asp Phe Gly Ile Ala Asn Ala Val Pro Glu His Thr Val
            580                 585                 590 aat ata tat cgt gaa act caa att ggg act cca aat tat atg gca cca      1824
Asn Ile Tyr Arg Glu Thr Gln Ile Gly Thr Pro Asn Tyr Met Ala Pro
                595                 600                 605 gaa gca cta gtt gct atg aat tac aca caa aat agt gag aac caa cat      1872
Glu Ala Leu Val Ala Met Asn Tyr Thr Gln Asn Ser Glu Asn Gln His
        610                 615                 620 gag gga aac aag tgg aaa gtg ggg aga cca tct gat atg tgg tca tgc      1920
Glu Gly Asn Lys Trp Lys Val Gly Arg Pro Ser Asp Met Trp Ser Cys
625                 630                 635                 640 ggt tgt att ata tat cag atg att tac ggg aaa ccc cca tat ggc agt      1968
Gly Cys Ile Ile Tyr Gln Met Ile Tyr Gly Lys Pro Pro Tyr Gly Ser
                645                 650                 655 ttc caa ggc caa aat agg ctg ttg gct att atg aat cct gat gtg aaa      2016
Phe Gln Gly Gln Asn Arg Leu Leu Ala Ile Met Asn Pro Asp Val Lys
            660                 665                 670 atc cca ttt cct gaa cat act agc aat aat gaa aag att cca aag tct      2064
Ile Pro Phe Pro Glu His Thr Ser Asn Asn Glu Lys Ile Pro Lys Ser
                675                 680                 685 gcc att gaa tta atg aaa gca tgt ctg tac agg aac cca gac aaa aga      2112
Ala Ile Glu Leu Met Lys Ala Cys Leu Tyr Arg Asn Pro Asp Lys Arg
        690                 695                 700 tgg act gtg gat aaa gtc ctg agt agc act ttc ctt caa cct ttt atg      2160
Trp Thr Val Asp Lys Val Leu Ser Ser Thr Phe Leu Gln Pro Phe Met
```

|     |     |     |     |     |     |     |     |     |     |     |     |      |
|-----|-----|-----|-----|-----|-----|-----|-----|-----|-----|-----|-----|------|
|     | 705 |     |     |     | 710 |     |     |     | 715 |     |     | 720  |
| ata | tcc | gga | tcg | att | atg | gaa | gac | ctt | att | agg | aat | gcc | gtt | aga | tat | 2208 |
| Ile | Ser | Gly | Ser | Ile | Met | Glu | Asp | Leu | Ile | Arg | Asn | Ala | Val | Arg | Tyr |      |
|     |     |     |     |     | 725 |     |     |     | 730 |     |     |     | 735 |     |     |      |
| ggc | tct | gag | aag | cct | cat | ata | tca | caa | gat | gat | ctc | aat | gat | gtg | gta | 2256 |
| Gly | Ser | Glu | Lys | Pro | His | Ile | Ser | Gln | Asp | Asp | Leu | Asn | Asp | Val | Val |      |
|     |     |     | 740 |     |     |     |     | 745 |     |     |     |     | 750 |     |     |      |
| gac | act | gtt | tta | agg | aaa | ttt | gca | gat | tac | aaa | att | tag |     |     |     | 2295 |
| Asp | Thr | Val | Leu | Arg | Lys | Phe | Ala | Asp | Tyr | Lys | Ile | *   |     |     |     |      |
|     |     |     | 755 |     |     |     |     | 760 |     |     |     |     |     |     |     |      |

<210> SEQ ID NO 30
<211> LENGTH: 764
<212> TYPE: PRT
<213> ORGANISM: Saccharomyces cerevisiae

<400> SEQUENCE: 30

Met Ser Thr Asn Ser Phe His Asp Tyr Val Asp Leu Lys Ser Arg Thr
1               5                   10                  15

Asn Thr Arg Gln Phe Ser Asp Asp Glu Glu Phe Thr Thr Pro Pro Lys
            20                  25                  30

Leu Ser Asn Phe Gly Ser Ala Leu Leu Ser His Thr Glu Lys Thr Ser
        35                  40                  45

Ala Ser Glu Ile Leu Ser His Asn Asn Asp Lys Ile Ala Asn Arg
    50                  55                  60

Leu Glu Glu Met Asp Arg Ser Ser Arg Ser His Pro Pro Pro Ser
65                  70                  75                  80

Met Gly Asn Leu Thr Ser Gly His Thr Ser Thr Ser Ser His Ser Thr
                85                  90                  95

Leu Phe Gly Arg Tyr Leu Arg Asn Asn His Gln Thr Ser Met Thr Thr
            100                 105                 110

Met Asn Thr Ser Asp Ile Glu Ile Asn Val Gly Asn Ser Leu Asp Lys
        115                 120                 125

Ser Phe Glu Arg Ile Arg Asn Leu Arg Gln Asn Met Lys Glu Asp Ile
    130                 135                 140

Thr Ala Lys Tyr Ala Glu Arg Arg Ser Lys Arg Phe Leu Ile Ser Asn
145                 150                 155                 160

Arg Thr Thr Lys Leu Gly Pro Ala Lys Arg Ala Met Thr Leu Thr Asn
                165                 170                 175

Ile Phe Asp Glu Asp Val Pro Asn Ser Pro Asn Gln Pro Ile Asn Ala
            180                 185                 190

Arg Glu Thr Val Glu Leu Pro Leu Glu Asp Ser His Gln Thr Asn Phe
        195                 200                 205

Lys Glu Arg Arg Glu Asn Thr Asp Tyr Asp Ser Ile Asp Phe Gly Asp
    210                 215                 220

Leu Asn Pro Ile Gln Tyr Ile Lys Lys His Asn Leu Pro Thr Ser Asp
225                 230                 235                 240

Leu Pro Leu Ile Ser Gln Ile Tyr Phe Asp Lys Gln Arg Glu Asn
                245                 250                 255

Arg Gln Ala Ala Leu Arg Lys His Ser Ser Arg Glu Leu Leu Tyr Lys
            260                 265                 270

Ser Arg Ser Ser Ser Ser Leu Ser Ser Asn Asn Leu Leu Ala Asn
        275                 280                 285

Lys Asp Asn Ser Ile Thr Ser Asn Asn Gly Ser Gln Pro Arg Arg Lys
    290                 295                 300

-continued

```
Val Ser Thr Gly Ser Ser Ser Lys Ser Ile Glu Ile Arg Arg
305                 310                 315                 320

Ala Leu Lys Glu Asn Ile Asp Thr Ser Asn Asn Ser Asn Phe Asn Ser
            325                 330                 335

Pro Ile His Lys Ile Tyr Lys Gly Ile Ser Arg Asn Lys Asp Ser Asp
            340                 345                 350

Ser Glu Lys Arg Glu Val Leu Arg Asn Ile Ser Ile Asn Ala Asn His
        355                 360                 365

Ala Asp Asn Leu Leu Gln Gln Glu Asn Lys Arg Leu Lys Arg Ser Leu
    370                 375                 380

Asp Asp Ala Ile Thr Asn Glu Asn Ile Asn Ser Lys Asn Leu Glu Val
385                 390                 395                 400

Phe Tyr His Arg Pro Ala Pro Lys Pro Pro Val Thr Lys Lys Val Glu
                405                 410                 415

Ile Val Glu Pro Ala Lys Ser Ala Ser Leu Ser Asn Asn Arg Asn Ile
            420                 425                 430

Ile Thr Val Asn Asp Ser Gln Tyr Glu Lys Ile Glu Leu Leu Gly Arg
        435                 440                 445

Gly Gly Ser Ser Arg Val Tyr Lys Val Lys Gly Ser Gly Asn Arg Val
    450                 455                 460

Tyr Ala Leu Lys Arg Val Ser Phe Asp Ala Phe Asp Asp Ser Ser Ile
465                 470                 475                 480

Asp Gly Phe Lys Gly Glu Ile Glu Leu Leu Glu Lys Leu Lys Asp Gln
                485                 490                 495

Lys Arg Val Ile Gln Leu Leu Asp Tyr Glu Met Gly Asp Gly Leu Leu
            500                 505                 510

Tyr Leu Ile Met Glu Cys Gly Asp His Asp Leu Ser Gln Ile Leu Asn
        515                 520                 525

Gln Arg Ser Gly Met Pro Leu Asp Phe Asn Phe Val Arg Phe Tyr Thr
    530                 535                 540

Lys Glu Met Leu Leu Cys Ile Lys Val Val His Asp Ala Gly Ile Val
545                 550                 555                 560

His Ser Asp Leu Lys Pro Ala Asn Phe Val Leu Val Lys Gly Ile Leu
                565                 570                 575

Lys Ile Ile Asp Phe Gly Ile Ala Asn Ala Val Pro Glu His Thr Val
            580                 585                 590

Asn Ile Tyr Arg Glu Thr Gln Ile Gly Thr Pro Asn Tyr Met Ala Pro
        595                 600                 605

Glu Ala Leu Val Ala Met Asn Tyr Thr Gln Asn Ser Glu Asn Gln His
    610                 615                 620

Glu Gly Asn Lys Trp Lys Val Gly Arg Pro Ser Asp Met Trp Ser Cys
625                 630                 635                 640

Gly Cys Ile Ile Tyr Gln Met Ile Tyr Gly Lys Pro Pro Tyr Gly Ser
                645                 650                 655

Phe Gln Gly Gln Asn Arg Leu Leu Ala Ile Met Asn Pro Asp Val Lys
            660                 665                 670

Ile Pro Phe Pro Glu His Thr Ser Asn Asn Glu Lys Ile Pro Lys Ser
        675                 680                 685

Ala Ile Glu Leu Met Lys Ala Cys Leu Tyr Arg Asn Pro Asp Lys Arg
    690                 695                 700

Trp Thr Val Asp Lys Val Leu Ser Ser Thr Phe Leu Gln Pro Phe Met
705                 710                 715                 720

Ile Ser Gly Ser Ile Met Glu Asp Leu Ile Arg Asn Ala Val Arg Tyr
```

```
                        725                 730                 735
Gly Ser Glu Lys Pro His Ile Ser Gln Asp Asp Leu Asn Asp Val Val
                740                 745                 750

Asp Thr Val Leu Arg Lys Phe Ala Asp Tyr Lys Ile
            755                 760

<210> SEQ ID NO 31
<211> LENGTH: 2079
<212> TYPE: DNA
<213> ORGANISM: Schizosaccharomyces pombe
<220> FEATURE:
<221> NAME/KEY: CDS
<222> LOCATION: (30)...(2066)

<400> SEQUENCE: 31
ggaatgctcg ttttttagta actgtgttt atg tct aag cgc aat cct cct gtg        53
                                 Met Ser Lys Arg Asn Pro Pro Val
                                  1               5 act aat atc gcg gac ttg gtg tca gat tct tcc tta gat gaa gac tcg       101
Thr Asn Ile Ala Asp Leu Val Ser Asp Ser Ser Leu Asp Glu Asp Ser
         10                  15                  20 ctt tct ttt ctc gaa gag ctt cag gat cca gaa tta tac ttc aaa aac       149
Leu Ser Phe Leu Glu Glu Leu Gln Asp Pro Glu Leu Tyr Phe Lys Asn
 25                  30                  35                  40 gac act ttc tct tcc aag agt agc cat tct gat ggc acc gtt act ggg       197
Asp Thr Phe Ser Ser Lys Ser Ser His Ser Asp Gly Thr Val Thr Gly
                 45                  50                  55 gat acg ttg cgt agg cag tca agc ggt gca act gct tta gag aga ttg       245
Asp Thr Leu Arg Arg Gln Ser Ser Gly Ala Thr Ala Leu Glu Arg Leu
             60                  65                  70 gtc tca cat cct cgt act aaa aat ttt gat ttg caa gga aat gga gga       293
Val Ser His Pro Arg Thr Lys Asn Phe Asp Leu Gln Gly Asn Gly Gly
         75                  80                  85 caa aat tct gct ttg aag gaa gtg aat act cca gca tat cag tca atg       341
Gln Asn Ser Ala Leu Lys Glu Val Asn Thr Pro Ala Tyr Gln Ser Met
     90                  95                 100 cac cat ttc gag cat tta ata aca ccc ttg ccc tct act aat gcg tct       389
His His Phe Glu His Leu Ile Thr Pro Leu Pro Ser Thr Asn Ala Ser
105                 110                 115                 120 cac agt gaa gtt tca ctc agt gca gga gtg aat gat ctc aat tct aat       437
His Ser Glu Val Ser Leu Ser Ala Gly Val Asn Asp Leu Asn Ser Asn
                125                 130                 135 tcg gag cat gat ttg tta cct aaa agt gta aac aaa acc ccc ggt tct       485
Ser Glu His Asp Leu Leu Pro Lys Ser Val Asn Lys Thr Pro Gly Ser
            140                 145                 150 tta tca att tca aga cga cga aga atc ggc aga att gga tta ggc cct       533
Leu Ser Ile Ser Arg Arg Arg Arg Ile Gly Arg Ile Gly Leu Gly Pro
        155                 160                 165 cca aag cgt gct gag tac acg ttg acg gat ccc tcg aag act tcc gat       581
Pro Lys Arg Ala Glu Tyr Thr Leu Thr Asp Pro Ser Lys Thr Ser Asp
    170                 175                 180 acc aaa aac tct aca gaa gca gat gag gat att gaa atg aaa tct cga       629
Thr Lys Asn Ser Thr Glu Ala Asp Glu Asp Ile Glu Met Lys Ser Arg
185                 190                 195                 200 gaa gta tca cca gct tcc aac tct gtt gct gca aca act tta aaa cct       677
Glu Val Ser Pro Ala Ser Asn Ser Val Ala Ala Thr Thr Leu Lys Pro
                205                 210                 215 ctg cag ctg cat aac act cct ttg caa aca tcc cag gag cat ccc aaa       725
Leu Gln Leu His Asn Thr Pro Leu Gln Thr Ser Gln Glu His Pro Lys
            220                 225                 230
```

```
cct tct ttt cat cct tct cag ttt gag agc tct ttt tct cct agg gtg      773
Pro Ser Phe His Pro Ser Gln Phe Glu Ser Ser Phe Ser Pro Arg Val
            235                 240                 245 cag ttt gat cac gat gtt gaa aga aga gct agt gaa ctt cat tct cgt      821
Gln Phe Asp His Asp Val Glu Arg Arg Ala Ser Glu Leu His Ser Arg
250                 255                 260 cca gtc acc gtt ttc caa gag cct cag cgt tct gct tct caa cca tat      869
Pro Val Thr Val Phe Gln Glu Pro Gln Arg Ser Ala Ser Gln Pro Tyr
265                 270                 275                 280 gaa tct cat gct ctt tct cca aag gtg gct ccg tta ttt gat aac agt      917
Glu Ser His Ala Leu Ser Pro Lys Val Ala Pro Leu Phe Asp Asn Ser
                285                 290                 295 caa gct act ccc ata ccc aag cgt cag cag gac gtt gtt act gtt gcc      965
Gln Ala Thr Pro Ile Pro Lys Arg Gln Gln Asp Val Val Thr Val Ala
            300                 305                 310 aat cta caa ttt atc aaa tta gga gtt gtt gga aag ggt gga agt agt     1013
Asn Leu Gln Phe Ile Lys Leu Gly Val Val Gly Lys Gly Gly Ser Ser
            315                 320                 325 atg gta tat cgc ata ttt tcc ccc gat aac agt cgt tta tac gct ttg     1061
Met Val Tyr Arg Ile Phe Ser Pro Asp Asn Ser Arg Leu Tyr Ala Leu
330                 335                 340 aaa gag gtg aac ttt att aat gca gac caa act act ata caa gga tac     1109
Lys Glu Val Asn Phe Ile Asn Ala Asp Gln Thr Thr Ile Gln Gly Tyr
345                 350                 355                 360 aag aac gaa att gca tta tta aga aag ctt tca ggc aat gat cgc ata     1157
Lys Asn Glu Ile Ala Leu Leu Arg Lys Leu Ser Gly Asn Asp Arg Ile
                365                 370                 375 att aaa tta tat gct gcc gaa gtt aat gat act tta ggg caa ctc aat     1205
Ile Lys Leu Tyr Ala Ala Glu Val Asn Asp Thr Leu Gly Gln Leu Asn
            380                 385                 390 atg gtg atg gaa tgc gga gaa acg gat tta gca aac ctt tta atg aaa     1253
Met Val Met Glu Cys Gly Glu Thr Asp Leu Ala Asn Leu Leu Met Lys
            395                 400                 405 aac atg aag aaa ccc att aat ctt aat ttc atc aga atg tat tgg gag     1301
Asn Met Lys Lys Pro Ile Asn Leu Asn Phe Ile Arg Met Tyr Trp Glu
410                 415                 420 caa atg cta gag gcg gtc cag gta gtt cat gat caa aat ata gtg cat     1349
Gln Met Leu Glu Ala Val Gln Val Val His Asp Gln Asn Ile Val His
425                 430                 435                 440 tcg gat ttg aag ccg gcc aat ttc ctg ctt gta gaa ggg aat ttg aag     1397
Ser Asp Leu Lys Pro Ala Asn Phe Leu Leu Val Glu Gly Asn Leu Lys
                445                 450                 455 ctg att gat ttt ggc att gcc aaa gca att ggt aat gac acc act aat     1445
Leu Ile Asp Phe Gly Ile Ala Lys Ala Ile Gly Asn Asp Thr Thr Asn
            460                 465                 470 atc cat cgt gat tcc cac atc ggt act att aat tat atg gca cct gaa     1493
Ile His Arg Asp Ser His Ile Gly Thr Ile Asn Tyr Met Ala Pro Glu
            475                 480                 485 gct ttg aca gac atg aat gct cac aca aac tct ggc gtg aaa ctc gta     1541
Ala Leu Thr Asp Met Asn Ala His Thr Asn Ser Gly Val Lys Leu Val
            490                 495                 500 aag ttg ggc agg ccc agc gac gtg tgg agt ttg gga tgt ata tta tat     1589
Lys Leu Gly Arg Pro Ser Asp Val Trp Ser Leu Gly Cys Ile Leu Tyr
505                 510                 515                 520 cag atg gtg tat ggg agg gcc ccg ttt gct cat cta aaa atg atc caa     1637
Gln Met Val Tyr Gly Arg Ala Pro Phe Ala His Leu Lys Met Ile Gln
                525                 530                 535 gct ata gca gct atc cct aat gaa caa tat cac att cat ttc ccc gaa     1685
Ala Ile Ala Ala Ile Pro Asn Glu Gln Tyr His Ile His Phe Pro Glu
            540                 545                 550
```

-continued

```
gtt gcc tta cct gct aat gct gtc cag gag aaa gag gga tcg ttg cca     1733
Val Ala Leu Pro Ala Asn Ala Val Gln Glu Lys Glu Gly Ser Leu Pro
            555                 560                 565 ggt gta act gtc ggg cct gat cta atg gat gtt atg aaa aga tgc ctg     1781
Gly Val Thr Val Gly Pro Asp Leu Met Asp Val Met Lys Arg Cys Leu
570                 575                 580 gaa agg gat caa cgg aag aga ctt aca ata ccg gaa ttg ctg gtt cat     1829
Glu Arg Asp Gln Arg Lys Arg Leu Thr Ile Pro Glu Leu Leu Val His
585                 590                 595                 600 ccc ttt tta aac cct ttg cca tcc tat ttg aca cct ttg gcc aaa aag     1877
Pro Phe Leu Asn Pro Leu Pro Ser Tyr Leu Thr Pro Leu Ala Lys Lys
                605                 610                 615 ccg tta cct gtt tct ggg cac acc aat aat gct cat cca ctt aga ctc     1925
Pro Leu Pro Val Ser Gly His Thr Asn Asn Ala His Pro Leu Arg Leu
            620                 625                 630 agc aca gaa atc tca gct tct caa tta tca atg att ata gaa agg tcg     1973
Ser Thr Glu Ile Ser Ala Ser Gln Leu Ser Met Ile Ile Glu Arg Ser
        635                 640                 645 gtg gag ttg agt aag cac aag cga tta aat aag gaa ctt att gat agc     2021
Val Glu Leu Ser Lys His Lys Arg Leu Asn Lys Glu Leu Ile Asp Ser
650                 655                 660 atg gct tat gat tgc gtt agc aat tta cga aaa atg cca gaa tag         2066
Met Ala Tyr Asp Cys Val Ser Asn Leu Arg Lys Met Pro Glu *
665                 670                 675 aggcactaaa ttt                                                       2079

<210> SEQ ID NO 32
<211> LENGTH: 678
<212> TYPE: PRT
<213> ORGANISM: Schizosaccharomyces pombe

<400> SEQUENCE: 32

Met Ser Lys Arg Asn Pro Val Thr Asn Ile Ala Asp Leu Val Ser
  1               5                  10                  15

Asp Ser Ser Leu Asp Glu Asp Ser Leu Ser Phe Leu Glu Glu Leu Gln
             20                  25                  30

Asp Pro Glu Leu Tyr Phe Lys Asn Asp Thr Phe Ser Ser Lys Ser Ser
         35                  40                  45

His Ser Asp Gly Thr Val Thr Gly Asp Thr Leu Arg Arg Gln Ser Ser
     50                  55                  60

Gly Ala Thr Ala Leu Glu Arg Leu Val Ser His Pro Arg Thr Lys Asn
 65                  70                  75                  80

Phe Asp Leu Gln Gly Asn Gly Gln Asn Ser Ala Leu Lys Glu Val
                 85                  90                  95

Asn Thr Pro Ala Tyr Gln Ser Met His His Phe Glu His Leu Ile Thr
            100                 105                 110

Pro Leu Pro Ser Thr Asn Ala Ser His Ser Glu Val Ser Leu Ser Ala
        115                 120                 125

Gly Val Asn Asp Leu Asn Ser Asn Ser Glu His Asp Leu Leu Pro Lys
    130                 135                 140

Ser Val Asn Lys Thr Pro Gly Ser Leu Ser Ile Ser Arg Arg Arg Arg
145                 150                 155                 160

Ile Gly Arg Ile Gly Leu Gly Pro Pro Lys Arg Ala Glu Tyr Thr Leu
                165                 170                 175

Thr Asp Pro Ser Lys Thr Ser Asp Thr Lys Asn Ser Thr Glu Ala Asp
            180                 185                 190
```

```
Glu Asp Ile Glu Met Lys Ser Arg Glu Val Ser Pro Ala Ser Asn Ser
        195                 200                 205

Val Ala Ala Thr Thr Leu Lys Pro Leu Gln Leu His Asn Thr Pro Leu
    210                 215                 220

Gln Thr Ser Gln Glu His Pro Lys Pro Ser Phe His Pro Ser Gln Phe
225                 230                 235                 240

Glu Ser Ser Phe Ser Pro Arg Val Gln Phe Asp His Asp Val Glu Arg
                245                 250                 255

Arg Ala Ser Glu Leu His Ser Arg Pro Val Thr Val Phe Gln Glu Pro
            260                 265                 270

Gln Arg Ser Ala Ser Gln Pro Tyr Glu Ser His Ala Leu Ser Pro Lys
        275                 280                 285

Val Ala Pro Leu Phe Asp Asn Ser Gln Ala Thr Pro Ile Pro Lys Arg
    290                 295                 300

Gln Gln Asp Val Val Thr Val Ala Asn Leu Gln Phe Ile Lys Leu Gly
305                 310                 315                 320

Val Val Gly Lys Gly Gly Ser Ser Met Val Tyr Arg Ile Phe Ser Pro
                325                 330                 335

Asp Asn Ser Arg Leu Tyr Ala Leu Lys Glu Val Asn Phe Ile Asn Ala
            340                 345                 350

Asp Gln Thr Thr Ile Gln Gly Tyr Lys Asn Glu Ile Ala Leu Leu Arg
        355                 360                 365

Lys Leu Ser Gly Asn Asp Arg Ile Ile Lys Leu Tyr Ala Ala Glu Val
    370                 375                 380

Asn Asp Thr Leu Gly Gln Leu Asn Met Val Met Glu Cys Gly Glu Thr
385                 390                 395                 400

Asp Leu Ala Asn Leu Leu Met Lys Asn Met Lys Lys Pro Ile Asn Leu
                405                 410                 415

Asn Phe Ile Arg Met Tyr Trp Glu Gln Met Leu Glu Ala Val Gln Val
            420                 425                 430

Val His Asp Gln Asn Ile Val His Ser Asp Leu Lys Pro Ala Asn Phe
        435                 440                 445

Leu Leu Val Glu Gly Asn Leu Lys Leu Ile Asp Phe Gly Ile Ala Lys
    450                 455                 460

Ala Ile Gly Asn Asp Thr Thr Asn Ile His Arg Asp Ser His Ile Gly
465                 470                 475                 480

Thr Ile Asn Tyr Met Ala Pro Glu Ala Leu Thr Asp Met Asn Ala His
                485                 490                 495

Thr Asn Ser Gly Val Lys Leu Val Lys Leu Gly Arg Pro Ser Asp Val
            500                 505                 510

Trp Ser Leu Gly Cys Ile Leu Tyr Gln Met Val Tyr Gly Arg Ala Pro
        515                 520                 525

Phe Ala His Leu Lys Met Ile Gln Ala Ile Ala Ala Ile Pro Asn Glu
    530                 535                 540

Gln Tyr His Ile His Phe Pro Glu Val Ala Leu Pro Ala Asn Ala Val
545                 550                 555                 560

Gln Glu Lys Glu Gly Ser Leu Pro Gly Val Thr Val Gly Pro Asp Leu
                565                 570                 575

Met Asp Val Met Lys Arg Cys Leu Glu Arg Asp Gln Arg Lys Arg Leu
            580                 585                 590

Thr Ile Pro Glu Leu Leu Val His Pro Phe Leu Asn Pro Leu Pro Ser
        595                 600                 605

Tyr Leu Thr Pro Leu Ala Lys Lys Pro Leu Pro Val Ser Gly His Thr
```

-continued

```
                   610                 615                 620
Asn Asn Ala His Pro Leu Arg Leu Ser Thr Glu Ile Ser Ala Ser Gln
625                 630                 635                 640

Leu Ser Met Ile Ile Glu Arg Ser Val Glu Leu Ser Lys His Lys Arg
                645                 650                 655

Leu Asn Lys Glu Leu Ile Asp Ser Met Ala Tyr Asp Cys Val Ser Asn
                660                 665                 670

Leu Arg Lys Met Pro Glu
        675

<210> SEQ ID NO 33
<211> LENGTH: 2263
<212> TYPE: DNA
<213> ORGANISM: Homo sapiens
<220> FEATURE:
<221> NAME/KEY: CDS
<222> LOCATION: (379)...(1491)

<400> SEQUENCE: 33
gatatcacag caacattgaa atgctaaaaa gtttttaaac actctcaatt tctaattcac     60
catgtcacag actggtgaaa aaaaaaaaaa aagcggccgc ttccccccgg ccgggccccc    120
gccgccccgc ggtccccaga gcgccaggcc cccgggggga gggagggagg gcgccgggcc    180
ggtgggagcc agcggcgcgc ggtgggaccc acggagcccc gcgacccgcc gagcctggag    240
ccgggccggc tcggggaagc cggctccagc ccggagcgaa cttcgcagcc cgtcgggggg    300
cggcggggag ggggcccgga gccggaggag ggggcggccg cgggcacccc cgcctgtgcc    360
ccggcgtccc cgggcacc atg ctg tcc aac tcc cag ggc cag agc ccg ccg      411
                    Met Leu Ser Asn Ser Gln Gly Gln Ser Pro Pro
                     1               5                  10 gtg ccg ttc ccc gcc ccg gcc ccg ccg cag ccc ccc acc cct gcc           459
Val Pro Phe Pro Ala Pro Ala Pro Pro Gln Pro Pro Thr Pro Ala
                 15                  20                  25 ctg ccg cac ccc ccg gcg cag ccg ccg ccg ccc ccg cag cag ttc           507
Leu Pro His Pro Pro Ala Gln Pro Pro Pro Pro Pro Gln Gln Phe
             30                  35                  40 ccg cag ttc cac gtc aag tcc ggc ctg cag atc aag aag aac gcc atc       555
Pro Gln Phe His Val Lys Ser Gly Leu Gln Ile Lys Lys Asn Ala Ile
             45                  50                  55 atc gat gac tac aag gtc acc agc cag gtc ctg ggg ctg ggc atc aac       603
Ile Asp Asp Tyr Lys Val Thr Ser Gln Val Leu Gly Leu Gly Ile Asn
60                  65                  70                  75 ggc aaa gtt ttg cag atc ttc aac aag agg acc cag gag aaa ttc gcc       651
Gly Lys Val Leu Gln Ile Phe Asn Lys Arg Thr Gln Glu Lys Phe Ala
                80                  85                  90 ctc aaa atg ctt cag gac tgc ccc aag gcc cgc agg gag gtg gag ctg       699
Leu Lys Met Leu Gln Asp Cys Pro Lys Ala Arg Arg Glu Val Glu Leu
            95                 100                 105 cac tgg cgg gcc tcc cag tgc ccg cac atc gta cgg atc gtg gat gtg       747
His Trp Arg Ala Ser Gln Cys Pro His Ile Val Arg Ile Val Asp Val
        110                 115                 120 tac gag aat ctg tac gca ggg agg aag tgc ctg ctg att gtc atg gaa       795
Tyr Glu Asn Leu Tyr Ala Gly Arg Lys Cys Leu Leu Ile Val Met Glu
        125                 130                 135 tgt ttg gac ggt gga gaa ctc ttt agc cga atc cag gat cga gga gac       843
Cys Leu Asp Gly Gly Glu Leu Phe Ser Arg Ile Gln Asp Arg Gly Asp
140                 145                 150                 155 cag gca ttc aca gaa aga gaa gca tcc gaa atc atg aag agc atc ggt       891
Gln Ala Phe Thr Glu Arg Glu Ala Ser Glu Ile Met Lys Ser Ile Gly
```

-continued

```
                160                 165                 170
gag gcc atc cag tat ctg cat tca atc aac att gcc cat cgg gat gtc    939
Glu Ala Ile Gln Tyr Leu His Ser Ile Asn Ile Ala His Arg Asp Val
            175                 180                 185 aag cct gag aat ctc tta tac acc tcc aaa agg ccc aac gcc atc ctg    987
Lys Pro Glu Asn Leu Leu Tyr Thr Ser Lys Arg Pro Asn Ala Ile Leu
        190                 195                 200 aaa ctc act gac ttt ggc ttt gcc aag gaa acc acc agc cac aac tct   1035
Lys Leu Thr Asp Phe Gly Phe Ala Lys Glu Thr Thr Ser His Asn Ser
    205                 210                 215 ttg acc act cct tgt tat aca ccg tac tat gtg gct cca gaa gtg ctg   1083
Leu Thr Thr Pro Cys Tyr Thr Pro Tyr Tyr Val Ala Pro Glu Val Leu
220                 225                 230                 235 ggt cca gag aag tat gac aag tcc tgt gac atg tgg tcc ctg ggt gtc   1131
Gly Pro Glu Lys Tyr Asp Lys Ser Cys Asp Met Trp Ser Leu Gly Val
                240                 245                 250 atc atg tac atc ctg ctg tgt ggg tat ccc ccc ttc tac tcc aac cac   1179
Ile Met Tyr Ile Leu Leu Cys Gly Tyr Pro Pro Phe Tyr Ser Asn His
            255                 260                 265 ggc ctt gcc atc tct ccg ggc atg aag act cgc atc cga atg ggc cag   1227
Gly Leu Ala Ile Ser Pro Gly Met Lys Thr Arg Ile Arg Met Gly Gln
        270                 275                 280 tat gaa ttt ccc aac cca gaa tgg tca gaa gta tca gag gaa gtg aag   1275
Tyr Glu Phe Pro Asn Pro Glu Trp Ser Glu Val Ser Glu Glu Val Lys
    285                 290                 295 atg ctc att cgg aat ctg ctg aaa aca gag ccc acc cag aga atg acc   1323
Met Leu Ile Arg Asn Leu Leu Lys Thr Glu Pro Thr Gln Arg Met Thr
300                 305                 310                 315 atc acc gag ttt atg aac cac cct tgg atc atg caa tca aca aag gtc   1371
Ile Thr Glu Phe Met Asn His Pro Trp Ile Met Gln Ser Thr Lys Val
                320                 325                 330 cct caa acc cca ctg cac acc agc cgg gtc ctg aag gag gac aag gag   1419
Pro Gln Thr Pro Leu His Thr Ser Arg Val Leu Lys Glu Asp Lys Glu
            335                 340                 345 cgg tgg gag gat gtc aag ggg tgt ctt cat gac aag aac agc gac cag   1467
Arg Trp Glu Asp Val Lys Gly Cys Leu His Asp Lys Asn Ser Asp Gln
        350                 355                 360 gcc act tgg ctg acc agg ttg tga gcagaggatt ctgtgttcct gtccaaactc   1521
Ala Thr Trp Leu Thr Arg Leu  *
    365                 370 agtgctgttt cttagaatcc ttttattccc tgggtctcta atgggacctt aaagaccatc   1581
tggtatcatc ttctcatttt gcagaagaga aactgaggcc cagaggcgga gggcagtctg   1641
ctcaaggtca cgcagctggt gactggttgg ggcagaccgg acccaggttt cctgactcct   1701
ggcccaagtc tcttcctcct atcctgcggg atcactgggg ggctctcagg aacagcagc    1761 agtgccatag ccaggctctc tgctgcccag cgctggggtg aggctgccgt tgtcagcgtg   1821
gaccactaac cagcccgtct tctctctctg ctcccacccc tgccgccctc accctgccct   1881
tgttgtctct gtctctcacg tctctcttct gctgtctctc ctacctgtct tctggctctc   1941
tctgtaccct tcctggtgct gccgtgcccc caggaggaga tgaccagtgc cttggccaca   2001
atgcgcgttg actacgagca gatcaagata aaaagattg aagatgcatc caaccctctg    2061
ctgctgaaga ggcggaagaa agctcgggcc ctggaggctg cggctctggc ccactgagcc   2121
accgcgccct cctgcccacg ggaggacaag caataactct ctacaggaat atatttttta   2181
aacgaagaga cagaactgtc cacatctgcc tcctctcctc ctcagctgca tggagcctgg   2241
aactgcatca gtgactgaat tc                                           2263
```

<210> SEQ ID NO 34
<211> LENGTH: 370
<212> TYPE: PRT
<213> ORGANISM: Homo sapiens

<400> SEQUENCE: 34

Met Leu Ser Asn Ser Gln Gly Gln Ser Pro Pro Val Pro Phe Pro Ala
1               5                   10                  15

Pro Ala Pro Pro Gln Pro Thr Pro Ala Leu Pro His Pro Pro
            20                  25                  30

Ala Gln Pro Pro Pro Pro Gln Gln Phe Pro Gln Phe His Val
        35                  40                  45

Lys Ser Gly Leu Gln Ile Lys Lys Asn Ala Ile Ile Asp Asp Tyr Lys
    50                  55                  60

Val Thr Ser Gln Val Leu Gly Leu Gly Ile Asn Gly Lys Val Leu Gln
65                  70                  75                  80

Ile Phe Asn Lys Arg Thr Gln Glu Lys Phe Ala Leu Lys Met Leu Gln
                85                  90                  95

Asp Cys Pro Lys Ala Arg Arg Glu Val Glu Leu His Trp Arg Ala Ser
            100                 105                 110

Gln Cys Pro His Ile Val Arg Ile Val Asp Val Tyr Glu Asn Leu Tyr
        115                 120                 125

Ala Gly Arg Lys Cys Leu Leu Ile Val Met Glu Cys Leu Asp Gly Gly
    130                 135                 140

Glu Leu Phe Ser Arg Ile Gln Asp Arg Gly Asp Gln Ala Phe Thr Glu
145                 150                 155                 160

Arg Glu Ala Ser Glu Ile Met Lys Ser Ile Gly Glu Ala Ile Gln Tyr
                165                 170                 175

Leu His Ser Ile Asn Ile Ala His Arg Asp Val Lys Pro Glu Asn Leu
            180                 185                 190

Leu Tyr Thr Ser Lys Arg Pro Asn Ala Ile Leu Lys Leu Thr Asp Phe
        195                 200                 205

Gly Phe Ala Lys Glu Thr Thr Ser His Asn Ser Leu Thr Thr Pro Cys
    210                 215                 220

Tyr Thr Pro Tyr Tyr Val Ala Pro Glu Val Leu Gly Pro Glu Lys Tyr
225                 230                 235                 240

Asp Lys Ser Cys Asp Met Trp Ser Leu Gly Val Ile Met Tyr Ile Leu
                245                 250                 255

Leu Cys Gly Tyr Pro Pro Phe Tyr Ser Asn His Gly Leu Ala Ile Ser
            260                 265                 270

Pro Gly Met Lys Thr Arg Ile Arg Met Gly Gln Tyr Glu Phe Pro Asn
        275                 280                 285

Pro Glu Trp Ser Glu Val Ser Glu Glu Val Lys Met Leu Ile Arg Asn
    290                 295                 300

Leu Leu Lys Thr Glu Pro Thr Gln Arg Met Thr Ile Thr Glu Phe Met
305                 310                 315                 320

Asn His Pro Trp Ile Met Gln Ser Thr Lys Val Pro Gln Thr Pro Leu
                325                 330                 335

His Thr Ser Arg Val Leu Lys Glu Asp Lys Glu Arg Trp Glu Asp Val
            340                 345                 350

Lys Gly Cys Leu His Asp Lys Asn Ser Asp Gln Ala Thr Trp Leu Thr
        355                 360                 365

Arg Leu

<210> SEQ ID NO 35
<211> LENGTH: 1074
<212> TYPE: DNA
<213> ORGANISM: Homo sapiens
<220> FEATURE:
<221> NAME/KEY: CDS
<222> LOCATION: (628)...(831)

<400> SEQUENCE: 35

```
ttttactttt tttaagcaca aaattttgtt ttttttctcc cctccccaca gatcccatct      60
caaatcattc tgttaaccac cattccaaca ggtcgaggag agcttaaaca ccttcttcct     120
ctgccttgtt tctattttt tatttttttg catcagtatt aatgttttg catactctcc      180 atctttatcc aaaaatgtaa acttcctttg tcaatctatg gatatgccca tatatgaaag     240
agatgggtgg gtcaaaaagg gatatcaaat gaagtgatag gggtcacaat ggggaaatgg     300
aagtggtaca taacattgcc aaaataatgt gccactagaa atggtgtaaa ggctgtcttt     360
ttttttaaga aaagttatta ccatgtattt tgtgaggcag gtttacaaca ctacaagtct     420
tgactaagaa ggaaagagga aaaagaaaa aacaccaata cccatattta aaaaaaaaa      480 aatgatcata gtcttaggag ttcatttaaa ccataggaac ttttcactta tctcatgtta     540
ggtgtaccag tcagtgatta agtagaacta caagttatat aggctgtatt gtttattgct     600
ggtttatgac cttaataaag tgtaatt atg tat tac cag cag ggt gtt ttt aac    654
                               Met Tyr Tyr Gln Gln Gly Val Phe Asn
                                 1               5 tgt gac tat tgt ata aaa aca aat ctt gat atc cag aag cac atg aag    702
Cys Asp Tyr Cys Ile Lys Thr Asn Leu Asp Ile Gln Lys His Met Lys
 10              15                  20                  25 ttt gcg act ttc cac cct gcc cat ttt tgt aaa act gca gtc atc ttg    750
Phe Ala Thr Phe His Pro Ala His Phe Cys Lys Thr Ala Val Ile Leu
             30                  35                  40 gac ctt tta aac aca aat ttt aaa ctc aac caa gct gtg ata agc gga    798
Asp Leu Leu Asn Thr Asn Phe Lys Leu Asn Gln Ala Val Ile Ser Gly
         45                  50                  55 atg gtt act gtt tat act gtg gta tgt ttt tga ttacagcaga taatgctttc   851
Met Val Thr Val Tyr Thr Val Val Cys Phe *
         60                  65 ttttccagtc atctttgaga ataaaggaaa aaaaaaatct tcagatgcaa tggttttgtg    911
tagcatcttg tctatcatgt tttgtaaatg ctggagaagc gtcgaccaat ttgacttaga    971
gatggaatgt aactttgctt acaaaaattg ctattaaact cctacttaag gtgttctaat   1031
tttctgtgag cacactaaaa acaaaaatat atgtgaataa aat                    1074
```

<210> SEQ ID NO 36
<211> LENGTH: 67
<212> TYPE: PRT
<213> ORGANISM: Homo sapiens

<400> SEQUENCE: 36

```
Met Tyr Tyr Gln Gln Gly Val Phe Asn Cys Asp Tyr Cys Ile Lys Thr
  1               5                  10                  15

Asn Leu Asp Ile Gln Lys His Met Lys Phe Ala Thr Phe His Pro Ala
             20                  25                  30

His Phe Cys Lys Thr Ala Val Ile Leu Asp Leu Leu Asn Thr Asn Phe
         35                  40                  45

Lys Leu Asn Gln Ala Val Ile Ser Gly Met Val Thr Val Tyr Thr Val
```

Val Cys Phe
65

<210> SEQ ID NO 37
<211> LENGTH: 1356
<212> TYPE: DNA
<213> ORGANISM: Homo sapiens
<220> FEATURE:
<221> NAME/KEY: CDS
<222> LOCATION: (553)...(1095)

<400> SEQUENCE: 37

```
ttctcccgca accttccctt cgctccctcc cgtccccccc agctcctagc ctccgactcc      60
ctccccccct cacgcccgcc ctctcgcctt cgccgaacca agtggattaa ttacacgct     120 ttctgtttct ctccgtgctg ttctctcccg ctgtgcgcct gcccgcctct cgctgtcctc    180
tctccccctc gccctctctt cggcccccc cctttcacgtt cactctgtct ctcccactat    240
ctctgccccc ctctatcctt gatacaacag ctgacctcat ttcccgatac cttttccccc    300
ccgaaaagta caacatctgg cccgcccag cccgaagaca gcccgtcctc cctggacaat     360
cagacgaatt ctccccccccc cccaaaaaa aaaagccatc ccccgctct gccccgtcgc     420 acattcggcc cccgcgactc ggccagagcg gcgctggcag aggagtgtcc ggcaggaggg    480
ccaacgcccg ctgttcggtt tgcgacacgc agcagggagg tgggcggcag cgtcgccggc    540
ttccagacac ca atg gga atc cca atg ggg aag tcg atg ctg gtg ctt ctc      591
              Met Gly Ile Pro Met Gly Lys Ser Met Leu Val Leu Leu
              1               5                  10 acc ttc ttg gcc ttc gcc tcg tgc tgc att gct gct tac cgc ccc agt       639
Thr Phe Leu Ala Phe Ala Ser Cys Cys Ile Ala Ala Tyr Arg Pro Ser
 15                  20                  25 gag acc ctg tgc ggc ggg gag ctg gtg gac acc ctc cag ttc gtc tgt       687
Glu Thr Leu Cys Gly Gly Glu Leu Val Asp Thr Leu Gln Phe Val Cys
 30                  35                  40                  45 ggg gac cgc ggc ttc tac ttc agc agg ccc gca agc cgt gtg agc cgt       735
Gly Asp Arg Gly Phe Tyr Phe Ser Arg Pro Ala Ser Arg Val Ser Arg
                 50                  55                  60 cgc agc cgt ggc atc gtt gag gag tgc tgt ttc cgc agc tgt gac ctg       783
Arg Ser Arg Gly Ile Val Glu Glu Cys Cys Phe Arg Ser Cys Asp Leu
         65                  70                  75 gcc ctc ctg gag acg tac tgt gct acc ccc gcc aag tcc gag agg gac       831
Ala Leu Leu Glu Thr Tyr Cys Ala Thr Pro Ala Lys Ser Glu Arg Asp
             80                  85                  90 gtg tcg acc cct ccg acc gtg ctt ccg gac aac ttc ccc aga tac ccc       879
Val Ser Thr Pro Pro Thr Val Leu Pro Asp Asn Phe Pro Arg Tyr Pro
             95                  100                 105 gtg ggc aag ttc ttc caa tat gac acc tgg aag cag tcc acc cag cgc       927
Val Gly Lys Phe Phe Gln Tyr Asp Thr Trp Lys Gln Ser Thr Gln Arg
110                 115                 120                 125 ctg cgc agg ggc ctg cct gcc ctc ctg cgt gcc cgc cgg ggt cac gtg       975
Leu Arg Arg Gly Leu Pro Ala Leu Leu Arg Ala Arg Arg Gly His Val
                 130                 135                 140 ctc gcc aag gag ctc gag gcg ttc agg gag gcc aaa cgt cac cgt ccc      1023
Leu Ala Lys Glu Leu Glu Ala Phe Arg Glu Ala Lys Arg His Arg Pro
             145                 150                 155 ctg att gct cta ccc acc caa gac ccc gcc cac ggg ggc gcc ccc cca      1071
Leu Ile Ala Leu Pro Thr Gln Asp Pro Ala His Gly Gly Ala Pro Pro
         160                 165                 170 gag atg gcc agc aat cgg aag tga gcaaaactgc cgcaagtctg cagcccggcg     1125
Glu Met Ala Ser Asn Arg Lys
```

```
Glu Met Ala Ser Asn Arg Lys  *
    175                 180 ccaccatcct gcagcctcct cctgaccacg gacgtttcca tcaggttcca tcccgaaaat    1185
ctctcggttc cacgtccccc tggggcttct cctgacccag tccccgtgcc ccgcctcccc    1245
gaaacaggct actctcctcg gcccccctcca tcgggctgag gaagcacagc agcatcttca   1305
aacatgtaca aaatcgattg gctttaaaca cccttcacat accctcccccc c            1356

<210> SEQ ID NO 38
<211> LENGTH: 180
<212> TYPE: PRT
<213> ORGANISM: Homo sapiens

<400> SEQUENCE: 38

Met Gly Ile Pro Met Gly Lys Ser Met Leu Val Leu Leu Thr Phe Leu
  1               5                  10                  15

Ala Phe Ala Ser Cys Cys Ile Ala Ala Tyr Arg Pro Ser Glu Thr Leu
             20                  25                  30

Cys Gly Gly Glu Leu Val Asp Thr Leu Gln Phe Val Cys Gly Asp Arg
         35                  40                  45

Gly Phe Tyr Phe Ser Arg Pro Ala Ser Arg Val Ser Arg Arg Ser Arg
     50                  55                  60

Gly Ile Val Glu Glu Cys Cys Phe Arg Ser Cys Asp Leu Ala Leu Leu
 65                  70                  75                  80

Glu Thr Tyr Cys Ala Thr Pro Ala Lys Ser Glu Arg Asp Val Ser Thr
                 85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
            180
```